(12) United States Patent
Wunderle et al.

(10) Patent No.: US 10,767,225 B2
(45) Date of Patent: *Sep. 8, 2020

(54) VALVED CARTRIDGE AND SYSTEM

(71) Applicant: IntegenX, Inc., Pleasanton, CA (US)

(72) Inventors: Philip Justus Wunderle, Oakland, CA (US); Chungsoo Charles Park, Redwood City, CA (US); David King, Menlo Park, CA (US); Dennis Lehto, Santa Clara, CA (US)

(73) Assignee: IntegenX, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/264,389

(22) Filed: Jan. 31, 2019

(65) Prior Publication Data
US 2019/0233888 A1 Aug. 1, 2019

Related U.S. Application Data

(62) Division of application No. 15/173,894, filed on Jun. 6, 2016, now Pat. No. 10,233,491.
(Continued)

(51) Int. Cl.
*C12Q 1/6874* (2018.01)
*C12Q 1/686* (2018.01)
(Continued)

(52) U.S. Cl.
CPC ...... *C12Q 1/6874* (2013.01); *B01L 3/502738* (2013.01); *C12Q 1/686* (2013.01);
(Continued)

(58) Field of Classification Search
CPC ... C12Q 1/6874; C12Q 1/686; F16K 99/0034; F16K 99/0015; F16K 2099/0084;
(Continued)

(56) References Cited

U.S. PATENT DOCUMENTS 3,075,740 A 1/1963 McKintosh
3,662,517 A 5/1972 Tascher et al.
(Continued)

FOREIGN PATENT DOCUMENTS

CN 1354692 A 6/2002
CN 1593338 A 3/2005
(Continued)

OTHER PUBLICATIONS

U.S. Appl. No. 14/659,108, filed Mar. 16, 2015.
(Continued)

*Primary Examiner* — Sally A Merkling
(74) *Attorney, Agent, or Firm* — Workman Nydegger

(57) ABSTRACT

This disclosure provides, among other things, a cartridge comprising: (a) a cartridge body comprising a malleable material and having, disposed on a surface of the body, at least one valve body comprising a valve inlet and a valve outlet, each fluidically connected to a fluidic channel; and (b) a layer comprising a deformable material bonded to a surface of the cartridge body and sealing the at least one valve body at points of attachment, thereby forming at least one valve; wherein the at least one valve body is depressed in the cartridge body relative to the points of attachment and wherein the deformable material covering the at least one valve body retains sufficient elasticity after deformation such that in a ground state the valve is open. Also disclosed is an instrument comprising a cartridge interface and a cartridge as described herein engaged with the cartridge interface, wherein (II) the cartridge interface comprises: (A) at least one mechanical actuator, each mechanical actuator positioned to actuate a valve; and (B) at least one motor operatively coupled to actuate a mechanical actuator toward or away from a valve.

20 Claims, 29 Drawing Sheets

Related U.S. Application Data

(60) Provisional application No. 62/233,852, filed on Sep. 28, 2015, provisional application No. 62/182,291, filed on Jun. 19, 2015.

(51) Int. Cl.
| | | |
|---|---|---|
| *B01L 3/00* | (2006.01) | |
| *F16K 99/00* | (2006.01) | |
| *B01L 7/00* | (2006.01) | |
| *B01F 13/00* | (2006.01) | |
| *B01F 13/02* | (2006.01) | |

(52) U.S. Cl.
CPC ...... *F16K 99/0015* (2013.01); *F16K 99/0034* (2013.01); *B01F 13/0059* (2013.01); *B01F 13/02* (2013.01); *B01L 3/502753* (2013.01); *B01L 7/52* (2013.01); *B01L 2200/04* (2013.01); *B01L 2200/0668* (2013.01); *B01L 2200/16* (2013.01); *B01L 2300/0816* (2013.01); *B01L 2300/0887* (2013.01); *B01L 2300/123* (2013.01); *B01L 2400/043* (2013.01); *B01L 2400/0478* (2013.01); *B01L 2400/0655* (2013.01); *F16K 2099/0078* (2013.01); *F16K 2099/0084* (2013.01)

(58) Field of Classification Search
CPC ....... F16K 2099/0078; B01L 3/502738; B01L 2400/0478; B01L 2400/043; B01L 2300/0816; B01L 2200/16; B01L 2200/0668; B01L 2200/04; B01L 7/52; B01L 3/502753; B01L 2400/0655; B01L 2300/123; B01L 2300/0887; B01F 13/02; B01F 13/0059
See application file for complete search history.

(56) References Cited

U.S. PATENT DOCUMENTS

| | | | |
|---|---|---|---|
| 5,922,591 A | 7/1999 | Anderson et al. | |
| 6,190,616 B1 | 2/2001 | Jovanovich et al. | |
| 6,197,595 B1 | 3/2001 | Anderson et al. | |
| 6,326,068 B1 | 12/2001 | Kong et al. | |
| 6,461,492 B1 | 10/2002 | Hayashizaki et al. | |
| 6,551,839 B2 | 4/2003 | Jovanovich et al. | |
| 6,623,613 B1 | 9/2003 | Mathies et al. | |
| 6,740,219 B2 | 5/2004 | Kazumichi et al. | |
| 6,782,746 B1* | 8/2004 | Hasselbrink, Jr. ........ F15C 5/00 73/253 |
| 6,870,185 B2 | 3/2005 | Roach et al. | |
| 6,883,774 B2 | 4/2005 | Nielsen et al. | |
| 7,005,052 B2 | 2/2006 | Shimizu et al. | |
| 7,046,357 B2 | 5/2006 | Weinberger et al. | |
| 7,097,809 B2 | 8/2006 | Van et al. | |
| 7,244,961 B2 | 7/2007 | Jovanovich et al. | |
| 7,318,912 B2 | 1/2008 | Pezzuto et al. | |
| 7,473,397 B2 | 1/2009 | Griffin et al. | |
| 7,595,200 B2 | 9/2009 | Bedingham et al. | |
| 7,763,453 B2 | 7/2010 | Clemmens et al. | |
| 7,785,458 B2 | 8/2010 | Shimizu et al. | |
| 7,803,281 B2 | 9/2010 | Davies et al. | |
| 8,142,635 B2 | 3/2012 | Shimizu et al. | |
| 8,268,263 B2 | 9/2012 | Campbell et al. | |
| 8,313,941 B2 | 11/2012 | Takayama et al. | |
| 8,337,777 B2 | 12/2012 | Nurse et al. | |
| 8,394,642 B2 | 3/2013 | Jovanovich et al. | |
| 8,431,340 B2 | 4/2013 | Jovanovich et al. | |
| 8,501,305 B2 | 8/2013 | Barlow | |
| 8,512,538 B2 | 8/2013 | Majlof et al. | |
| 8,584,703 B2 | 11/2013 | Kobrin et al. | |
| 9,341,284 B2 | 5/2016 | Vangbo | |
| 9,546,932 B2 | 1/2017 | Putnam et al. | |
| 2001/0012612 A1 | 8/2001 | Petersen et al. | |
| 2002/0137039 A1 | 9/2002 | Gessner | |
| 2002/0187560 A1 | 12/2002 | Pezzuto et al. | |
| 2003/0197139 A1 | 10/2003 | Williams | |
| 2004/0022676 A1 | 2/2004 | Hamilton et al. | |
| 2004/0115838 A1 | 6/2004 | Quake et al. | |
| 2004/0195539 A1 | 10/2004 | Mead et al. | |
| 2004/0209354 A1 | 10/2004 | Mathies et al. | |
| 2005/0287572 A1 | 12/2005 | Mathies et al. | |
| 2006/0073484 A1 | 4/2006 | Mathies et al. | |
| 2006/0260941 A1 | 11/2006 | Tan et al. | |
| 2007/0084706 A1 | 4/2007 | Takayama et al. | |
| 2007/0237686 A1 | 10/2007 | Mathies et al. | |
| 2007/0292941 A1 | 12/2007 | Handique et al. | |
| 2008/0241844 A1 | 10/2008 | Kellogg | |
| 2008/0311585 A1 | 12/2008 | Gao et al. | |
| 2009/0020427 A1 | 1/2009 | Tan et al. | |
| 2009/0023603 A1 | 1/2009 | Selden et al. | |
| 2009/0056822 A1 | 3/2009 | Young et al. | |
| 2009/0178934 A1 | 7/2009 | Jarvius et al. | |
| 2009/0253181 A1 | 10/2009 | Vangbo et al. | |
| 2009/0314970 A1 | 12/2009 | McAvoy et al. | |
| 2010/0111770 A1 | 5/2010 | Hwang et al. | |
| 2010/0172898 A1 | 7/2010 | Doyle et al. | |
| 2010/0173398 A1 | 7/2010 | Peterman | |
| 2010/0221726 A1 | 9/2010 | Zenhausern et al. | |
| 2010/0228513 A1 | 9/2010 | Roth et al. | |
| 2010/0266432 A1 | 10/2010 | Pirk et al. | |
| 2010/0285578 A1 | 11/2010 | Selden et al. | |
| 2010/0285975 A1 | 11/2010 | Mathies et al. | |
| 2010/0303687 A1 | 12/2010 | Blaga et al. | |
| 2011/0005932 A1 | 1/2011 | Jovanovich et al. | |
| 2011/0008785 A1 | 1/2011 | Tan et al. | |
| 2011/0014606 A1 | 1/2011 | Steinmetzer et al. | |
| 2011/0039303 A1 | 2/2011 | Jovanovich et al. | |
| 2011/0053784 A1 | 3/2011 | Unger et al. | |
| 2011/0124049 A1 | 5/2011 | Bin et al. | |
| 2011/0126911 A1 | 6/2011 | Kobrin et al. | |
| 2011/0136179 A1 | 6/2011 | Binlee et al. | |
| 2011/0137018 A1 | 6/2011 | Chang-Yen et al. | |
| 2011/0171086 A1 | 7/2011 | Prins et al. | |
| 2011/0189678 A1 | 8/2011 | McBride et al. | |
| 2011/0195495 A1 | 8/2011 | Selden et al. | |
| 2011/0212440 A1 | 9/2011 | Viovy et al. | |
| 2011/0229897 A1 | 9/2011 | Bell et al. | |
| 2011/0229898 A1 | 9/2011 | Bell et al. | |
| 2011/0312614 A1 | 12/2011 | Selden et al. | |
| 2012/0181460 A1 | 7/2012 | Eberhart et al. | |
| 2012/0267247 A1 | 10/2012 | Tan et al. | |
| 2012/0322666 A1 | 12/2012 | Pham et al. | |
| 2013/0084565 A1 | 4/2013 | Landers et al. | |
| 2013/0115607 A1 | 5/2013 | Nielsen et al. | |
| 2013/0137591 A1 | 5/2013 | Clemens et al. | |
| 2013/0139895 A1* | 6/2013 | Vangbo ............ B01L 3/502738 137/2 |
| 2013/0203634 A1 | 8/2013 | Jovanovich et al. | |
| 2013/0209326 A1 | 8/2013 | Williams et al. | |
| 2013/0210129 A1 | 8/2013 | Selden et al. | |
| 2013/0213810 A1 | 8/2013 | Tan et al. | |
| 2013/0217026 A1 | 8/2013 | Egan et al. | |
| 2013/0230906 A1 | 9/2013 | Martinelli et al. | |
| 2013/0240140 A1 | 9/2013 | Kurowski et al. | |
| 2013/0260380 A1 | 10/2013 | Hall et al. | |
| 2013/0273592 A1 | 10/2013 | Colin et al. | |
| 2013/0287645 A1 | 10/2013 | Shaikh et al. | |
| 2013/0331298 A1 | 12/2013 | Rea | |
| 2014/0073043 A1 | 3/2014 | Holmes et al. | |
| 2014/0370519 A1 | 12/2014 | Vangbo et al. | |
| 2015/0021502 A1 | 1/2015 | Vangbo | |
| 2015/0024436 A1 | 1/2015 | Eberhart et al. | |
| 2015/0136602 A1 | 5/2015 | Jovanovich et al. | |
| 2015/0136604 A1 | 5/2015 | Nielsen et al. | |
| 2016/0016140 A1 | 1/2016 | Jovanovich et al. | |
| 2016/0053314 A1 | 2/2016 | Jovanovich et al. | |
| 2016/0096176 A1 | 4/2016 | Jarvius et al. | |
| 2016/0116439 A1 | 4/2016 | Kindwall et al. | |

(56) References Cited

U.S. PATENT DOCUMENTS

2016/0305972 A1 10/2016 Ogg et al.
2017/0002399 A1 1/2017 Eberhart et al.

FOREIGN PATENT DOCUMENTS

| | | |
|---|---|---|
| CN | 101004423 A | 7/2007 |
| CN | 101553306 | 10/2009 |
| CN | 102459565 A | 10/2009 |
| EP | 1 905 514 A1 | 4/2008 |
| WO | WO-2009129415 A1 | 10/2009 |
| WO | WO-2010041174 A1 | 4/2010 |
| WO | WO-2010130762 A2 | 11/2010 |
| WO | WO-2011012621 A1 | 2/2011 |
| WO | WO-2011056215 A1 | 5/2011 |
| WO | WO-2011084703 A2 | 7/2011 |
| WO | WO-2012136333 A2 | 10/2012 |
| WO | WO-2013130910 A1 | 9/2013 |
| WO | WO-2014055936 A1 | 4/2014 |
| WO | 2015/073999 A1 | 5/2015 |
| WO | WO-2015073999 A1 | 5/2015 |
| WO | WO-2015078998 A1 | 6/2015 |

OTHER PUBLICATIONS

U.S. Appl. No. 14/824,333, filed Aug. 12, 2015.
U.S. Appl. No. 14/919,620, filed Oct. 21, 2015.
U.S. Appl. No. 15/037,039, filed May 16, 2016.
U.S. Appl. No. 15/117,053, filed Aug. 5, 2016.
U.S. Appl. No. 15/154,086, filed May 13, 2016.
U.S. Appl. No. 62/067,429, filed Oct. 22, 2014.
International search report and written opinion dated Sep. 16, 2016 for PCT Application No. US2016/37711.
Notice of Allowance issued in U.S. Appl. No. 15/037,039, dated Sep. 11, 2018.
CN Search Report issued in Application No. 201480071855.1, dated Apr. 12, 2017.
CN Supplemental Search Report issued in Application No. 201480071855.1, dated Feb. 4, 2018.
CN First Office Action issued in Application No. 201480071855.1, dated Apr. 20, 2017.
CN Second Office Action issued in Application No. 201480071855.1, dated Feb. 11, 2018.
CN Third Office Action issued in Application No. 201480071855.1, dated Aug. 13, 2018.
EP Partial Search Report dated Jul. 12, 2017 issued in Application No. EP14861199.
EP Search Report and Written Opinion issued in Application No. EP14861199, dated Oct. 18, 2017.
EP Office Action issued in Application No. 14861199.9, dated Oct. 9, 2018.
International Search Report and Written Opinion, issued in PCT Application No. PCT/US14/66008, dated Mar. 3, 2015.
International Preliminary Report on Patentability, issued in PCT Application No. PCT/US14/66008, dated May 24, 2016.
Office Action issued in U.S. Appl. No. 15/117,053, dated May 7, 2018.
Notice of Allowance issued in U.S. Appl. No. 15/117,053, dated Oct. 1, 2018.
International search report and written opinion dated Oct. 26, 2015 issued in Application No. PCT/US2015/028510.
International Preliminary Report of Patentability issued in Application No. PCT/US15/28510 dated Dec. 1, 2016.
Lai et al., "Design and Dynamic Characterization of "Single-Stroke" Peristaltic PDMS Micropumps," The Royal Society of Chemistry, Lab Chip, 2011, vol. 11, pp. 336-342.
Tanaka et al., "An Active Valve Incorporated into a Microchip Using a High Strain Electroactive Polymer," Sensors and Actuators B: Chemical, vol. 184, Apr. 20, 2013, pp. 163-169.
Au et al., "Microvalves and Micropumps for BioMEMS," Micromachines May 24, 2011, vol. 2, pp. 179-220.
Office Action dated Jan. 23, 2018, issued in U.S. Appl. No. 15/173,894.
Notice of Allowance dated Nov. 1, 2018, issued in U.S. Appl. No. 15/173,894.
U.S. Appl. No. 16/258,412, filed Jan. 25, 2019, Ogg et al.
U.S. Appl. No. 16/250,646, filed Jan. 17, 2019, Eberhart et al.
U.S. Appl. No. 15/342,914, filed Nov. 3, 2016.

* cited by examiner

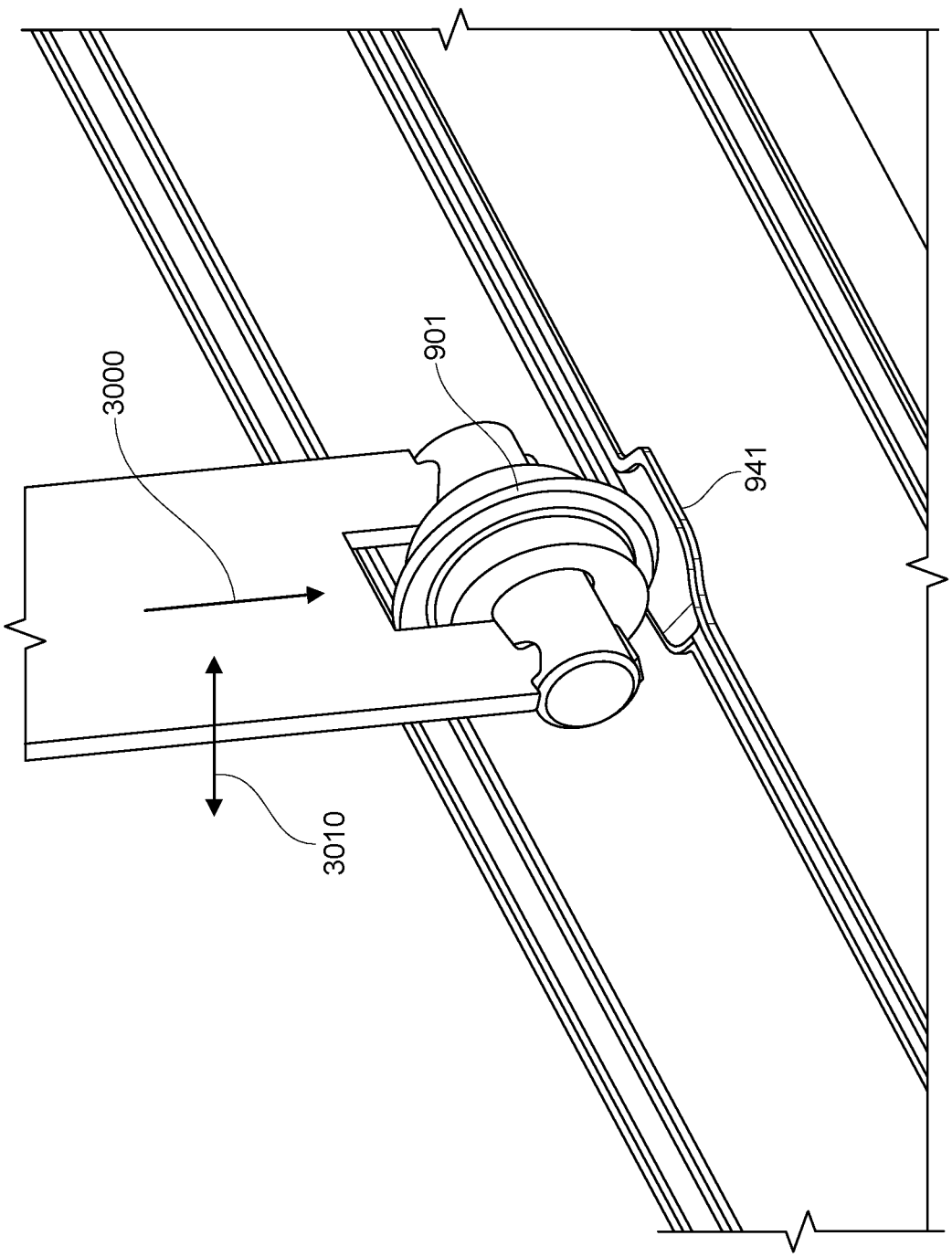

| Step # chemistry steps | Cycler out (A0) | Lysis (A1) | Lysis (A2) | Waste Shut off (A3) | Waste in (A4) | Cycler in (B0) | Lysis Transfer (B1) | Product Bottom (B2) | Product Top (B3) | Vent (B4) |
|---|---|---|---|---|---|---|---|---|---|---|
| 1 Load SC | O | O | O | O | O | O | O | O | O | O |
| 2 Prime Lysis to waste* | O | C | O | O | C | O | O | O | C | O |
| 3 Dispense Lysis to Lysis Chamber | O | O | O | C | O | O | C | O | C | O |
| 4 Mix Lysis with Air | O | O | O | O | O | O | C | O | C | O |
| 5 Mix and Heat Lysis | O | C | O | O | O | O | O | C | C | C |
| 6 Pull Lysate to Waste via RC | O | C | O | C | O | O | O | C | C | O |
| 7 Push PMx and MMx to RC | O | C | C | O | O | C | C | C | C | C |
| 8 Thermal Cycling | C | C | C | O | C | C | C | C | C | O |
| 9 Push ILS and Product thru RC to Mix Chamber | C | C | C | C | C | O | C | O | O | O |
| 10 Push Residual ILS and Product to Mix Chamber with Air Pump | O | C | C | O | C | O | C | O | O | O |
| 11 Push Product to Cathode | O | C | O | C | O | O | C | C | O | O |
| 12 Water Rinse of MC and Product Output to Cathode | O | C | C | C | C | O | C | C | O | O |
| 13 Water Rinse of MC and RC | O | C | C | C | O | O | C | O | C | O |
| 14 Flush Water out of SC to waste Chamber | O | C | C | C | C | O | C | C | O | O |
| 15 Flush water from SC and Line to Cathode | O | C | O | C | C | O | C | O | O | O |
| 16 Release | O | O | O | O | O | O | O | O | O | O |

FIG. 28

VALVED CARTRIDGE AND SYSTEM

REFERENCE TO RELATED APPLICATIONS

This application is a non-provisional application of U.S. Provisional application 62/233,852, filed Sep. 28, 2015 and U.S. Provisional application 62/182,291, filed Jun. 19, 2015, each of which is incorporated herein by reference in its entirety.

STATEMENT AS TO FEDERALLY SPONSORED RESEARCH

None.

BACKGROUND OF THE INVENTION

Versions of systems including sample cartridges and fluidic systems for sample extraction and analysis are described in, for example, U.S. Pat. Nos. 6,190,616; 6,551,839; 6,870,185; 7,244,961; 8,394,642 and 8,431,340; US patent applications 2006/0073484; 2009/0253181; 2011/0039303; 2011/0126911; 2012/0181460; 2013/0139895 and 2013/0115607; and International Patent Applications PCT/US2013/130910 and PCT/EP2012/001413.

US patent publication 2003/0197139 refers to a valve for use in microfluidic structures.

US patent publication 2009/0314970 refers to a mechanically-actuated microfluidic pinch valve.

US patent publication 2013/0240140 refers to a process for producing a microfluidic apparatus and related laminating devices.

International publication WO 2012/136333 refers to a heat weldable film for labeling plastic polymeric reaction tubes.

U.S. Pat. No. 6,883,774 refers to a microvalve and method of forming a microvalve.

U.S. Pat. No. 7,318,912 refers to microfluidic systems and methods for combining discreet fluid volumes.

U.S. Pat. No. 8,313,941 refers to integrated microfluidic control employing programmable tactile actuators.

U.S. Pat. No. 8,501,305 refers to a laminate.

The statements in the Background are not necessarily meant to endorse the characterization in the cited references or admit their availability as prior art.

BRIEF SUMMARY OF THE INVENTION

In one aspect disclosed herein is a fluidic device comprising: (a) a substrate comprising a malleable material and having, disposed on a surface of the body, at least one valve body comprising a valve inlet and a valve outlet, each fluidically connected to a fluidic channel; and (b) a layer comprising a deformable material bonded to a surface of the substrate and sealing the at least one valve body at points of attachment, thereby forming at least one valve; wherein the at least one valve body is depressed in the substrate relative to the points of attachment and wherein the deformable material covering the at least one valve body retains sufficient elasticity after deformation such that in a ground state the valve is open. In one embodiment, the fluidic device is a microfluidic chip.

In another aspect provided herein is in a cartridge comprising: (a) a cartridge body comprising a malleable material and having, disposed on a surface of the body, at least one valve body comprising a valve inlet and a valve outlet, each fluidically connected to a fluidic channel; and (b) a layer comprising a deformable material bonded to a surface of the cartridge body and sealing the at least one valve body at points of attachment, thereby forming at least one valve; wherein the at least one valve body is depressed in the cartridge body relative to the points of attachment and wherein the deformable material covering the at least one valve body retains sufficient elasticity after deformation such that in a ground state the valve is open. In one embodiment the malleable material has undergone a plastic deformation as a result of initial valve closure. In another embodiment the at least one valve body is a plurality of valve bodies. In another embodiment the points of attachment comprise ridges elevated above the surface. In another embodiment the valve inlet and the valve outlet are fluidically connected with fluidic channels. In another embodiment the malleable material comprises a plastic, a wax or a soft metal. In another embodiment the malleable material comprises a thermoplastic, a thermoset, a single component resin or a multi-component resin. In another embodiment the malleable material comprises polypropylene, polystyrene, polyethylene, polyethylene terephthalate, polyester, polyamide, vinyl, poly(vinylchloride) (PVC), polycarbonate, polyurethane, polyvinyldiene chloride, cyclic olefin polymer (COP), cyclic olefin copolymer (COC), or any combination thereof. In another embodiment the deformable material comprises Santoprene a TPE (thermoplastic elasotomer) e.g., Santoprene, a blend of EPDM rubber and polypropylene. In another embodiment the deformable material has a durometer value of between 10 Shore D to 80 Shore D. In another embodiment the deformable material comprises a heat seal material. In another embodiment a portion of the layer of deformable material covering a valve seat does not comprise an elastomeric material, e.g., is not PDMS. In another embodiment the layer of deformable material has a higher yield strength than the malleable material. In another embodiment the deformable material is attached to the body through an adhesive. In another embodiment the deformable material is welded to the body. In another embodiment the deformable material comprises a material selected from polypropylene, polyethylene, polystyrene, cyclic olefin polymer (COP), cyclic olefin co-polymer (COC), mylar, polyacetate) and a metal. In another embodiment the cartridge comprises at least one fluidic circuit, wherein the at least one fluidic circuit comprises, as elements, at least one valve, at least one fluid inlet, at least one fluid outlet and at least one compartment, which elements are fluidically connected through fluidic channels. In another embodiment the at least one compartment is selected from a reagent compartment, a sample compartment, a mixing compartment, a reaction compartment and a waste compartment. In another embodiment at least one fluid inlet or a fluid outlet comprises a via through the cartridge body. In another embodiment at least one compartment is a sample compartment configured to accept a swab. In another embodiment at least one compartment is mixing chamber configured for bubbling of air through the mixing chamber. In another embodiment at least one compartment is a reaction chamber comprising a solid substrate, e.g., solid phase extraction material, for retaining analyte from a sample. In another embodiment the solid substrate comprises a material that binds nucleic acid. In another embodiment the solid substrate comprises Whatman paper, a carboxylated particle, a sponge-like material, a polymer membrane, magnetically attractable particles, or glass particles. In another embodiment the solid substrate binds a predetermined amount of material. In another embodiment the at least one fluidic circuit comprises a pump configured as a depression in the surface. In another embodiment at least one compartment is a reaction chamber comprising one or more thermally conductive walls and configured for thermal cycling. In another embodiment at least one compartment is a waste compartment. In another embodiment the waste compartment comprises a material that degrades nucleic acid. In another embodiment the material that degrades nucleic acid comprises a hypochlorite salt. In another embodiment the body further comprises at least one reagent compartment comprising a reagent, wherein the compartment comprises an openable seal that, when opened, puts the compartment in fluidic communication through a via with a fluidic channel on the surface. In another embodiment the deformable layer retains sufficient elasticity to resist valve closure when negative pressure (e.g., suction) up to about 10 psi is exerted on a fluidic channel communicating with the valve. In another embodiment the valve body and a ram configured to close the valve have shapes such that closure of the valve produces a pressure that is normal to the surface of the valve body across all areas of the valve cross section, e.g., when the pressure of the ram is unidirectional. In another embodiment the valve body is wider than the channel to which it is connected. In another embodiment the cartridge body further comprises one or more reagent compartments comprising reagents including nucleic acid primers, nucleotides and DNA polymerases sufficient to perform PCR. In another embodiment the reagents are sufficient for performing multiplex PCR on SIR loci. In another embodiment the cartridge further comprises a chamber comprising a filter, e.g., a size exclusion filter. In another embodiment one of the chambers is configured as a lysis chamber configured to accept a biological sample, one of the chambers is configured as a mixing chamber configured to bubble air when liquid is contained in the mixing chamber, and one of the chambers is configured as a reaction chamber comprising one or more thermally conductive walls and configured for thermal cycling. In another embodiment the cartridge further comprises at least one reagent compartment comprising reagents for performing PCR (e.g., PCR primers, nucleotides and a DNA polymerase), wherein the at least one reagent chamber comprises an openable seal that, when opened, puts the reagent chamber in fluidic communication with the reaction chamber. In another embodiment at least one reagent chamber comprises PCR primers selected to amplify a plurality of SIR loci. In another embodiment one of the chambers is configured as a lysis chamber configured to accept a biological sample, one of the chambers is configured as an isolation chamber configured to receive magnetically responsive capture particles and to immobilize said particles when a magnetic force is applied to the isolation chamber, and one of the chambers is configured as a reaction chamber comprising one or more thermally conductive walls and configured for thermal cycling. In another embodiment the cartridge further comprises at least two sets of reagent compartments, wherein a first set of reagent compartments comprises reagents for performing PCR, and wherein a second set of reagent compartments comprises reagents for performing cycle sequencing, wherein each reagent compartment comprises openable seal that, when opened, puts the reagent compartment in fluidic communication with the reaction chamber. In another embodiment the cartridge further comprises a reagent compartment comprising reagents to degrade PCR primers and nucleotide triphosphates. In another embodiment the cartridge further comprises at least two sets of reagent compartments, wherein both the first set of reagent compartments and the second set of reagent compartments comprise reagents for performing PCR, and wherein each reagent compartment comprises openable seal that, when opened, puts the reagent compartment in fluidic communication with the reaction chamber. In another embodiment the PCR reagents in one of the sets of reagent compartments comprises reagents for performing adapted for performing quantification of human DNA. In another embodiment the cartridge comprises a branched fluidic circuit comprising chambers connected by fluidic channels and comprising a common portion and a plurality of branches, wherein the common portion comprises a fluid inlet and a lysis chamber, and wherein each branch comprises at least one reaction chamber comprising one or more thermally conductive walls and configured for thermal cycling, at least one isolation chamber and a fluid outlet, wherein at least the fluidic channels connecting a reaction chamber with an isolation chamber comprises a valve body. In another embodiment the common portion comprises a common isolation chamber. In another embodiment each branch further comprises at least one reagent chamber reagent compartment comprising an openable seal that, when opened, puts the reagent compartment in fluidic communication with the reaction chamber in the branch. In another embodiment the cartridge comprises two branches, wherein a first branch comprises reagents to perform a forward cycle sequencing reaction on a target polynucleotide and a second branch comprises reagents to perform a reverse cycle sequencing reaction on a target polynucleotide.

In another aspect provided herein is an article comprising: (a) a cartridge body comprising a malleable material and having, disposed on a surface of the body, at least one valve body comprising a valve inlet and a valve outlet, each fluidically connected to a fluidic channel, wherein the at least one valve body comprises sloped or curved walls. In one embodiment In another embodiment the walls are configured to exert a centering action on a tapered ram head pressed against the valve body. In another embodiment the at least one valve body is not radially symmetric (e.g., is longer in one dimension of the XY plane of the surface than the other. In another embodiment the at least one valve body does not comprise valve reliefs flanking the valve body. In another embodiment the at least one body does not have a flat floor. In another embodiment lines tangent to surfaces of opposing walls at the same depth form an acute angle. In another embodiment the at least one valve body has opposing sloped walls. In another embodiment the at least one valve body has curved walls. In another embodiment the article is configured to exert a centering action on a tapered ram head pressed against the heat seal layer which presses against the valve body. In another embodiment the one or more valve bodies do not comprise valve reliefs flanking the valve body. In another embodiment the valve body has an aspect ratio of depth-to-width greater than 1. In another embodiment the one or more valve bodies do not comprise a sharp angle. In another embodiment the one or more valve bodies do not have a flat floor. In another embodiment the one or more valve bodies have a diameter between about 0.2 mm (200 microns) and about 2 mm. In another embodiment the aspect ratio (widtlrdepth) of the valve body is between about 1:1.5 and 1:0.1, e.g., 1:1.2 to 1:0.7. In another embodiment lines drawn tangent to the opposing walls of the valve body at any point between the top and bottom of the valve body form an angle of at least any of is at least any of 30°, 45° or 60° and at most any of 150°, 125° or 100°. In another embodiment the valve body has a depth, from its bottom to the height of the top of a ridge (if present) or a plane generally defined by the cartridge body surface of between 50 microns and 200 microns, e.g., about 100 microns. In another embodiment a cross-section of the at least one valve body has walls taking the shape of a portion of any of a wedge, a circle, an ellipse, an oval, a catenary. In another embodiment the article further comprises a relief adapted to accept a centering arm for guiding a ram head.

In another aspect provided herein is a method of making an article comprising: (a) providing a cartridge body comprising a malleable material and having, disposed on a surface of the body, at least one valve body comprising a valve inlet and a valve outlet, each fluidically connected to a fluidic channel; and (b) providing a layer comprising a deformable material; (c) bonding the layer to the surface to seal the at least one valve body at points of attachment, thereby forming at least one valve, wherein the at least one valve body is depressed in the cartridge body relative to the points of attachment; and (d) deforming the deformable layer covering the at least one valve body wherein the deformable layer undergoes plastic deformation and retains sufficient elasticity such that in a ground state the valve is open. In one embodiment bonding comprises heat sealing or welding. In another embodiment deforming comprises putting mechanical pressure on the deformable layer. In another embodiment mechanical pressure is applied using a ram. In another embodiment the ram has a tip having a shape that conforms substantially to the shape of the valve body offset for the thickness of the deformable layer. In another embodiment valve body has a cross-sectional shape that exerts a centering action on the ram toward a center of the valve body as the ram applies pressure on the deformable layer. In another embodiment the ram comprises a flexible material. In another embodiment the ram is mounted on a pivot or a rocker arm. In another embodiment a ram assembly comprises a centering arm configured for coarse centering of the ram head. In another embodiment the ram comprises a rotatable wheel mounted at an end of the ram, and wherein the valve body has a cross-sectional shape that conforms substantially to the wheel offset by the thickness of the deformable layer. In another embodiment the ram is configured to translate laterally with respect to the surface of the cartridge body.

In another aspect provided herein is an instrument comprising a cartridge interface and a cartridge engaged with the cartridge interface, wherein: (I) the cartridge is a cartridge as provided herein; (II) the cartridge interface comprises: (A) at least one mechanical actuator, each mechanical actuator positioned to actuate a valve; (B) at least one motor operatively coupled to actuate a mechanical actuator toward or away from a valve. In one embodiment (I) the cartridge comprises at least one fluidic circuit, wherein the at least one fluidic circuit comprises, as elements, at least one valve, at least one fluid inlet, at least one fluid outlet and at least one compartment, which elements are fluidically connected through fluidic channels; and (II) the cartridge interface comprises a first port engaged with a fluid inlet and a second port engaged with a fluid outlet, and further comprises a pressure source configured to apply positive or negative pressure through either port to the fluidic circuit. In another embodiment the pressure source provides pneumatic pressure. In another embodiment (I) the cartridge comprises a plurality of valves; and (II) the cartridge interface comprises a plurality of mechanical actuators, wherein each mechanical actuator can be independently actuated. In another embodiment the instrument further comprises a source of at least one reagent, and a pump configured to pump the reagent into a fluid inlet.

In another aspect provided herein is a method of controlling fluid flow in a fluid channel of fluidic cartridge comprising: (A) providing an instrument as provided herein, wherein at least one of the fluidic channels comprises a liquid; (B) closing a valve by actuating a mechanical actuator against the valve to force the deformable layer against walls of the valve body; (C) releasing the valve by retracting the mechanical actuator away from the valve body; and (D) moving the liquid through the valve by applying positive or negative pressure to liquid in a fluidic channel.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 12 shows a ram on which a downward force 3000 is applied to close a valve. The ram also has lateral play 3010 to allow centering of the ram in the valve body, promoted by turning of wheel 901 into the valve body.

FIG. 28 shows a sequence of steps in sample preparation. "O" indicates a ram does not press against a valve. "X" indicates a ram presses against and closes a valve.

DETAILED DESCRIPTION OF THE INVENTION

I. Introduction

This disclosure provides, among other things, a valve for a fluidic device, such as a mesofluidic or microfluidic device. The device can be a cartridge adapted to engage a cartridge interface that operates activities within the cartridge. Alternatively, the device can be a fluidic device comprising the valve and included as an integral part of a system that performs fluidic operations. The fluidic device can comprise a substrate having a surface with fluidic elements disposed thereon, and a layer of deformable material covering the fluidic elements. For example, the device can be in the form of a chip or a cartridge.

The cartridge can comprise a cartridge body having a valve body disposed therein, and a flexible or semi-flexible layer bonded to a surface of the cartridge body. The valve is comprised within the combination of the cartridge body and the layer. The valve includes a valve inlet and a valve outlet, typically communicating with fluidic channels. The valve can be closed by pressing the layer against a valve seat of the valve body, thereby obstructing the flow of fluid through the valve. Pressure can be applied mechanically, for example with a ram. The valve can be opened by releasing the pressure against the layer. In certain embodiments, the valve is self-opening. In other embodiments, the valve is initially opened by application of force, for example, forcing liquid through a closed valve. In either case, once open, the layer has sufficient elasticity to pull away from the valve seat without application of external force, such that the valve is biased in an open state. This is also called a "normally open" valve, or a valve open in the "ground state". Such a valve resists closure when negative pressures (e.g., vacuums) are applied through a valve inlet or outlet at pressures typically used to move liquids in mesofluidic or microfluidic devices.

As used herein, the term "nanofluidic" refers to a passage having an aspect no greater than 500 microns. As used herein, the term "microfluidic" refers to a passage having an aspect no greater than 1000 microns. As used herein, the term "mesofluidic" refers to a passage having an aspect no greater than 1500 microns. As used herein, the term "macrofluidic" refers to a passage having an aspect greater than 1500 microns. Ranges between these limits are also contemplated, e.g., between 500 microns and 1500 microns or, greater than 500 microns.

II. Fluidic Device

A. Configuration

Figure 1:
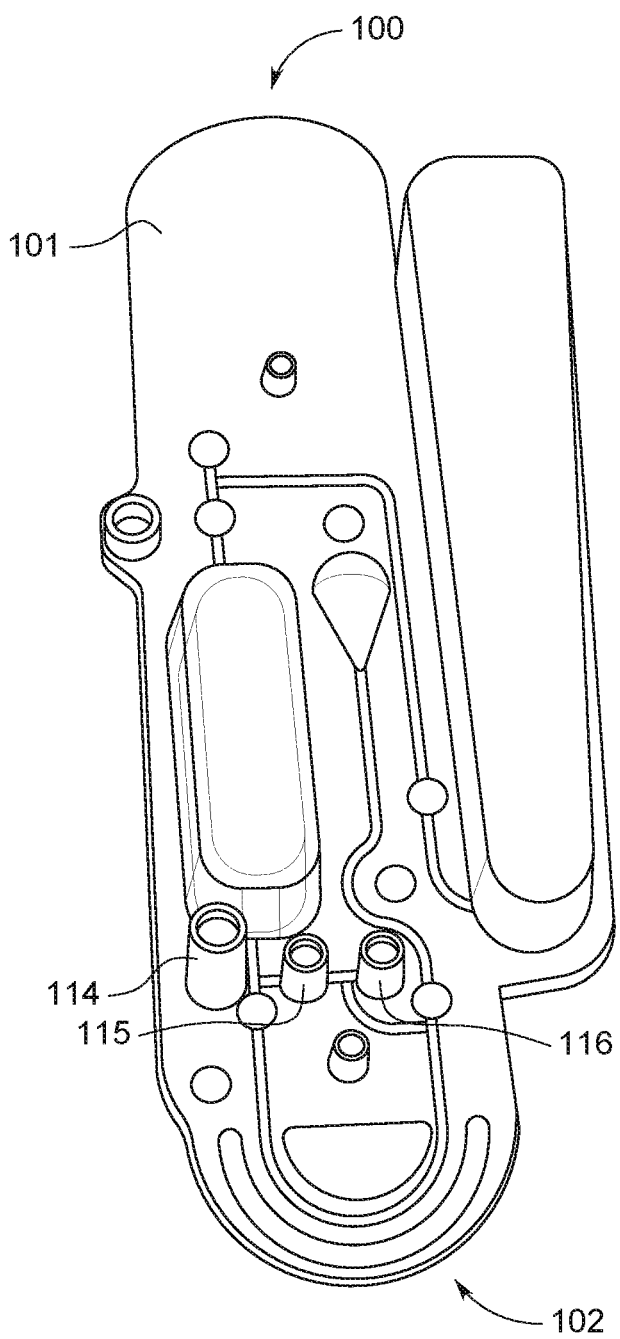
FIG. 1 shows an exemplary cartridge of the disclosure.

Referring to FIG. 1, exemplary cartridge 100 comprises a cartridge body 101 backed by a deformable layer 102. In this embodiment, body 101 is made of injection molded polypropylene. Deformable layer 102 is a layer of heat seal material which is a laminate including a polypropylene layer on a polyethylene backing. Stoppered compartments filled with reagents open on ports 114, 115 and 116.

Figure 2:
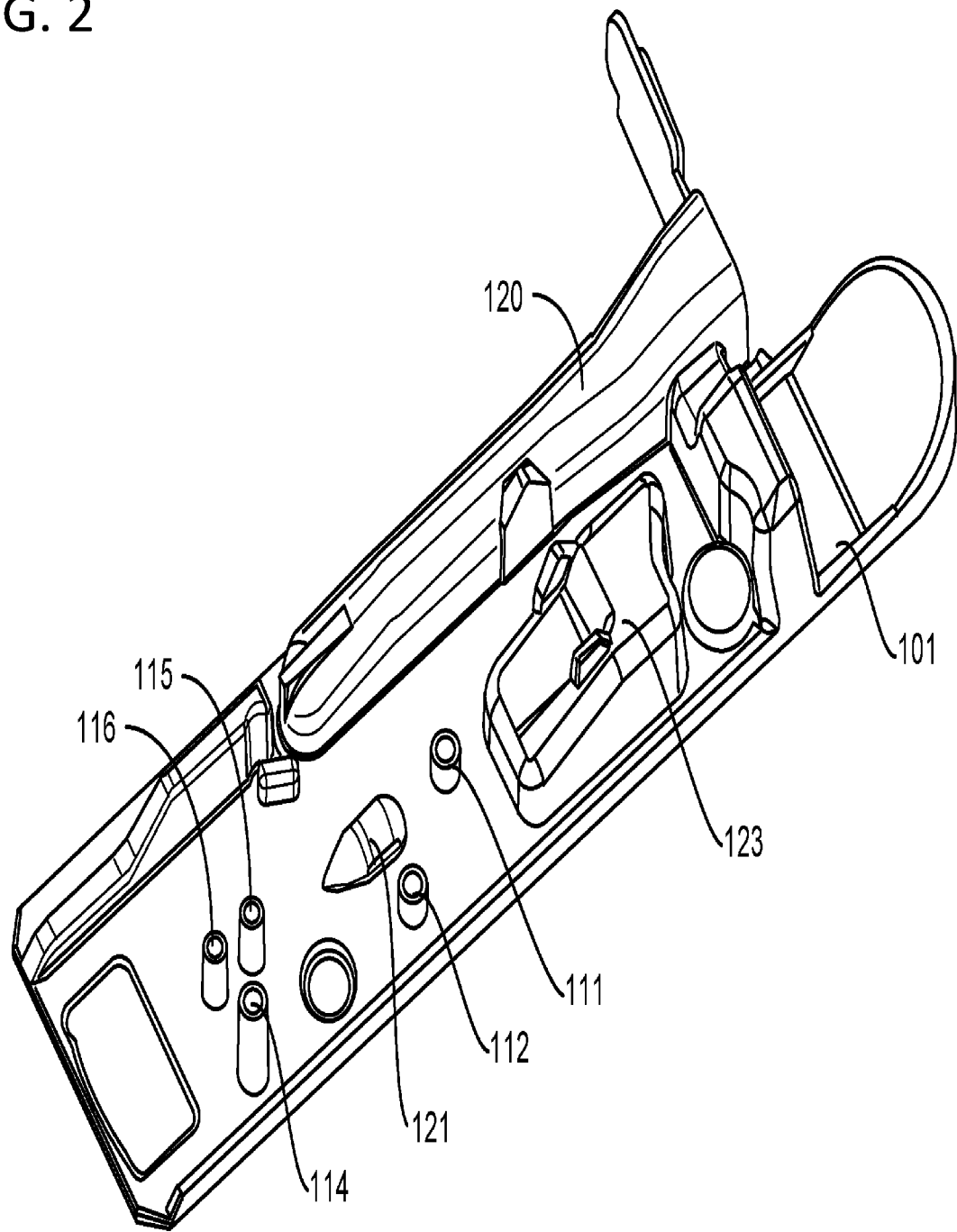
FIG. 2 shows an exemplary cartridge body this disclosure.

FIG. 2 shows a side of body 101, including ports 111, 112, 114, 115 and 116; and walls of chambers 120, 121 and 123. Positive or negative pressure can be applied to the fluidic circuit through port 112 to move liquids in the fluidic circuit.

Figure 8:
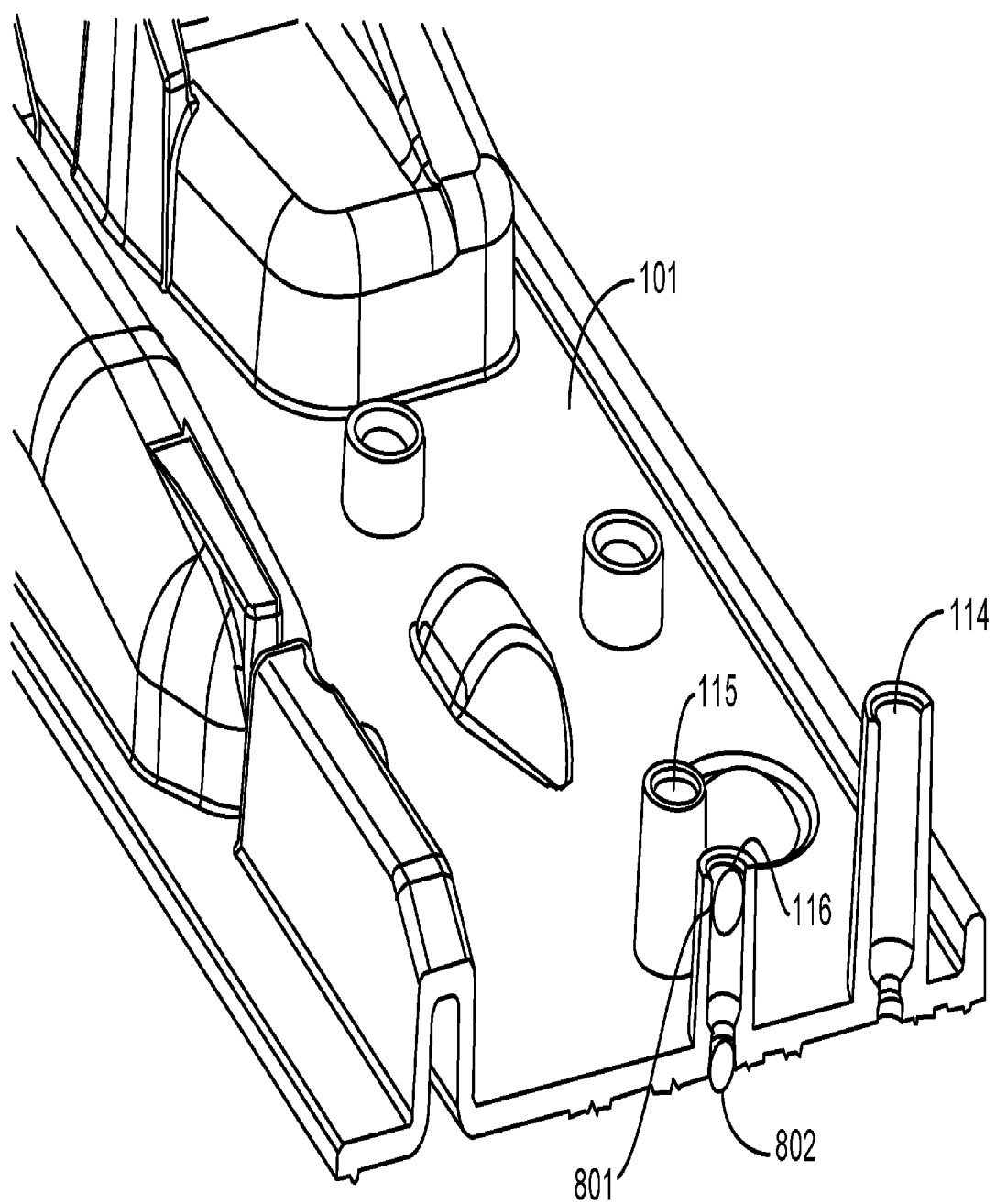
FIG. 8 shows a cutaway view of reagent containers of a cartridge sealed with ball valves.

FIG. 8 shows an exemplary cartridge having ports 114, 115 and 116 configured as chambers communicating with fluidic channels through vias. The chambers are configured to contain reagents and to deliver reagents to a fluidic circuit. The reagent delivery member is shown here as a dual plunger sealed chamber 116 having a first stopper 801 and a second stopper 802, in this case configured as balls. The stoppers 801 and 802 seal a receptacle (e.g., a column or tube of port 116) having a reagent (e.g., premix, master mix), such as an SIR master mix. The application of force to the first stopper ball 801 (such as, e.g., with the aid of a plunger or a syringe) actuates the movement of the second stopper ball 802 ball away from the via, creating a flow path for the reagent to pass into channels 131 and 134.

Figure 3:
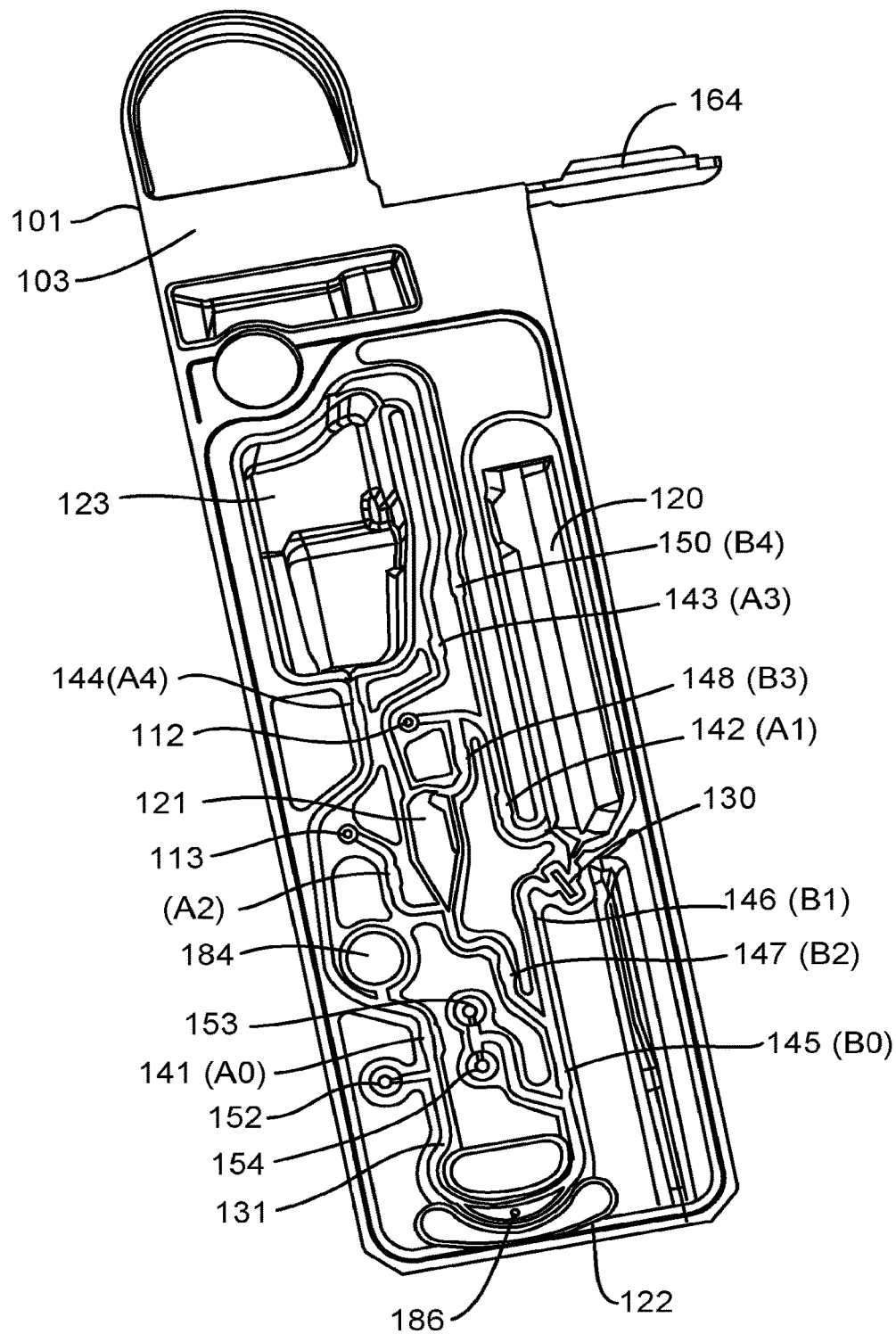
FIG. 3 shows a face of an exemplary cartridge body of the disclosure with elements of a fluidic circuit.

FIG. 3 shows the fluidic side of exemplary body 101. Fluidic elements of the cartridge can be formed on a substrate having a surface that is substantially flat and that defines a plane. Various elements of a fluidic circuit are formed in the surface of the substrate by methods known to one skilled in the art, e.g., injection molding, hot embossing, laser cutting and 3D printing. Elements may be disposed below the plane of the surface, e.g., as channels, wells or chambers, or valve seats. Other elements, such as ridges, can protrude above the plane of the surface.

Cartridge body 101 can include closable cap 164 to close sample/lysis chamber 1120.

Wells formed in the cartridge body create chambers 120, 121, 122, 123 and 130. Cartridges can comprise at least one fluidic circuit which comprises, as elements, at least one fluid inlet, at least one fluid outlet, at least one valve, and at least one compartment, which elements are fluidically connected through fluidic channels. Fluidic elements, such as channels, chambers and valve bodies, typically include depressions in the body surface. A via (a passage from one side of a cartridge body to another) is distinguished from a depression, which is formed in, rather than through, the body. Inlets and outlets can be formed as vias or openings at an edge of the fluidic side of the cartridge, e.g., as the termination of a channel, e.g., into a compartment such as a sample chamber.

Cartridge body 101 can include sample/lysis chamber 120. Sample/lysis chamber 120 is configured to accept a swab, punch, or other sample type. This compartment can also serve as a lysis chamber. To accommodate the swab, punch, or other sample type, it can have a volume ranging from, e.g., 10 pL to 15 ml, e.g., 250 pL to 1 ml. Cells are lysed and analytes, such as DNA, RNA or protein, can be extracted from the swab, punch, or other sample type in this chamber.

Cartridge 101 can include reagent chambers (e.g., 114, 115 and 116) filled with, e.g., nucleic acid size standards (molecules of known sizes), PCR master mix and PCR primers, respectively, and sealed with, e.g., balls (801,802) acting as closures for ball valves. When opened, the reagent chambers come into fluidic communication with fluidic channels in sample cartridge 101, for example, through ports 152 (internal lane standard), 153 and 154 (PCR Master Mix and PCR Primer Mix). Pistons can actuate the ball valves, pushing fluids through the ports and into the channels to which they are connected. Sample cartridge 101 also can include inlet port 112 and output port 113. Upon engagement with the cartridge interface, inlet port 112 and outlet port 113 each engage a fluid line. The fluid line connected to inlet port 112 can be attached to a pressure source, e.g., a syringe, to exert positive or negative pressure to fluidic channels via the inlet port, transporting liquids, such as lysis buffer, water or air, into or out of the cartridge. The fluid line connected to output port 113 can conduct analyte from the cartridge to a sub-system for analyte analysis.

Exemplary cartridge 101 includes pump 184. Pump 184 (e.g., an air pump) is configured as a chamber defined by walls of the cartridge body. Pump 184 is fluidically connected to at least one fluidic channel in the cartridge body. Walls of the pump comprise, at least in part, the malleable material of the cartridge body. Accordingly, the walls can be deformed, for example by mechanical force, increasing pressure in the chamber to pump liquid or air in fluidic channels in fluidic communication with the pump. Pump 184 can be actuated with a plunger or piston that depresses walls of pump 184 and forces, for example, air from the pump body through the fluidic channel to which it is connected. Pump 184 can be used to clear fluid from a fluidic channel. For example, in this embodiment, reagent introduced from port 152 into reaction chamber 122 may leave dead volume in channel 131. Pump 184 can be used to pump this dead volume of reagent into reaction chamber 122.

In some embodiments, the cartridge comprises a filter to filter liquid from a biological sample, such as a cell lysate. One such embodiment is shown in FIG. 3. The exemplary cartridge comprises filter chamber 130 comprising a filter, in a flow path between lysis chamber 120 and reaction chamber 122, and typically between the sample chamber and a first valve, e.g., 146. The filter can be a size exclusion filter having pores no greater than any of 100 microns, 50 microns, 25 microns, 10 microns or 5 microns. The filter can be, for example, a mixed cellulose ester, such as a Millipore™ Membrane Filter. Such a filter can be useful to capture particles that may clog valves or chambers in the flow path. In another embodiment, the filter is included around the outlet of the lysis chamber.

Chamber 121 functions as a mixing chamber. A mixing chamber can have a tapered shape such that air delivered from a channel on a side toward gravity bubbles air toward a side away from gravity.

Chamber 122 functions as a reaction chamber. This chamber can be temperature regulated, for example, to perform PCR. The reaction chamber can serve to capture DNA or house a small amount of lysate for direct amplification. It can also be used for cleanup and amplification. To minimize the duration of thermocycling and the amount of energy required, this chamber should have minimal volume, perhaps ranging from 2 pi to 25 pi, although other configurations are practical.

In one embodiment a fluidic device of this disclosure comprises a reaction chamber that comprises a solid substrate, e.g., solid phase extraction material 186, for retaining analyte from the sample. The solid substrate can comprise a material that binds the analyte, such as a nucleic acid such as DNA. The amount of solid substrate in a chamber can be selected to retain the predefined amount of analyte. For example, the material can be Whatman paper or carboxy-lated particles. Alternatively, the solid substrate can be an absorbent or sponge-like material that absorbs a predetermined volume of fluid. The material can be in the form of a monolith. The material can be, for example, PVDF (polyvinyldiene fluoride) or other membranes, filter paper, glass fiber filters, magnetically attractable particles, chromatography media, solid phase extraction materials, or glass particles. In operation, lysate is pumped through the chamber and a predetermined amount of analyte is retained on a solid substrate. Then, retained material is contacted with reagents, e.g., reagents for PCR. The resulting material can be incubated to form a reaction product. For example, the chamber can be put into thermal contact with a thermal-control device, such as a Peltier, and the reaction mixture can be thermally cycled. In another embodiment, the chamber can include a pocket or container designed to retain a defined volume of liquid. In another embodiment, the chamber can have a surface coating that retains the desired analyte, e.g., an antibody to capture epitopes or a single stranded nucleotide to capture a target nucleic acid. In another embodiment, the chamber could have a coating, e.g., PEG, that will retain a desired volume of liquid.

Chamber 123 functions as a waste chamber. A waste chamber can contain material 185 that degrades nucleic acids, polypeptides, or other analytes. For example a material can comprise a chlorinated material, such as calcium hypochlorite. In another embodiment, the material can comprise an enzymatic activity such as a DNAase, RNAase, protease, etc. Alternatively, the waste chamber can include an absorbent material that absorbs waste containing liquid. In another embodiment the nucleic acid degrading material is contained in a water-soluble capsule. In yet another embodiment the nucleic acid degrading material is combined with an absorbent material such as cellulose or polypropylene fibers.

These functional elements are fluidically connected by fluidic channels, for example, channels 130, 131, 132, 133 and 134. Liquid flow along the channels is regulated by valves. The valves include valve bodies formed in the cartridge body and portions of the deformable layer covering the valve body that can be deformed into the valve body, blocking flow in the fluidic channel. Valve bodies are shown in FIG. 3 at various positions, e.g., 141-149. More specifically, these valves include vent valve 141, waste vent valve 142, product top valve 143, product bottom valve 145, lysis valve 164, lysis transfer valve 147, cycler in valve 148, cycler out valve 149, product out valve 144.

Cartridge body 101 includes the following valve bodies: 141 Cycler Out (A0), 142 Lysis (A1), 143 Waste Shut Off (A3), 144 Waste In (A4), 145 Cycler In (B0), 146 Lysis Transfer (B1), 147 Product Bottom (B2), 148 Product Top (B3) and 150 Vent (B4).

The valve is configured so that after initial closure and removal of the closing force, the valve is biased open (e.g., "normally open"). This characteristic is a function of the valve geometry and the properties of the deformable layer. In general, the deformable layer is attached to the valve body at a position that is above the bottom or floor of the valve. In this configuration, a deformable material that undergoes elastic, but not plastic, deformation upon valve closure will return to a position that leaves the valve open after the deforming force is relieved. In situations typical of fluidic devices in microscale or mesoscale range, this may be the case for elastomeric materials such as PDMS. However, materials such as heat seal, used as a deformable material in some embodiments of a cartridge, are expected to undergo both elastic and plastic deformation when deformed into a closed valve position. In this case, the valve geometry can be selected such that after deformation on valve closure, the material retains sufficient elasticity so that after release of pressure closing the valve, the deformable material returns to a shape that leaves the valve biased open.

Figure 4:
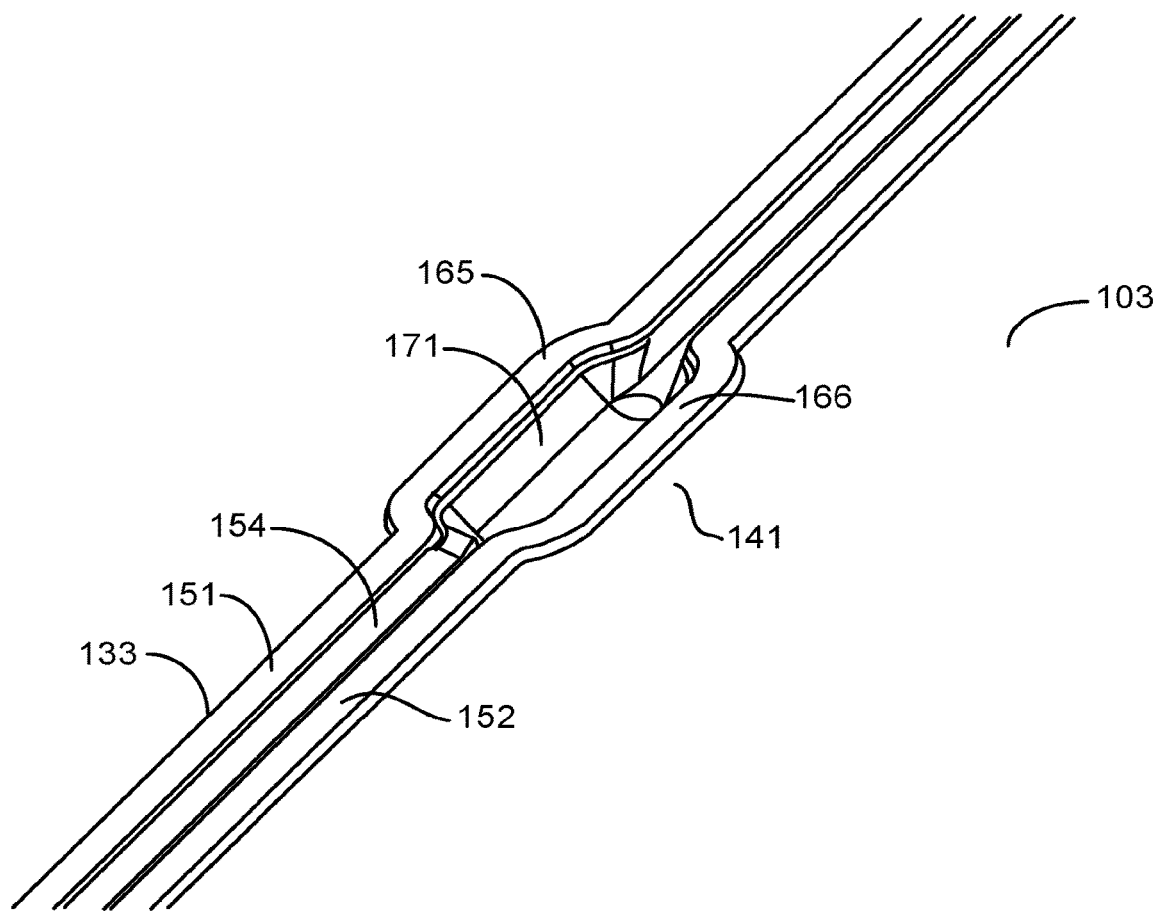
FIG. 4 shows an exemplary valve body of this disclosure.

FIG. 4 is a detailed view of a valve body, e.g., element 141. Fluidic channel 133 includes raised ridges 151 and 152. These ridges are raised above the plane (i.e., away from the body) of the generally flat surface 103 of the fluidic side of the cartridge body 101. Furrow 154 of channel 133 forms a recessed channel in surface 103 of the fluidics side, that is, disposed below the plane (i.e., into the body) of surface 103. In certain embodiments, valve bodies do not have valve reliefs flanking the channel walls. A valve with deformable material attached is shown, e.g., in FIG. 5.

In another embodiment surface 103 can comprise a well positioned near the valve body. Such a well can be used as a guide for a pin to provide coarse alignment of the ram head before depressing the ram head into the valve body.

Materials for the cartridge body and the deformable layer are selected which can be deformed by pressure exerted by the source of positive pressure, e.g., a mechanical ram. Typically, the deformable layer has the ability to stretch under pressure, and the valve body has the ability to compress or flow under pressure. In this way, concentrated pressure can be exerted against the valve sufficient to compress portions of the valve body without breaking (e.g., cracking or piercing) the deformable layer. Combinations of materials for the cartridge body and the deformable layer include, for example, polypropylene and heat seal, polyethylene and laser-welded polyethylene and Teflon and aluminum foil bonded with a patterned adhesive.

In order to initially close the deformable layer against the valve seat, the ram applies an appropriate pressure against the deformable layer in the appropriate position. In certain embodiments, valve bodies have a cross section that progressively narrows toward the bottom of the depression forming valve seat of the valve body.

Several factors can be considered in configuring the valve. In certain embodiments, as regards the aspect ratio of the cross-section (width:depth), the valve body has sufficient depth such that the bottom of the valve body is disposed deeper in the valve body than the points of attachment of the malleable layer. In fact, the deformable layer may be attached at a point on a ridge disposed above the plane of the surface of the cartridge body. In this configuration, a deformable layer of heat seal will experience elastic and plastic deformation when initially depressed, but retain sufficient elasticity to return, at least partially, to its original shape, leaving an aperture in the valve. Accordingly, the valve, in its ground state, is normally open, or biased toward open. In this configuration, the aperture is sufficiently large to allow passage of particulate material in a liquid sample passed through it.

In other embodiments, the valve is configured so that the deformable layer retains sufficient elasticity to resist valve closure when negative pressure (e.g., suction) is exerted on a fluidic channel communicating with the valve. For example, the valve can resist closure upon application of negative pressures up to about 10 psi.

The aspect ratio (width:depth) of the valve body can be between about 1:1.5 and about 1:0.1, e.g., about 1:1.2 to about 1:0.7.

Valve bodies of the devices of this disclosure typically have a diameter between about 0.2 mm (200 microns) and about 2 mm.

In certain embodiments, valve body is not so narrow (which is to say, does not have an aspect ratio (width:depth) that is so small) that the deformable layer breaks (e.g., tears or is punctured) when pressed against the valve body by a mechanical ram. The appropriate depth can be determined by the ordinarily skilled artisan based, in part, on the pliability of the deformable layer.

In another embodiment, the valve body has walls having a configuration to provide a centering action against a ram pressed against deformable layer on the valve body. The ram may be off-center with respect to the center line of the valve body in cross section. This configuration can be useful if the size of the valve is sufficiently small that there is little tolerance for the ram head to be off-center with respect to the valve body.

In one aspect, lines drawn tangent to level points of opposing walls of the valve body at any point between the top and bottom of the valve body form an angle between any of at least 30°, at least 45° or at least 60° and any of at most 150°, at most 125° or at most 100°.

The valve body can have depth, from its bottom to the height of the top of a ridge (if present) or a plane generally defined by the cartridge body surface of between 50 microns and 200 microns, e.g., about 100 microns.

Many valve geometries are consistent with the use of heat seal as a deformable material. In one embodiment, the diameter of the valve body decreases with increasing depth. However, the aspect ratio of the valve should not be so narrow that closure of the valve results in failure of the deformable material, such as piercing or tearing. In another embodiment, the valve body and the ram have shapes such that closure of the valve produces a pressure that is normal to the surface of the valve body across all areas of the valve cross section. In some embodiments, this normal pressure is exerted when the pressure of the ram is unidirectional, e.g., only in a vertical direction or normal to the plane defined by a surface of the cartridge body into which the valve is disposed.

Within these parameters, the cross-section of the valve body can take a variety of shapes. In one embodiment, the cross section is substantially wedge shaped (e.g., a triangle with a curved radius at the bottom, e.g., with a blunt rather than sharp point at the end). In another embodiment cross-section takes the shape substantially of a catenary or a parabola. In another embodiment, the cross-section is substantially circular. If the cross section of the valve has the shape of a cord of a circle, the included angle of the chord can be between about 30° and 60°.

In an exemplary fluidic device, the body can comprise a polymer, e.g., polymer is a polycarbonate, an olefin co-polymer (COC) (e.g., Zeonor), a cycloolefin co-polymer (COP), an acrylic, a liquid crystal polymer, polymethylmethoxyacrylate (PMMA), a polystyrene, a polypropylene, or a polythiol. The deformable layer can comprise a siloxane, such as PDMS. The deformable layer can be bonded to the body by coating the body surface with hydroxyl groups and binding the deformable layer through the oxide groups. In one embodiment, the polymer body is coated with an oxide, e.g., a metal oxide (e.g., aluminum oxide or titanium oxide) or a semiconductor oxide (e.g., silicon oxide or germanium oxide). Such bonding is described in, for example, U.S. Pat. No. 8,584,703.

B. Materials

1. Cartridge Body

The body can have an external surface comprising elements of fluidic circuits, such as channels, compartments, vias, and valve seats. The body can be made by injection molding of the thermoplastic, 3D printing or other methods well known to one skilled in the art. These features can be covered with a layer of deformable material attached to the surface of the cartridge body. The layer can function to seal otherwise open features such as channels and compartments. The layer of deformable material can deform to contact a valve seat, thereby closing the valve.

The material can be attached to the surface of the body using a selective bonding process in which the material bonds to selected portions of the surface during the bonding process and does not bond to un-selected portions of the circuit after the bonding process is complete. For example, the material may bond to surfaces other than fluidic elements during the bonding process, and not bond to fluidic elements, such as channel floors, chamber walls and valve seats, after the bonding process. Methods for selective bonding include, for example, thermal bonding (e.g., heat sealing, welding, laser welding), chemical bonding (e.g., chemical bonding of oxide to PDMS, vapor bonding) and selectively placed adhesives (adhesive bonding). In certain embodiments, bonding is not thermal bonding and/or is not chemical bonding and/or is not adhesive bonding.

In one embodiment a layer of the deformable material is attached to a surface of a cartridge body through thermal bonding. This can include thermally bonding the material directly to the surface, or thermally bonding the material through an intermediate layer of material. In the latter case the material can be a laminate in which a deformable material is coated with a layer of material that contacts the surface and that melts at lower temperature than the deformable material. In either case bonding typically comprises contacting the layer of deformable material to the body to form a combination and using a die to apply heat and pressure to the combination. Application of heat and pressure melts substrates in locations at which the material and body are in contact and fuse them, e.g., through coalescence. This process is more generally referred to as welding.

At least the valve body of the cartridge body can comprise a malleable material, that is, a material capable of plastic deformation. The material, after being deformed, does not return to its original shape. In certain embodiments the malleable material is a plastic, a wax or a soft metal (e.g., lead). The plastic can be, for example, a thermoplastic, a thermoset, a single component resin or a multi-component resin. In one embodiment, the cartridge can comprise an injection molded body, for example, a thermoplastic, and a deformable layer bonded to the body. The thermoplastic can include any thermoplastic known to those skilled in the art, such as polypropylene, polystyrene, polyethylene, polyethylene terephthalate, polyester, polyamide, vinyl, poly(vinylchloride) (PVC), polycarbonate, polyurethane, polyvinyldiene chloride, cyclic olefin copolymer (COC), or any combination thereof.

2. Layer of Deformable Material

The layer of deformable material (also called a "deformable layer") used in cartridges disclosed herein can comprise a plastic material (plastic deformation) or an elastic material (elastic deformation). The plastic material can comprise, without limitation, a polymer or a metal. Suitable plastic materials for the layer of deformable material include, without limitation, polypropylene and polyethylene. Suitable metals include, for example, aluminum. Suitable elastic materials include, for example, elastomeric materials such a polysiloxanes, e.g., PDMS. Other deformable materials are further described herein. In certain embodiments, the deformable material is not an elastomeric material. As used herein an "elastomer" or "elastomeric material" is a material, such as a natural rubber or a synthetic rubber (e.g., a silicone (such as PDMS) or Santoprene), having a low Young's modulus. Such materials, used in the microvalve configurations described herein, undergo elastic, but not plastic, deformation.

A material that bonds to a body through application of heat and pressure is referred to herein as a "heat seal". Heat seals are well known in the art and are commercially available. For example, 4titude (Wolton, Surrey, UK) commercializes a variety of heat seals. These heat seals are described on the www website 4ti.co.uk/sealing/heat-seals/. These include, for example, Clear Seal, Clear Weld Seal, and Foil Seal. Heat seals also are produced by Axygen, a Corning brand (Corning, Tewksbury, Mass., USA). These include Axygen® PlateMax heat sealing film and sealing film rolls. See the website: catalog2.corning.com/Life-Sciences/en-US/Shopping/
Product.aspx?categoryname=Genomics+and-i-Proteomics (Lifesciences)%7cPCR+Products(Lifesciences)
%7cSealing+Films-i-and-i-Tapes-i-for-i-Microplates
(Ufesciences)%7cHeat+Sealing+Films-i-and-i-Tapes-i-for-i-Microplates(Lifesciences). Such materials exhibit partially elastic properties, that is, their deformation is partially reversible.

The deformable material can be a homogenous or non-homogenous material. In certain embodiments, the heat seal material is made from the same material as the body of the cartridge. It can comprise a thermoplastic (e.g., polypropylene, polyethylene, polystyrene, cycloolefin co-polymer (COC), mylar, polyacetate) or a metal (e.g., aluminum). See, e.g., WO 2012/136333. The heat seal can be produced by contacting a heat seal layer with the body and applying heat and pressure. Non-homogenous films include laminates having a first side for contact with the heater and a second side for contact with the body. The first side has higher melting temperature ("high melt") than the second side ("low melt"). This permits use of a heat source to bring the second side to its melting temperature before the first side allowing bonding to the body without bonding to the heater.

III. Method of Making

FIGS. 5A-5D show the attachment of a layer of deformable material to the fluidics face 103 of cartridge body 101 and the formation of a closed valve. FIG. 5 depicts a cross-section of valve 141.

Figure 5A:
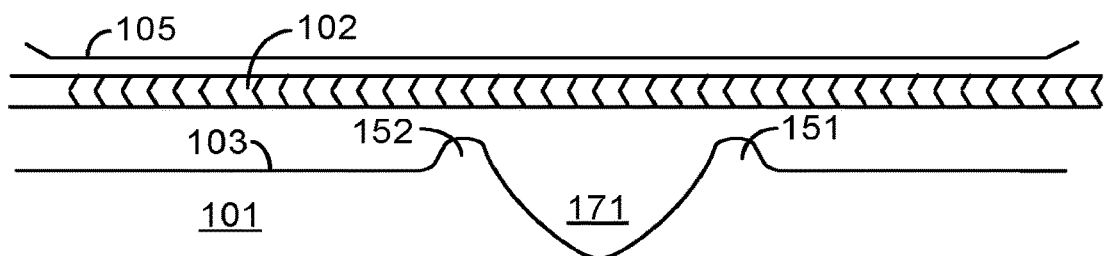
FIGS. 5A-5D show an exemplary formation of a valve of this disclosure.

FIG. 5A shows cartridge body 101, heatable die 105 and laminated seal 102 sandwiched between them. Cartridge body 101 includes surface 103, ridges 151 and 152 (optionally), and groove 171. This figure also shows that ridges 151 and 152 are formed as areas raised against the planar surface 103, while groove 171 is formed as an area depressed or recessed against the plane of surface 103.

Ridges can be between about 25 microns and about 100 microns above the plane of the surface of the cartridge that mates with the deformable layer, e.g., about 50 microns. The groove of the valve body can have a depth below the plane between about 50 microns and about 300 microns. If the deformable layer is attached by a method other than heat sealing, e.g., with a patterned adhesive or with laser welding, then the ridges do not need to rise above the plane of the surface. Fluidic channels that are either microfluidic, that is, having an aspect less than 500 microns) or macrofluidic, that is, having no aspect less than 500 microns (e.g., having no aspect less than 1000 microns). Fluidic channels can have a depth of about 100 microns to about 400 microns.

The layer of deformable material 102 is bonded to cartridge body 101 by pressure and heat applied by die 105. The layer of deformable material 102 is, in this example, a laminate. One side of the laminate contacts the die. This side has a melting temperature higher than the temperature of the die. Therefore, when the heated die is pressed against the deformable material 102 the higher melting side does not melt or stick to the die surface. The other side of the laminate contacts surface 103 of cartridge body 101 and has a melting temperature lower than the temperature of the die. Accordingly, this material melts when the heated die is applied. The cartridge body also comprises a malleable material that melts when pressed against the heated die.

Figure 5B:
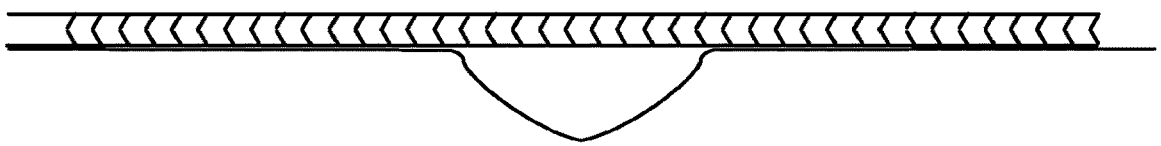

Consequently, as shown in FIG. 5B, after application of pressure and heat by the die, ridges 151 and 152 are compressed or crushed. Also, the layer of deformable material is selectively bonded to the cartridge body, in this case, to surface 103 and to areas of attachment on the valve body, e.g., to ridges 151 and 152. Through this bonding the deformable layer seals fluidic elements of the fluidic circuit, including ports, chambers, channels and valves.

Figure 5C:
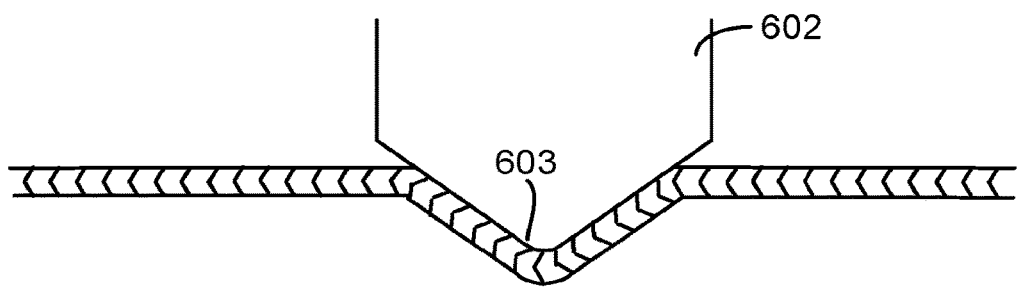

FIG. 5C shows closing of the valve in cross-section. Ram head 602 has a shape that conforms substantially with the shape of groove 171.

The oblong shape of the valve body allows for the ram head to be shifted along the axis depicted by the circle X. Accordingly, in an instrument in which a plurality of rams in a cartridge interface must be aligned with a plurality of valves in a cartridge engaged with the interface, flexible rams and the self-centering action of the groove provide greater tolerance for the relative positioning of rams and valves.

The pressure of the ram presses the layer of deformable material against the valve body and, in an initial application, stretches the deformable material causing plastic deformation of the deformable layer. This coins or stamps the valve body into a closed or closable position. However, the valve body is configured with a shape such that, even after stretching, the deformable material retains some elasticity. For this purpose, the layer of deformable material must have a strength (e.g., yield strength or ultimate strength) that is greater than the strength of the ridges, such that pressure from the ram crushes the ridges but does not break the deformable layer. In this configuration the valve is closed and no liquid can pass through the valve.

Figure 5D:
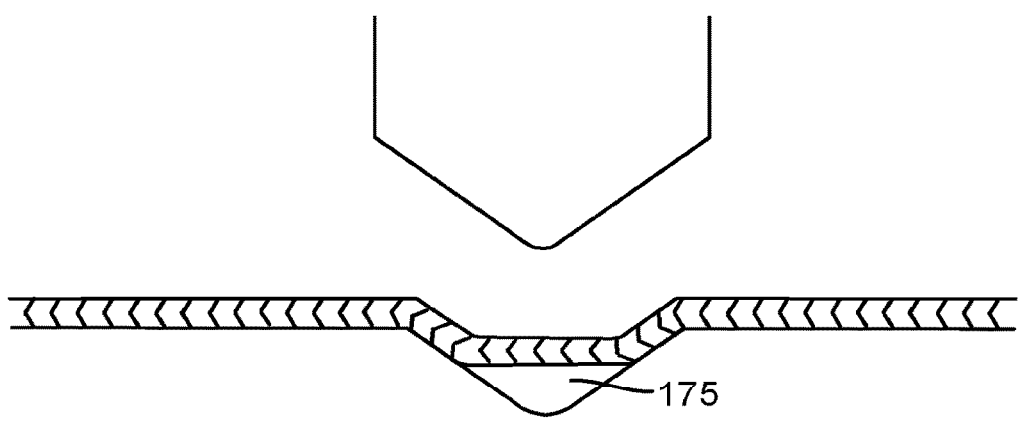

Referring to FIG. 5D, to open the valve to allow the passage of liquid, the ram is retracted from the cartridge. The deformable layer is bonded to the remains of the ridges, to the edges of the valve body or to upper parts of the wall of the valve body. But the deformable material is not bonded to the floor of groove 171. Due to the slope of the walls of the valve body, the deformable layer retains sufficient elasticity to "spring back" from the floor of the groove. This produces a passage 175 through the valve through which liquid can pass. Thus, there is formed a valve that is biased open after pressure in the channel is released. To close the valve, ram head 602 is pressed against the layer of deformable material, actuating the layer of deformable material against the valve seat and closing the passage, as shown in FIG. 5C. Accordingly the valve seat comprises those portions of the valve body with which the deformable material comes into and out of contact.

Form and function of the valve improve when the ram head is centered with respect to the valve body. Such an orientation promotes a tight seal between the malleable material and the valve body. In certain embodiments the ram and valve exhibit a self-centering action. The ram can be mounted on a pivot or have a flexible or swingable shaft that allows for lateral displacement of the ram as is it pressed into the valve body. When the walls of the valve body are sufficiently steep, a ram pressed against the deformable material overcomes the force of friction to slide toward the valve body midline. Alternatively, the ram can include a centering arm configured to fit in a centering well or depression in the cartridge body. Such a centering arm can provide coarse centering for the ram head against the valve body.

Figure 6:
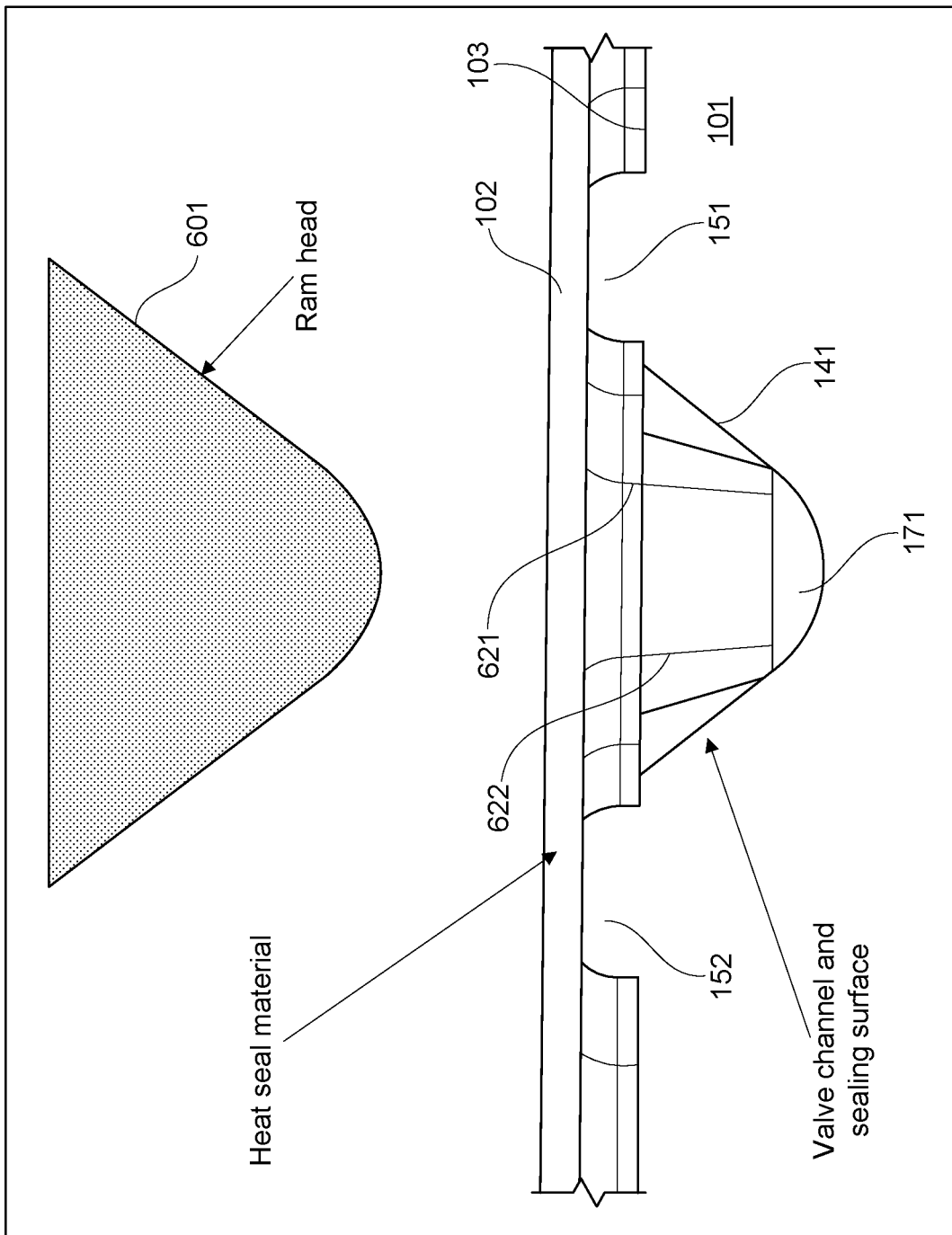
FIG. 6 shows an exemplary ram head this disclosure in cross-section oriented toward a valve body, also shown in cross-section.
Figure 7:
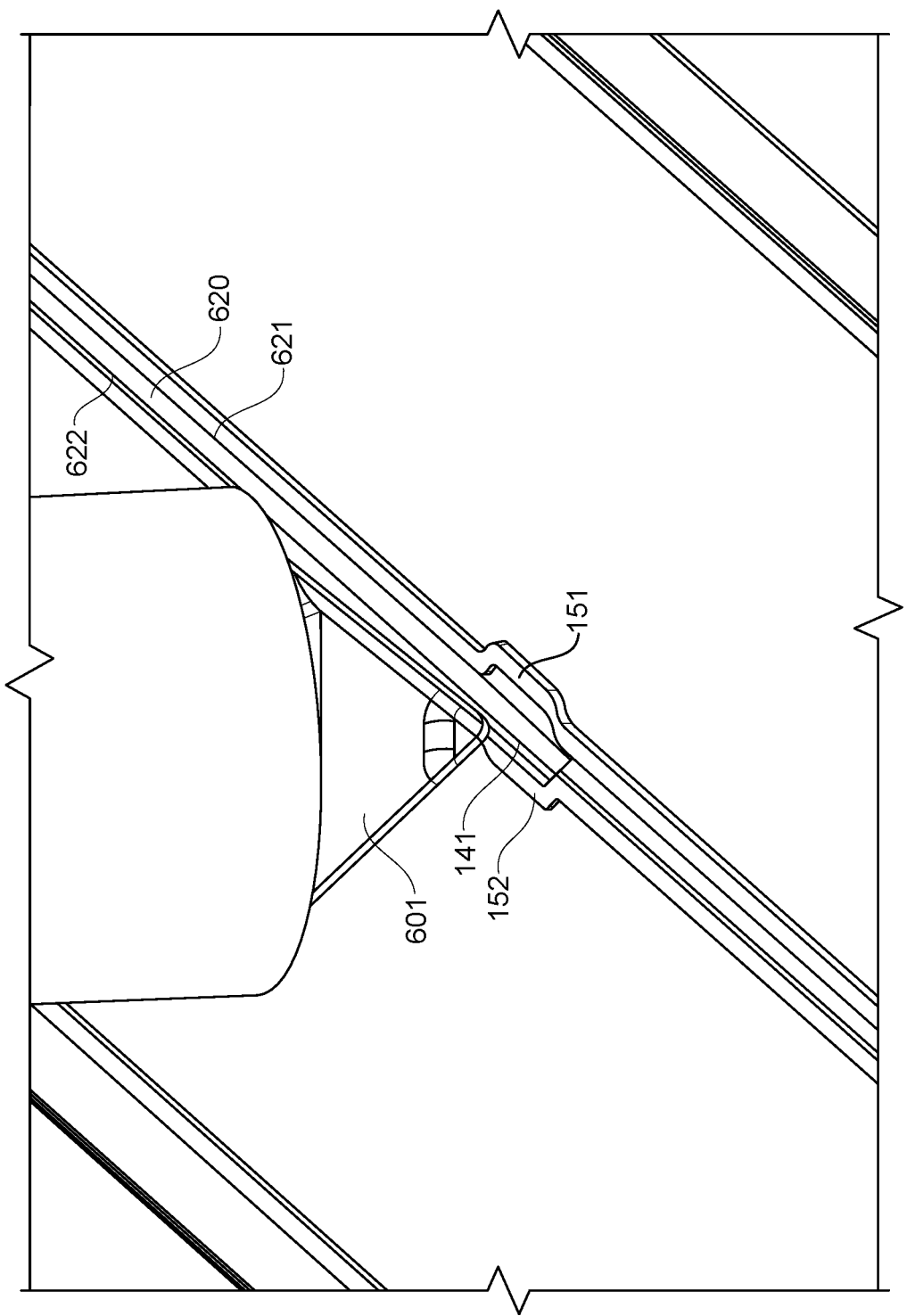
FIG. 7 shows an oblique view of a ram head positioned against a valve of this disclosure. The ram is mounted on a rocker arm to provide play allowing a centering action when the ram is depressed against the valve.

Valves are closed by use of force applied by a ram. FIG. 6 shows an embodiment of the head of ram 601 having a wedge shape that conforms substantially to the shape of valve body 141. Ridges 151 and 152 protrude above the plane of surface 103. Heat seal material 102 overlays the cartridge body. A fluidic channel into which the valve leads is depicted by lines 621 and 622. FIG. 7 shows ram head 601 oriented against valve body 141 in oblique view. Valve body 141 includes raised ridges 151 and 152. Channel 620 also includes raised ridges 621 and 621 which can promote bonding of the deformable layer and sealing of the channel and the valve.

Figure 14:
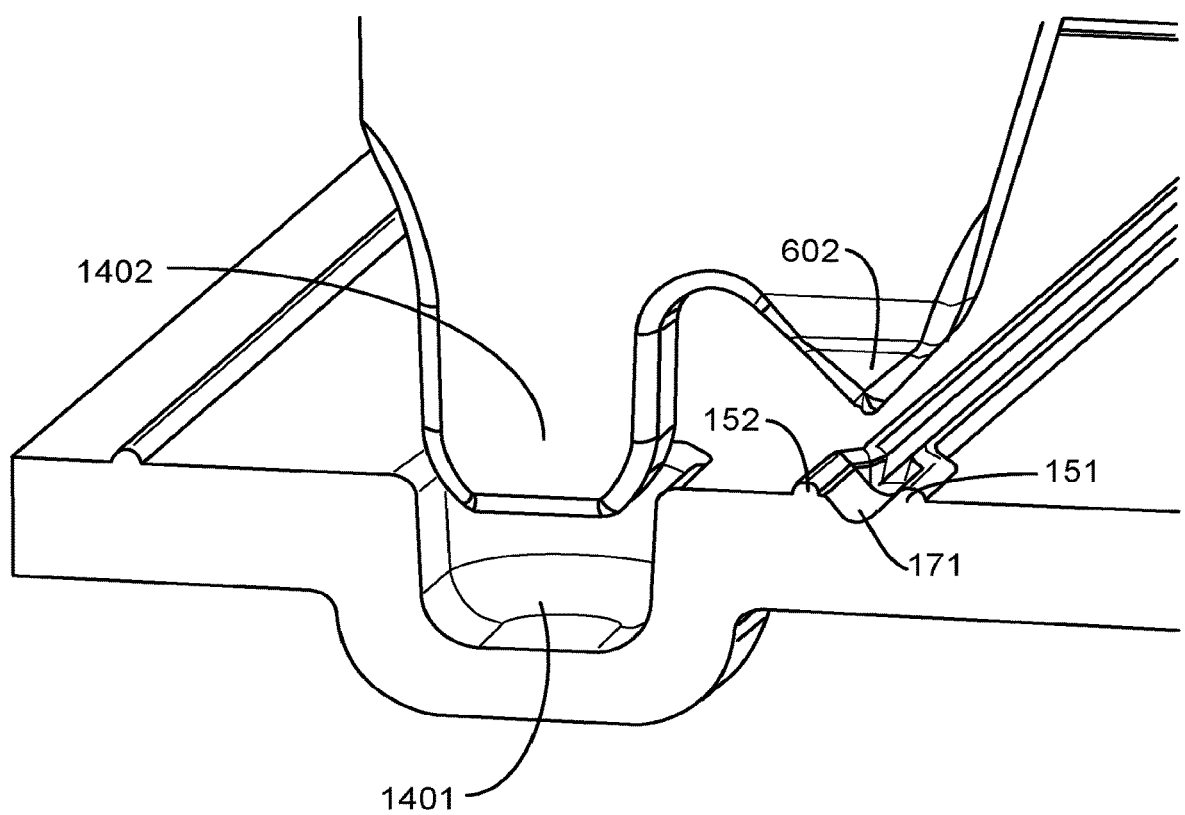
FIG. 14 shows an exemplary valve/ram combination.
Figure 29:
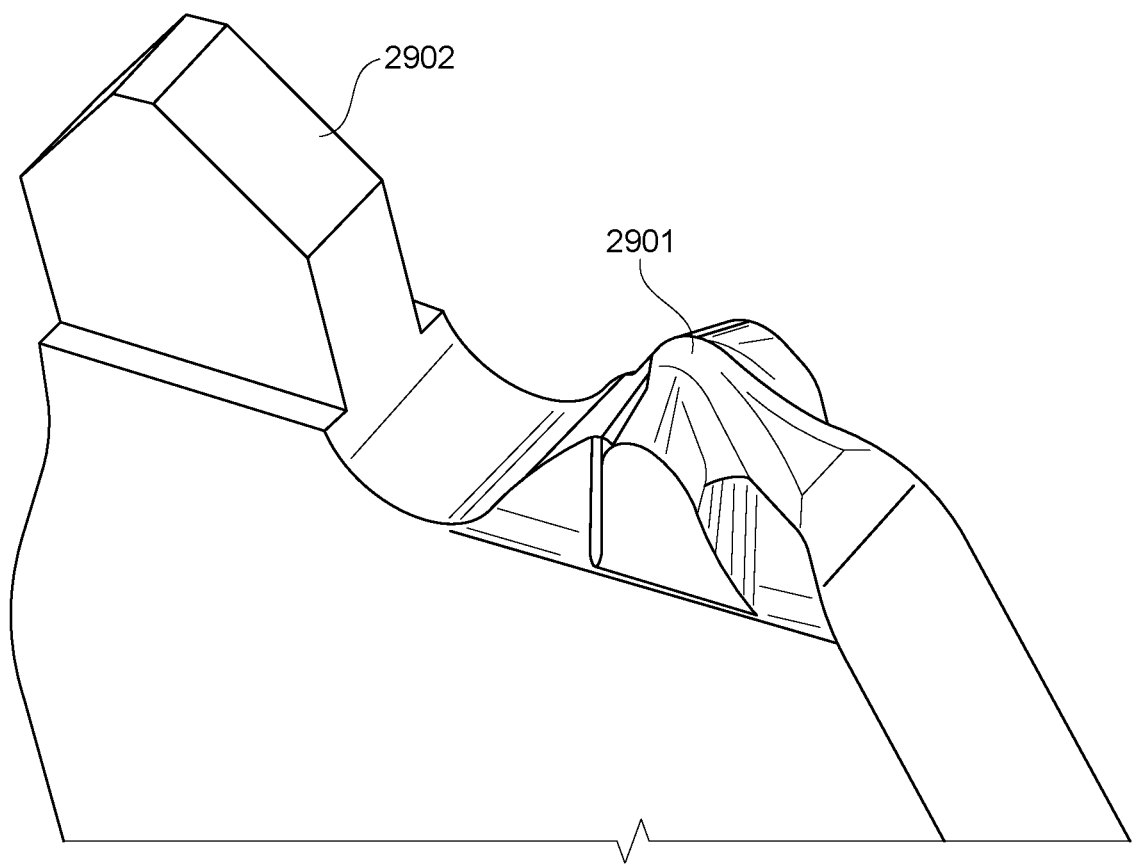
FIG. 29 shows an alternate exemplary ram of this disclosure.

FIG. 14 shows an exemplary valve/ram combination. Centering guide 1402 has a tapered head and mates with well 1401 to provide coarse centering for ram head 602 into a valve body defined by ridges 151 and 152 and furrow 171. This configuration can be used with the ram actuation assembly depicted in FIG. 15, FIG. 16 and FIG. 17. FIG. 29 shows an alternative exemplary embodiment of a ram. Ram head 2901 closes a valve of this disclosure. Ram head 2901 includes wings disposed lateral to the valve and in line with the flow path. These protrusions function to reduce stress on the valve and tearing of the deformable material. Centering guide 2902 has a tapered head for mating with a centering well.

Figure 9:
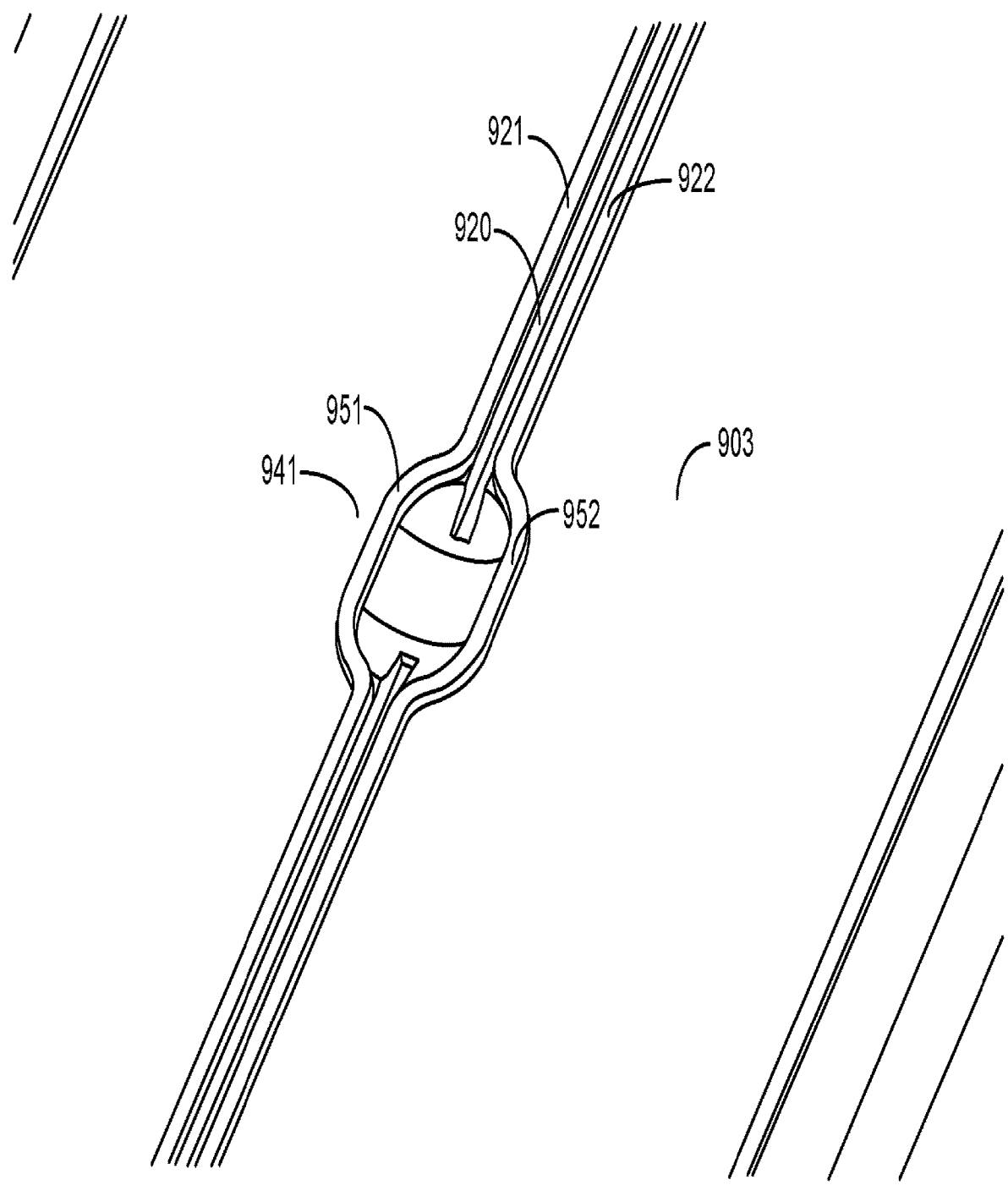
FIG. 9 shows an exemplary valve body of this disclosure.
Figure 10:
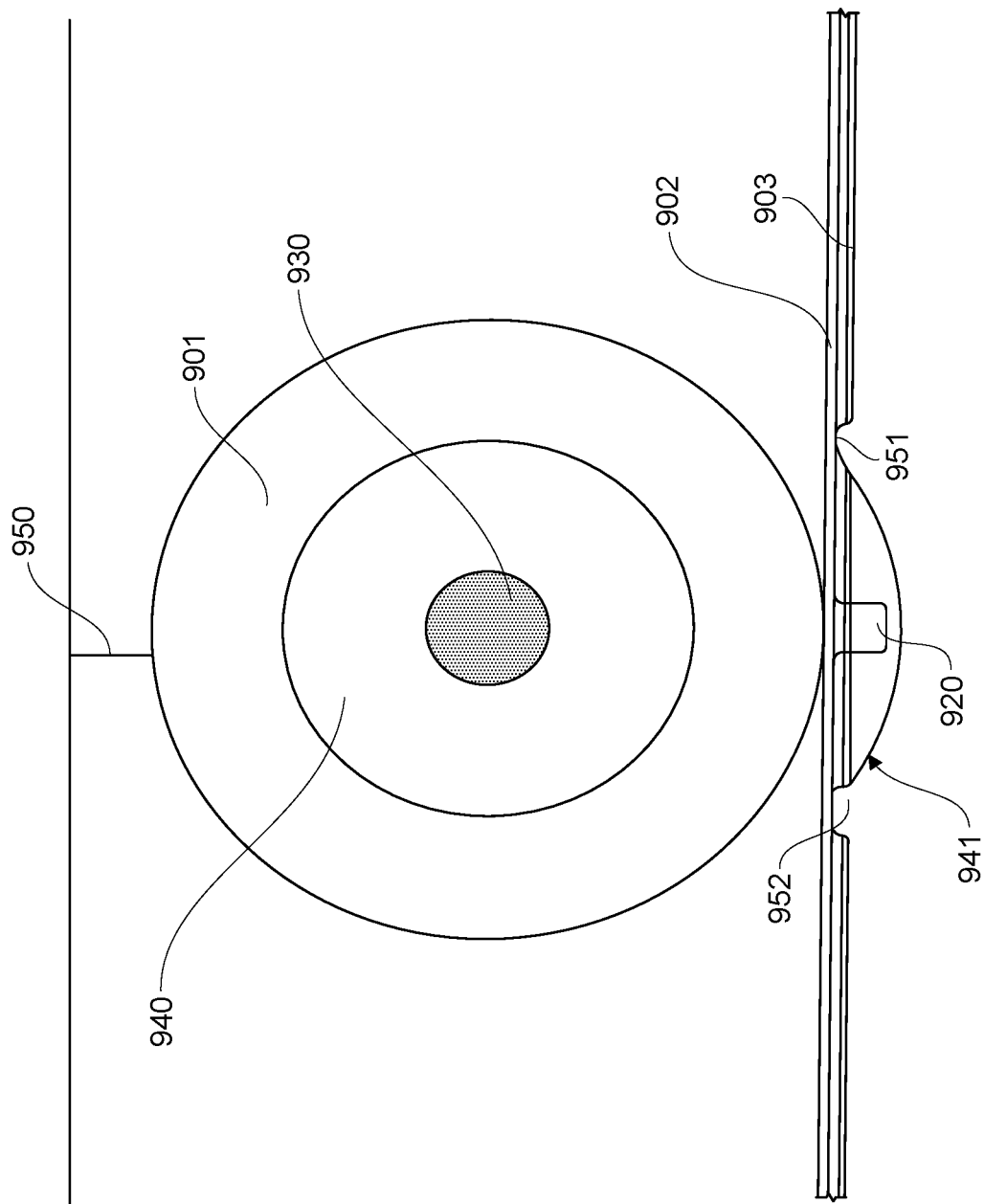
FIG. 10 shows an exemplary ram head this disclosure in cross-section oriented toward a valve body, also shown in cross-section.
Figure 11:
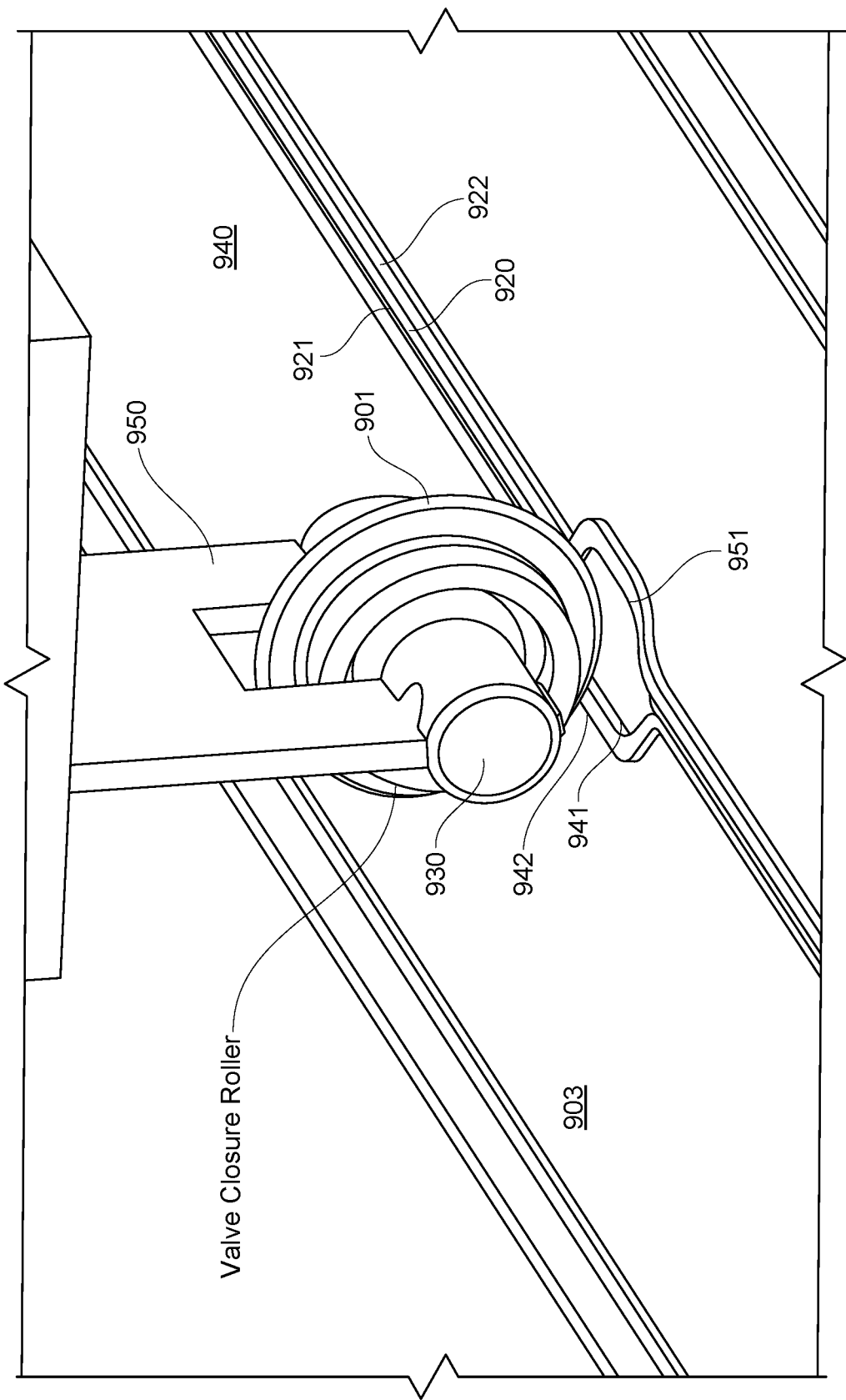
FIG. 11 shows an oblique view of a ram head positioned against a valve of this disclosure.
Figure 13A:
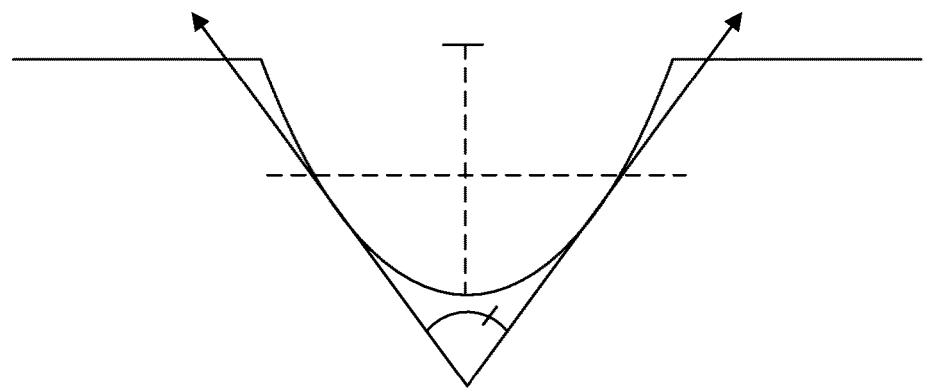
FIG. 13A and FIG. 13B show two exemplary valve bodies. Tangent lines to the walls of the valve bodies are drawn at points half way between the top and the bottom of the valve bodies. The angle formed from the tangent lines in the valve body of FIG. 13A is about 60 degrees, while the angle formed from the tangent lines in the valve body of FIG. 13B is about 130 degrees.
Figure 13B:
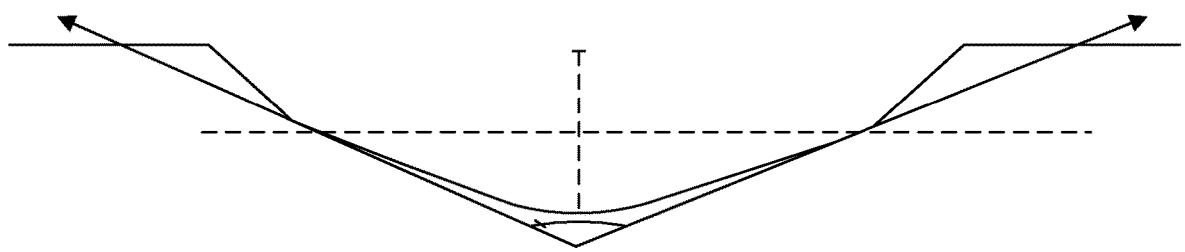

In another embodiment, friction of the deformable material against centering by the ram is overcome by providing a ram having a head in the form of a rotatable wheel. The valve body can have a cross-sectional shape that conforms to the shape of the wheel, such as substantially circular. Such an embodiment is shown in FIG. 9, FIG. 10 and FIG. 11. Valve body 941 Includes ridges 951 and 952 which protrude above the plane of surface 903. A fluidic channel 920 into which the valve leads also includes raised ridges 921 and 922. Heat seal material 102 overlays the cartridge body. The shape of the ram head conforms substantially to the shape of the valve body. FIG. 10 shows a cross-section of a wheel-shaped ram disposed over a valve body. Ram head 901 is configured as a wheel mounted on spindle 930 and rotatable by use ball bearing 940. Ram 950 on which the ram head is mounted comprises a centering spring to allow the ram to move laterally and to be centered in the valve body. FIG. 11 shows ram head 901 oriented against valve body 941 in oblique view. As the ram is pressed into the valve body, the wheel rolls toward the centerline, producing a tight seal.

IV. Cartridge Interface and Operation

Figure 15:
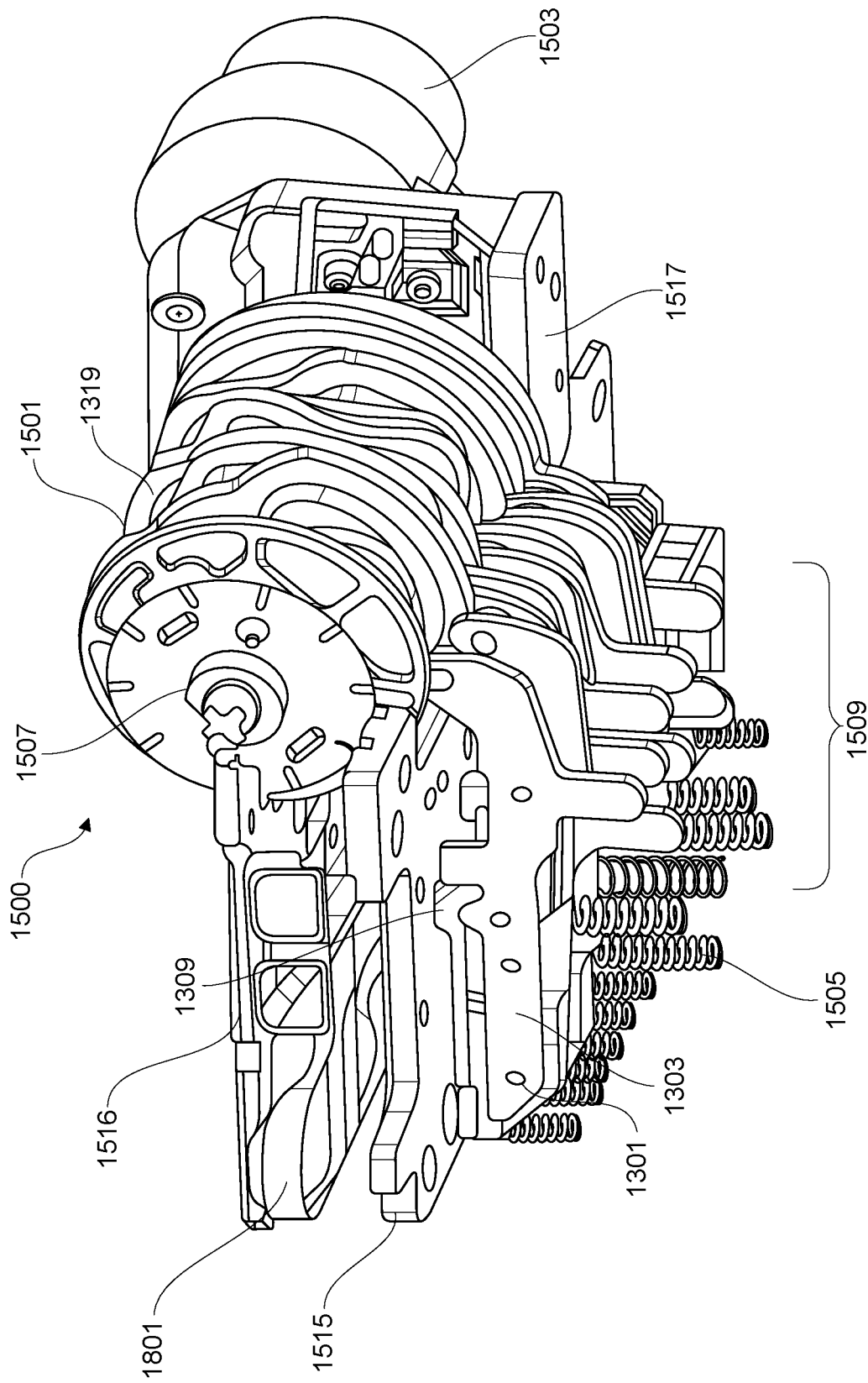
FIG. 15 shows a cam array.
Figure 16:
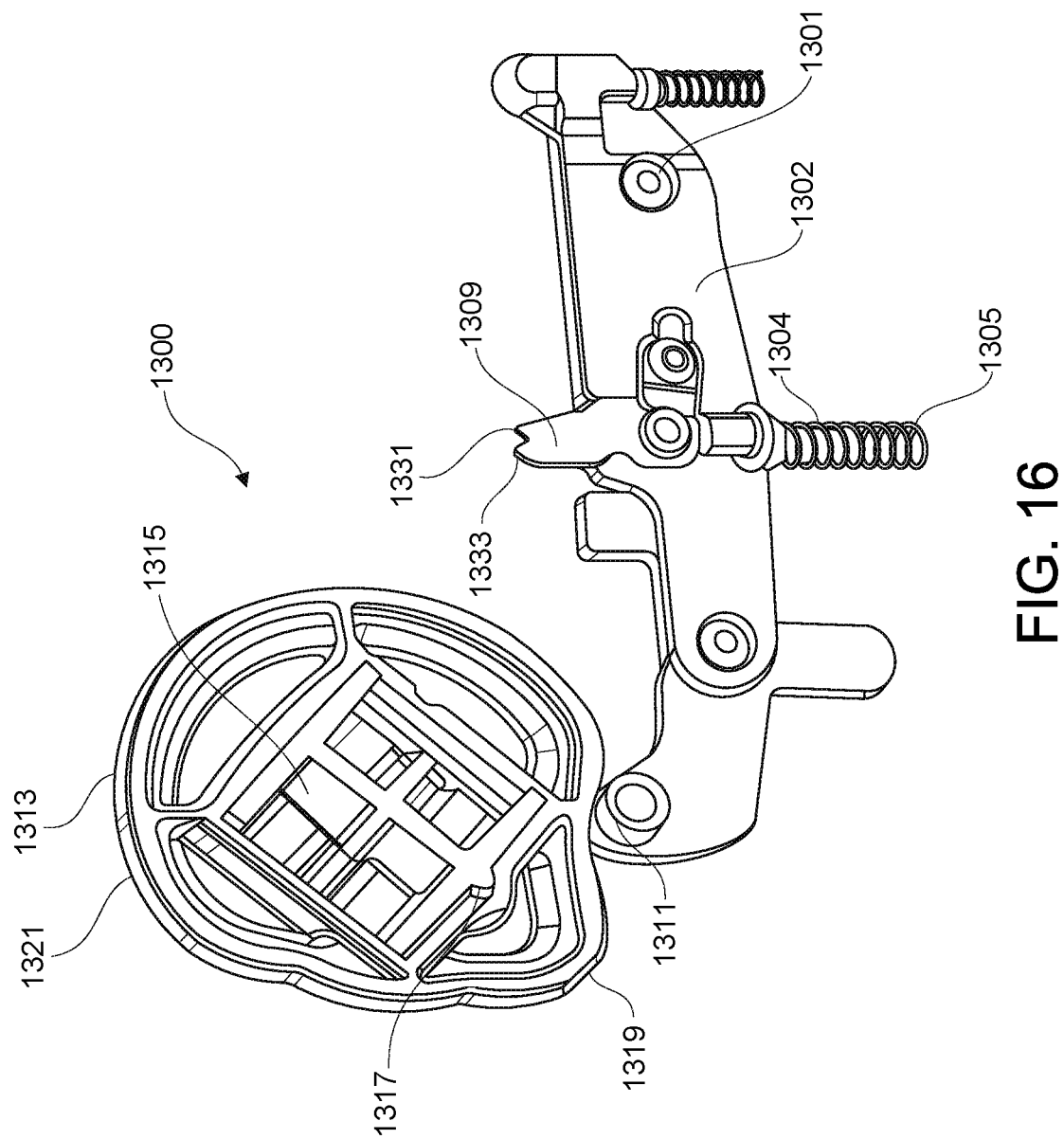
FIG. 16 shows a cam assembly comprising a ram on an axle.
Figure 17:
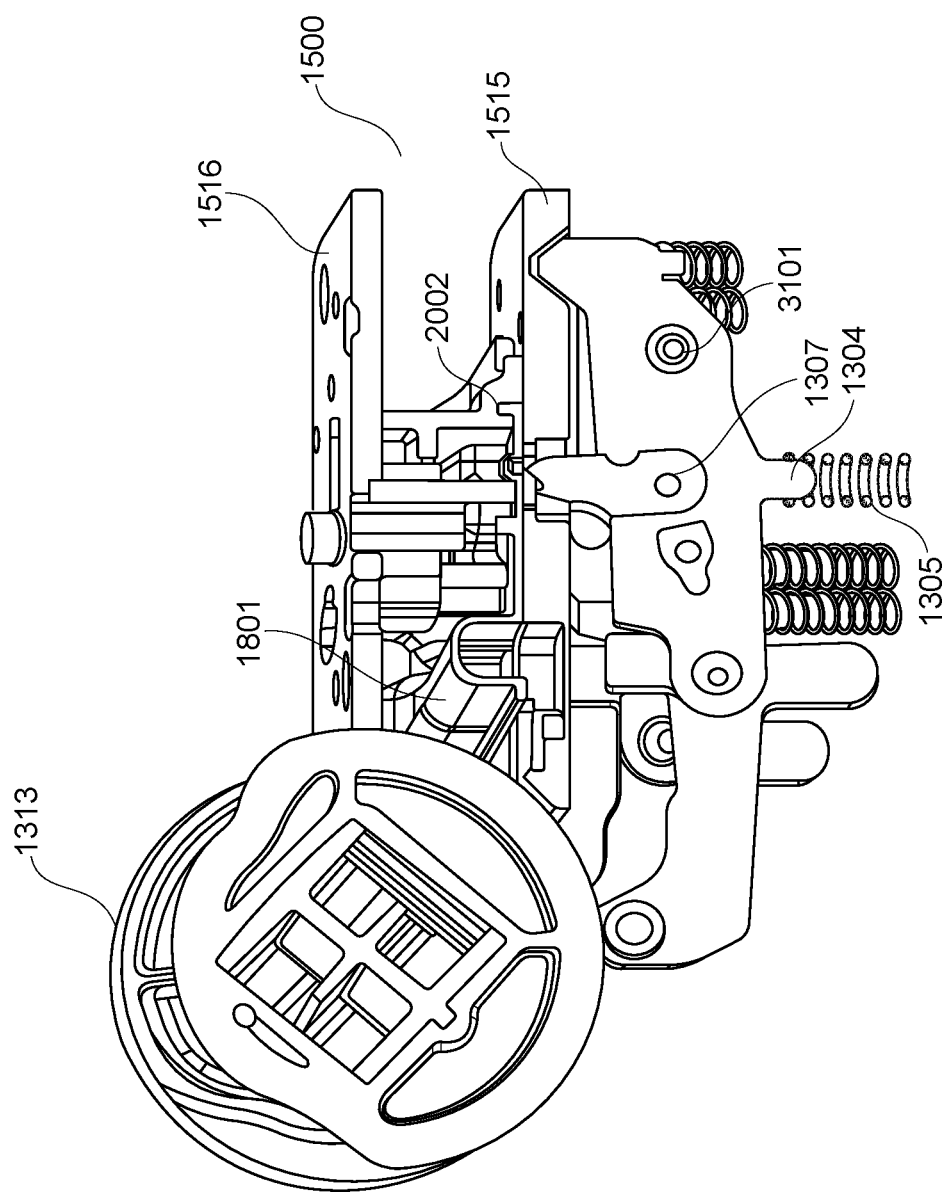
FIG. 17 shows a sectioned view shows a ram pressing against a valve.

FIG. 15, FIG. 16 and FIG. 17 show an embodiment of a cartridge interface 1500 mated with a sample cartridge 1801. In this embodiment rams are comprised in a cam mechanism 1300. Cam mechanism 1300 comprises cam 1313 and cam follower 1311. Cam 1313 has cam surface 1321, cam protrusion 1319 and cam aperture 1315 configured with a cam key 1317 adapted to position the cam on a rotating element. Cam follower 1311 is mounted on lever 1303, which rotates about an axle connected through aperture 1301. Ram 1309 (sometimes referred to as a "knife") is configured as a protrusion mounted on lever 1302. Ram 1309 can be configured as a piece held in place by a holder on lever 1302. Ram 1309 can comprise centering guide 1333 and ram head 1331, adapted to press into the valve. The lever can be biased toward the valve with a biasing element 1305, for example with a spring. A spring can be mounted on mount 1304. In one embodiment, a biasing element exerts a force of at least any of 5 pounds, 6 pounds, 7 pounds, 8 pounds, 9 pounds or 10 pounds. The cam can be a plate cam, e.g., can take the shape of an eccentric disc comprising an eccentricity 1319. The cam can include an aperture 1317 adapted for mounting the cam on a rotation device, such as a drum driven by a motor. The cam aperture can include a key 1317 to align the cam on the drum. Rise of the cam follower pushes the ram away from the valve. Return of the cam follower allows the ram to push against the valve from the force of the biasing element. In certain embodiments, the cam surface 1321 may pull away from cam follower during valve closure, to allow biasing element 1305 to exert full force against the valve.

Cartridge interface 1500 includes ram actuation assembly 1517, base plate 1515 and cover plate 1516. Sample cartridge 1801 is inserted into a slot formed by the mating of base plate 1515 and cover plate 1516.

Ram actuation assembly 1517 can include cam array 1501; ram array 1509 and an array of biasing elements. The cam array can comprise a plurality of cams 1313 mounted on rotating drum 1507. The ram array can comprise a plurality of ram effectors, each comprising lever 1303 mounted on axle through aperture 1301, ram 1309 and cam follower 1311. Each ram mechanism is configured to engage a cam, and each ram to engage a valve of the sample cartridge.

Figure 20:
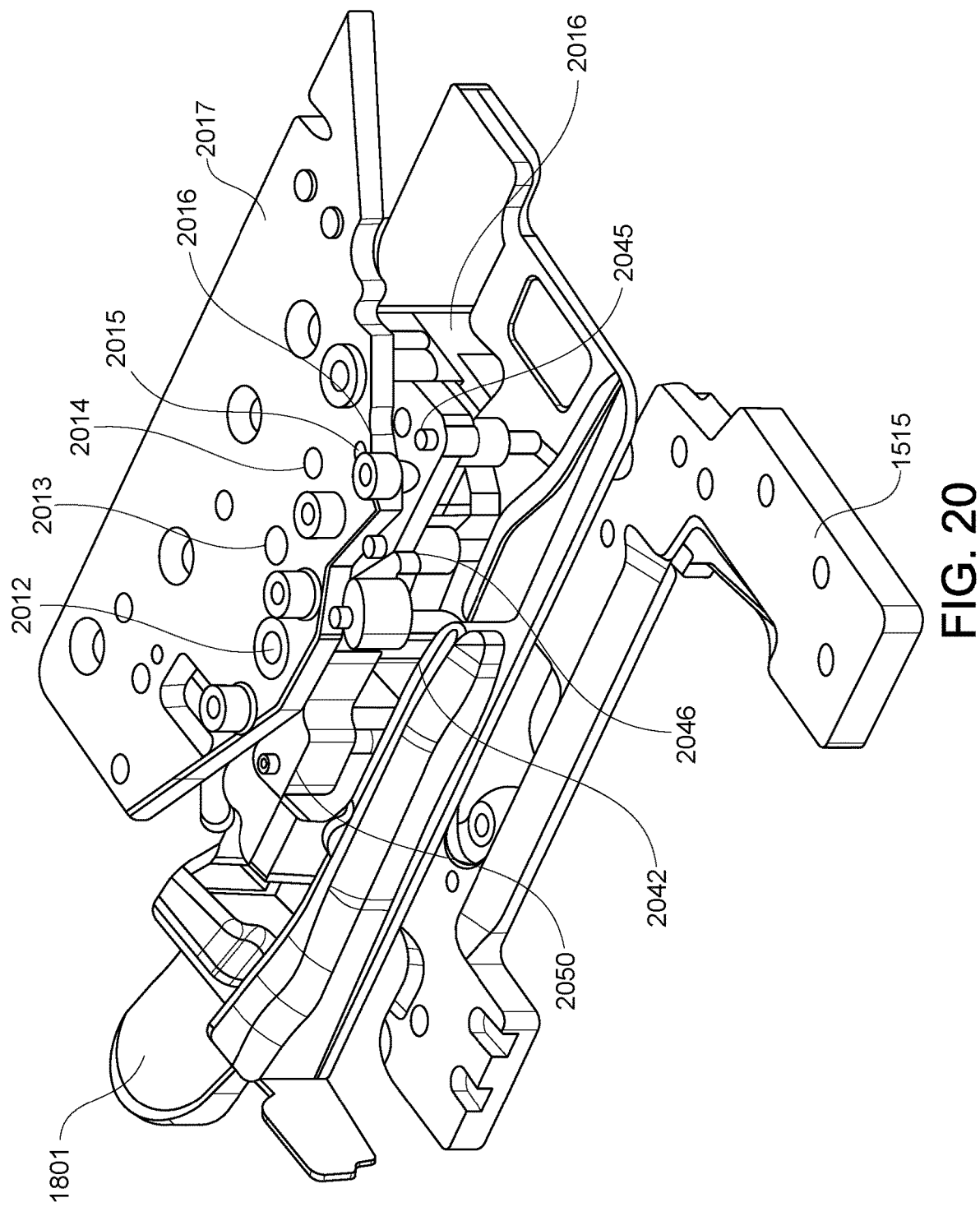
FIG. 20 shows an exemplary cartridge interface of this disclosure.

Referring to FIG. 20, base plate 1515 includes a surface against which a surface of a cover plate can mate and apertures through which rams can protrude. Rams can be biased against a wall of the aperture for guidance. A cover piece 2016 mates with a face of base plate 1515 and forms a guide. The guide guides a rail on cartridge 1801 when the cartridge is inserted into the cartridge interface. A top piece 2017 includes apertures for pistons or plungers configured to actuate ball valves to chambers connected to ports. These include pistons 2042, 2045, 2046 and 2050, which are aligned with valves and which provide a stop against the pressure of the rams. Apertures 2014, 2015 and 2016 guide plungers to depress ball valves. The top piece also includes apertures 2012 and 2013 through which fluid conduits pass to mate with input and output ports in the cartridge. The conduits are fluidically connected to a sample analysis sub-assembly, to convey analytes and air pressure to the cartridge.

Turning the drum through a rotation closes and releases valves when the eccentricity engages and disengages the cam follower. In one embodiment, the eccentricities on the drum are staggered, such that during a rotation of the drum valves are closed in a pre-determined sequence. The eccentricities can be staggered, for example, by positioning the eccentricity relative to the key such that mounting the cam on the drum placed the eccentricity in a preselected position. One such sequence is shown in FIG. 28. The sequence is executed by one full turn of the drum, which can be turned by a stepper motor to each next position in the rotation.

V. Integrated System

Systems provided herein may be capable of preparing, processing and analyzing a single sample or a plurality of samples. Several operations can be performed by the system provided herein, for example, (a) receiving one or more samples; (b) isolating and extracting target material from the received sample; (c) purifying and amplifying the whole target material or selective portion of the target material to produce an analyte ready to be examined; and (d) separating, detecting and analyzing the prepared analyte. These operations can be conducted and performed in a system that comprises several integrated sub-systems, for example, a sample preparation sub-system, a sample analysis sub-system and a control-sub-system. In some cases, a system may comprise a user interface, a sample cartridge interface, and an electrophoresis interface. The sample cartridge interface and the electrophoresis interface are configured to releasably engage with a sample cartridge for sample processing, and an electrophoresis cartridge for sample analysis respectively.

Systems provided herein can be fully automated, enabling a user to receive, process and analyze a sample without substantial labor and input. Sample preparation, processing and analysis can be accomplished in provided systems without the necessity of manually removing and transferring the sample, reagents and analytes among different parts in the system. Since the incorporated sub-units (e.g., sample cartridge and electrophoresis cartridge) are highly integrated and bear small sizes, systems provided herein can be dimensioned to minimize footprint, enabling the portability and usefulness in a wide context of applications. For example, the systems may be used in on-the-go situations, such as remote locations, or they may be used in situations in which transportation is not readily available or user mobility is desired, such as battlefields scenarios and crime scenes.

The cartridges of this disclosure are useful in integrated and automated sample-to-answer systems that, starting from a sample comprising biological material, generate an analysis of the sample. In other embodiments, the cartridges can be used for stand-alone sample preparation. In certain embodiments, the biological material is DNA and the genetic profile involves determining one or a plurality of alleles at one or a plurality of loci (e.g., genetic loci) of a subject, for example, a SIR (short tandem repeat) profile, for example as used in the CODIS system. The system can perform several operations, including (a) extraction and isolation of nucleic acid; (b) amplification of nucleotide sequences at selected loci (e.g., genetic loci); and (c) detection and analysis of amplification product. These operations can be carried out in a system that comprises several integrated modules, including an analyte preparation module; a detection and analysis module and a control module.

Various chemistries are commercially available to perform STR analysis and, in particular, CODIS-compatible STR analysis. These include, for example, Globalfiler® and Globalfiler® Express (6-dye, 24-locus STR kit, from Life Technologies/Thermo Fisher Scientific (Grand Island, N.Y.) (worldwide web site: lifetechnologies.com/us/en/home/industrial/human-identification/globalfiler-str-kit.html), and PowerPlex® Fusion (e.g., PowerPlex® Fusion 6C) from Promega Corporation (Madison, Wis.) (worldwide web site: promega.com/Products/Genetic-Identity/STR-Analysis-for-Forensic-and-Paternity-Testing/PowerPlex-Fusion-STR-Kits?utm_medium=print&utm_source=ishi_poster&utm_campaign=powerplex&utm_content=October).

Systems provided herein may be fully integrated. Sample processing can be accomplished in a single system without having to remove a sample and transfer it to another system. Systems provided herein can be fully automated, enabling a user to process a sample without substantial input from the user.

Figure 19:
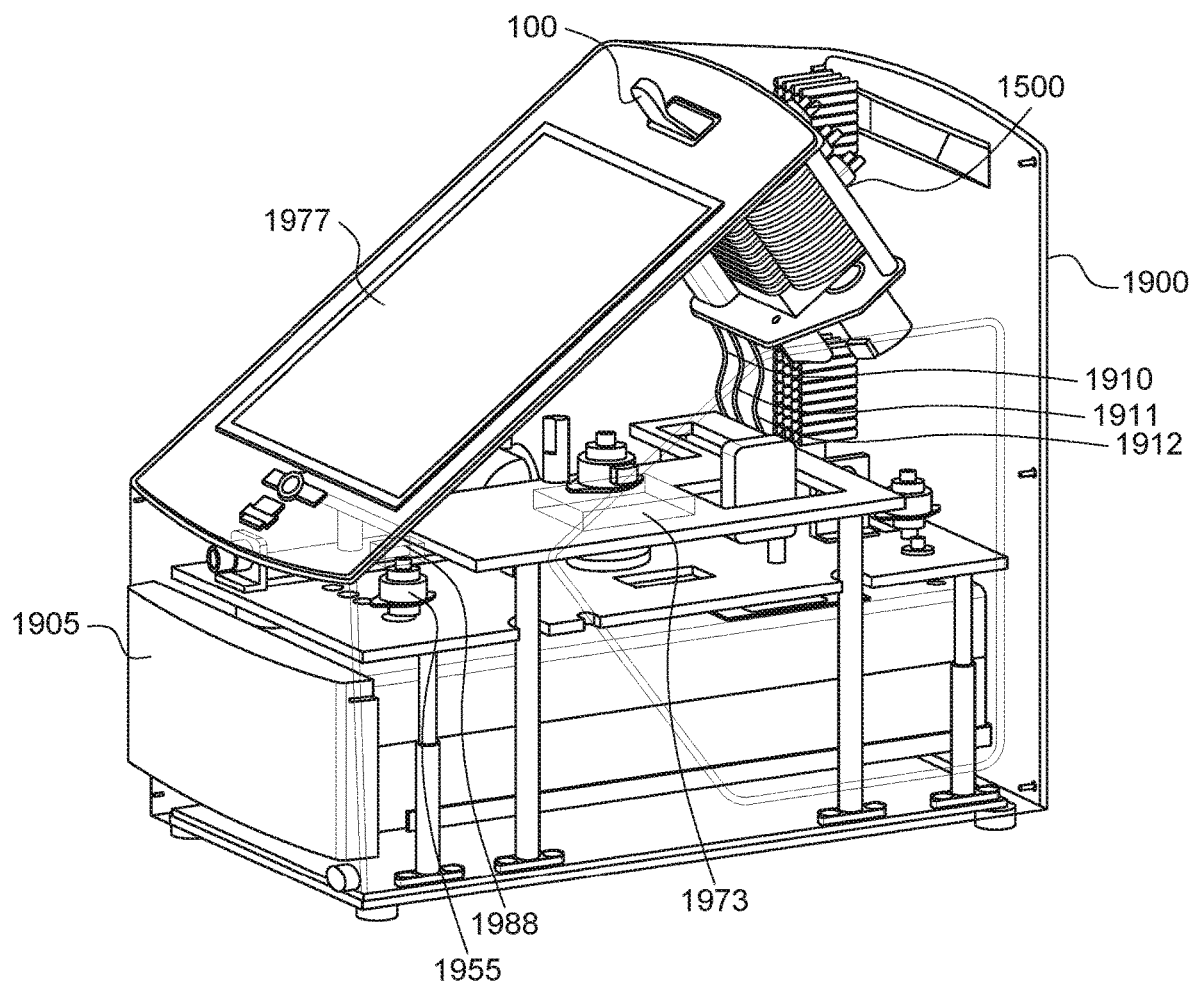
FIG. 19 shows an exemplary system of this disclosure.

FIG. 19 shows an exemplary system of this invention. System 1900 includes several functional elements. System 1900 can include a sample preparation sub-system, a sample analysis sub-system and a control sub-system. Such an instrument comprising an interface for engaging a cartridge of this disclosure, actuating valves and moving liquids is described in U.S. Provisional Patent Application Ser. No.

62/069,752, filed Oct. 28, 2014, which is incorporated herein by reference in its entirety.

A sample preparation sub-system can include a sample cartridge interface 1500 configured to engage a sample cartridge 100, sources of reagents for performing a biochemical protocol, a fluidics assembly configured to move reagents within the sample preparation subsystem. A fluidics assembly can include a pump, such as a syringe pump. The pump is fluidically connectable through valves to the outlets for reagents such as water and lysis buffer and to a source of air. The pump is configured to deliver lysis buffer and water through fluidic lines 1910 and 1911, respectively, to inlet port 112 in the sample cartridge. Air or liquid pressure applied by the pump to inlet port 112 can pump analyte out outlet port 113 and through line 1912 into the analyte inlet in the electrophoresis cartridge.

A sample analysis sub-system can include an electrophoresis assembly including an anode, a cathode and an electrophoresis capillary in electric and fluidic communication with the anode and cathode, and a sample inlet communicating between a sample outlet in the sample cartridge and an inlet to the capillary. These can be contained, e.g., within an electrophoresis cartridge 1905. The sample analysis sub-system can further include an optical assembly including a source of coherent light, such as laser 1988, an optical train, including, e.g., lenses 1955, and a detector, configured to be aligned with the electrophoresis capillary and to detect an optical signal, e.g., fluorescence, therein. In this embodiment, the electrophoresis cartridge also includes a source electrophoresis separation medium and, optionally (d) sources of liquid reagents, such as water and lysis buffer, delivered through outlets in the electrophoresis cartridge to the system.

A control sub-system can include a computer 1973 programmed to operate the system. The control sub-system can include user interface 1977 that receives instructions from a user which are transmitted to the computer and displays information from the computer to the user. The user interface 1977 may be as described in U.S. Provisional Patent Application Ser. No. 62/067,429, filed Oct. 22, 2014, which is entirely incorporated herein by reference. Optionally, the control sub-system includes a communication system configured to send information to a remote server and to receive information from a remote server.

A sample preparation module includes a cartridge module assembly configured to engage and operate one or more than one sample cartridge. A sample cartridge is configured to receive one or more samples and to perform nucleic acid extraction and isolation, and DNA amplification when the cartridge is engaged with a cartridge module assembly in the system. It can also include controls and standards for assisting in analysis.

The sample preparation module can include a receptacle for receiving one or more cartridges, an engagement assembly to engage the cartridge; a fluidic manifold configured to engage ports in a cartridge and to deliver pressure and/or fluids to the cartridge through the ports; a delivery assembly configured to deliver reagents, such as amplification pre-mix, from a compartment in the sample cartridge to an amplification compartment (e.g., plungers to push ball valves into an open position; a pneumatic manifold configured to engage ports in a cartridge and to deliver positive or negative pressure to the cartridge through the ports for moving fluids and operating valves, pumps and routers in the cartridge; a pump configured to deliver pressure to the fluidic and pneumatic manifold. Consumable reagents can be carried in a module, e.g., a buffer module, that is, removably engageable with the cartridge module.

The system also can include an interface adapted to mate with a pressure port in the cartridge and to transmit positive or negative pressure from a pressure source to the port and into the fluidic circuit. The interface can include a nozzle which the port fits. It can include a syringe for applying positive or negative pressure from another source.

PCR can be carried out using a thermal cycler assembly. This assembly can include a thermal controller, such as a Peltier device, infrared radiation source, circulating water, movement of constant temperature blocks, or other material, which can be configured to heat and cool for thermal cycling and can be comprised in the cartridge module which can be configured to move the thermal controller into thermal contact with the thermal cycling chambers, for example, through a heat spreader (or thermoconductor that can spread/distribute heat and cooling) disposed over each reaction chamber. In some embodiments, the cartridge comprises a temperature regulator assembly having one or more (e.g., a plurality) of thermocycling chambers and the sample cartridge can be in fluid communication with a fluidic channel.

An analysis and detection module is configured to receive analyte from the sample preparation module and perform capillary electrophoresis on the analyte to detect analytes separated by electrophoresis and to analyze the detected analytes. It can include a capillary electrophoresis assembly, a detection assembly, and an analysis assembly.

The capillary electrophoresis assembly can include an injection assembly, that can include a denature heater assembly, a positioning assembly for positioning an analyte for capillary injection; a cathode assembly; a capillary assembly; an anode assembly; a capillary filling assembly for filling a capillary with separation medium and a power source for applying a voltage between the anode and the cathode.

A detection assembly can comprise a laser configured to illuminate the capillaries and a detector. The laser can be configured to excite fluorescent dyes in the analyte. In alternative embodiments, the laser can be replaced by an alternate light source such as an LED. The detector can include a CCD array, CMOS array, photomultiplier, diode array, or other detector, for detecting light produced by excited dyes and for producing an output signal.

An analysis assembly can include a computer comprising memory and a processor for executing code (e.g., code on a tangible medium) for analyzing the output signal and producing a computer file containing an analysis of the signal. Such an analysis can include, for example, identification of alleles from various STR loci. The computer file can be in a format that is compatible with public databases. For example, the file can be in CODIS format which is compatible with the National DNA Index System (NDIS) operated by the FBI.

The system can be operated by a control module. The control module can include a user interface configured to receive instructions from and deliver information to a user. It can include software programmed to execute routines for performing the operations mentioned, above, and transmit and receive information, such as computer files, from remote locations, for example, over the internet.

Figure 27A:
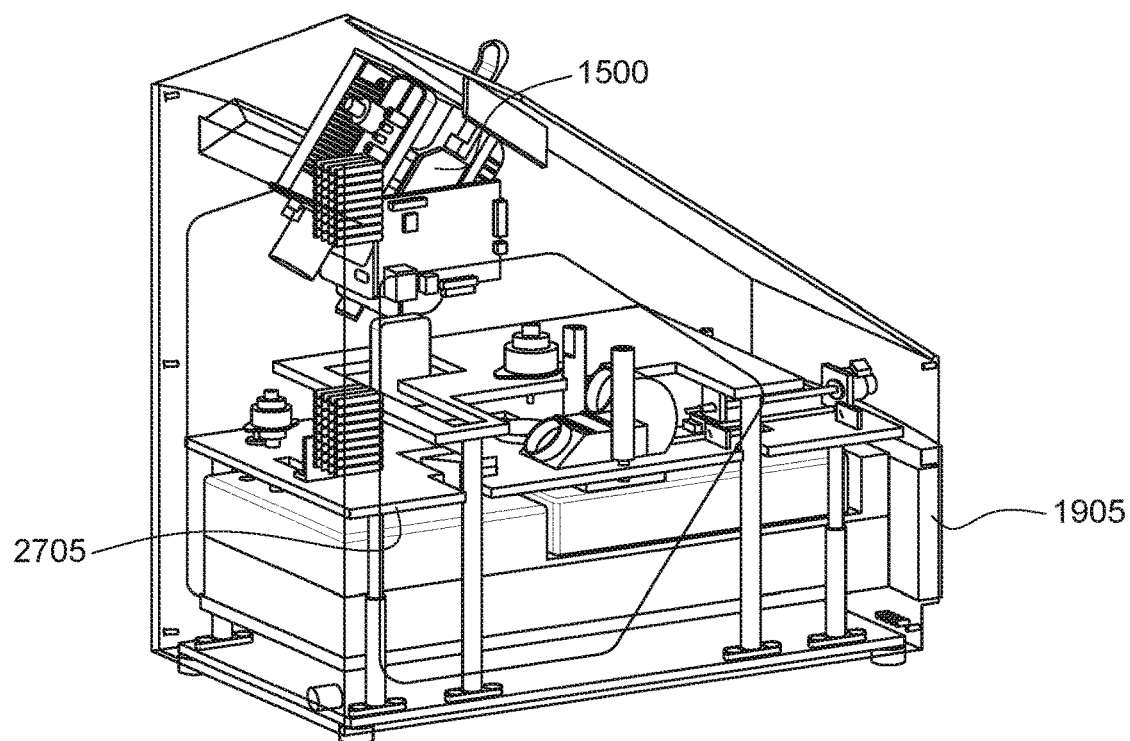
FIG. 27A and FIG. 27B are isometric views of the system of FIG. 19.
Figure 27B:
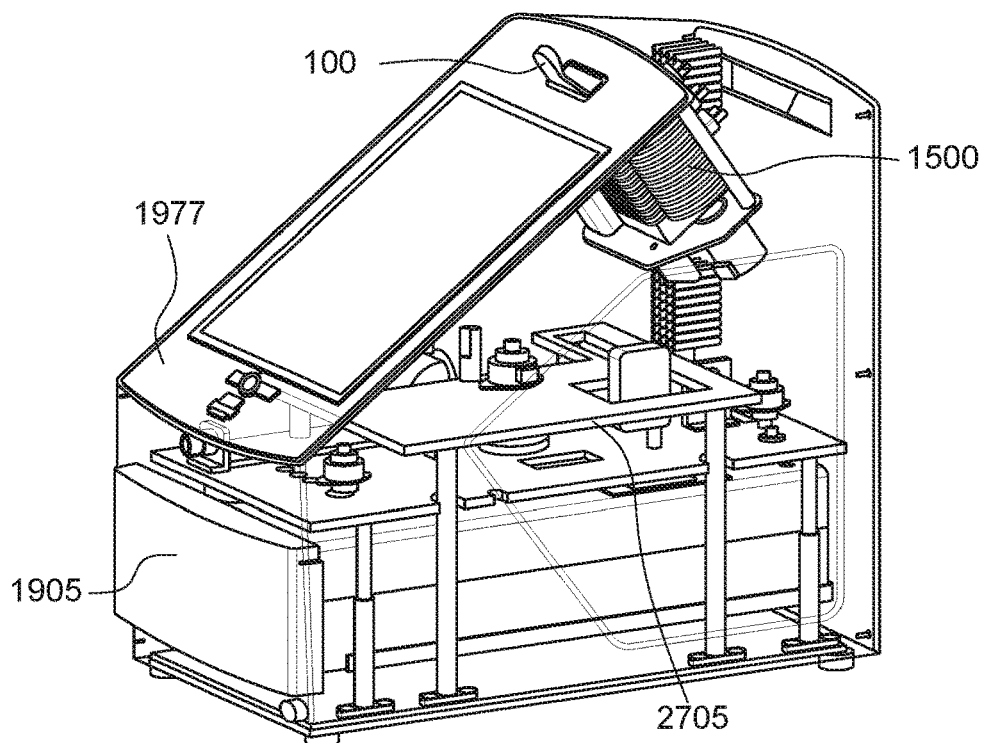

FIG. 27A and FIG. 27B present the system of FIG. 19 in further detail. As described above and elsewhere herein, a sample cartridge interface 1500 and an electrophoresis interface 2705 are comprised in the system, for engaging the sample cartridge and the electrophoresis cartridge. Both the sample cartridge and the electrophoresis cartridge can be releasably or removably engaged with the system. The system of FIG. 19, FIG. 27A and FIG. 27B can be used in forensic analysis to decode the genetic information of a single sample. In some cases, the system may be used to determine the genetic profile of a sample in less than about 6 hours, 5 hours, 4 hours, 3 hours, 2.5 hours, 2 hours, 1.5 hours, 1 hour, 30 minutes, 20 minutes, 10 minutes, 5 minutes 1 minute or less. Such time may depend upon, for example, the number of steps included in sample processing operations.

Figure 18:
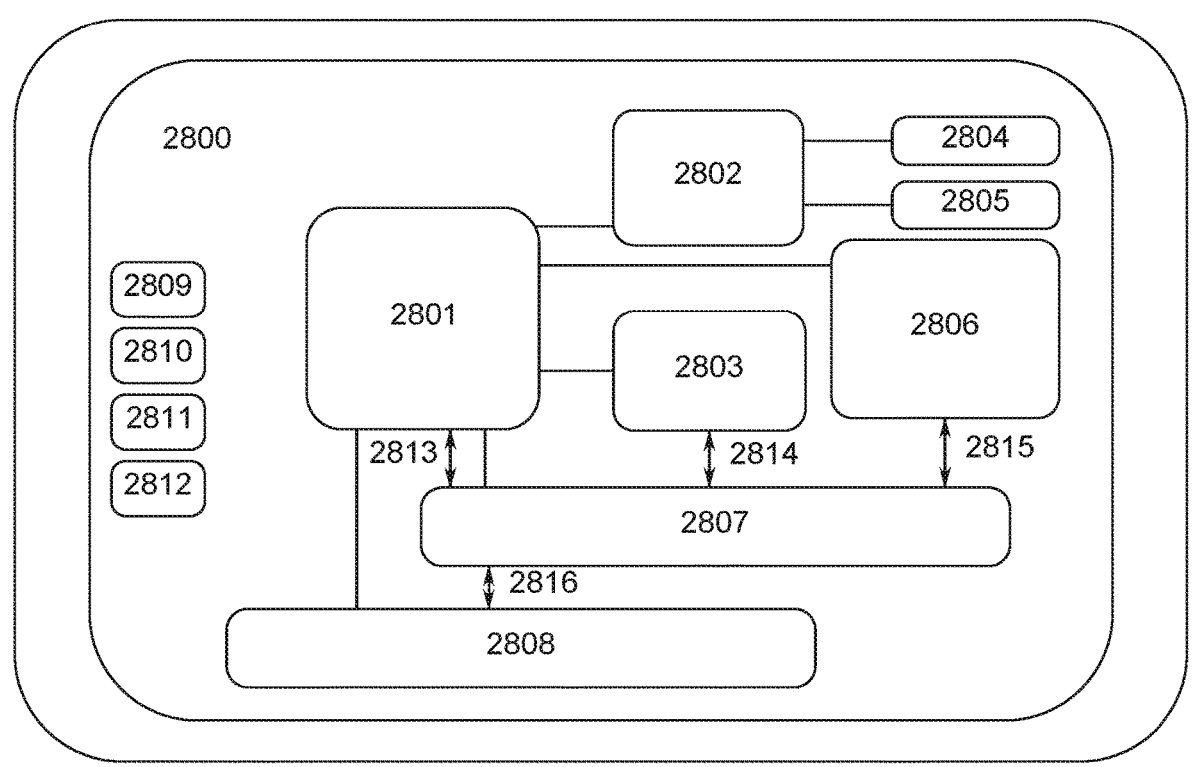
FIG. 18 shows a schematic of an example electrophoresis cartridge-comprising system.

A schematic of the system of FIG. 19, FIG. 27A and FIG. 27B is illustrated in FIG. 18. A chassis 2800 is included for structural support, which may be formed of a metallic material, such as aluminum or steel, a polymeric material, or a combination thereof. In some cases, the chassis may be structured to minimize the weight of the system. A user interface which comprises system electronic controls 2801, embedded computer 2802, and a user interface screen capable of identifying and reading fingerprint 2804 and sample patch barcode 2805, is included in the system. The user interface receives and processes requests or instructions from and delivers information to a user. It can include software programmed to execute routines for performing the operations mentioned, above, and transmit and receive information, such as computer files, from remote locations, e.g., over the internet. The user interface can also enable the user to monitor the progress of the operation and make changes to the operation of system if measurements are not within selected parameters. A sample cartridge interface 2806 is provided for receiving a sample cartridge for sample processing. The sample cartridge described herein can be configured to receive one or more samples and to perform at least one of sample isolation, extraction, purification, amplification or dilution, when the sample cartridge is engaged with the sample cartridge interface of the system. Sample amplification can include polymerase chain reaction (PCR). One or more reagents that are needed for performing one or more steps of sample processing may be pre-loaded or comprised in the sample cartridge, for example, washing buffer, lysis buffer, diluent, amplification reagents, or internal lane standards. Also comprised in the system is a fully integrated electrophoresis cartridge 2807 which is releasably engageable with the system via an electrophoresis cartridge interface. The electrophoresis system comprises all essential parts for performing an electrophoretic analysis, such as an electrophoresis capillary, electrodes (e.g., anode and cathode), electrophoresis separation medium, or electrophoresis buffer. In some cases, it may comprise reagent that can be used to perform STR analysis. It may further comprise one or more reagent container for holding reagents that are used for sample processing, e.g., a lysis buffer container. The lysis buffer may be placed in fluidic communication with the sample cartridge and used for isolating the target material out of the sample during sample processing, after both the sample cartridge and the electrophoresis cartridge are engaged with the system. Once the engagement of the electrophoresis cartridge is completed, at least one automatic communication between the electrophoresis cartridge and the system may be established, for example, an electrical communication 2813 between the electrophoresis cartridge and the system electronic controls 2801, an optical communication 2814 between a portion of the electrophoresis capillary in the electrophoresis cartridge and an optics module 2803 of the system, a fluidic communication 2815 between a sample inlet port of the electrophoresis cartridge and a sample outlet port of the sample cartridge, a mechanical and thermal 2816 communication between the electrophoresis cartridge and a motorized drives and cooling module 2808 of the system.

In one example, the integrated electrophoresis cartridge 2807 has all or substantially all of the components necessary for electrophoresis in a compact unit that is readily insertable into and removable from the electrophoresis cartridge interface. This may permit a user to readily engage the cartridge 2807 with the system without having to open the system. In some examples, all or substantially all of the components necessary for electrophoresis (e.g., anode, cathode and at least one electrophoresis capillary are included on a single board or support or multiple boards or supports that are securably integrated with one another.

The system provided herein may further comprise a power source 2812 for supplying the power for the system, AC power source 2811 for applying a voltage gradient across the anode and the cathode, one or more fans 2810 for dissipate the heat for one or more parts of the system, and one or more USB ports 2809 for collecting and transferring data either within the system or outside the system.

Figure 24:
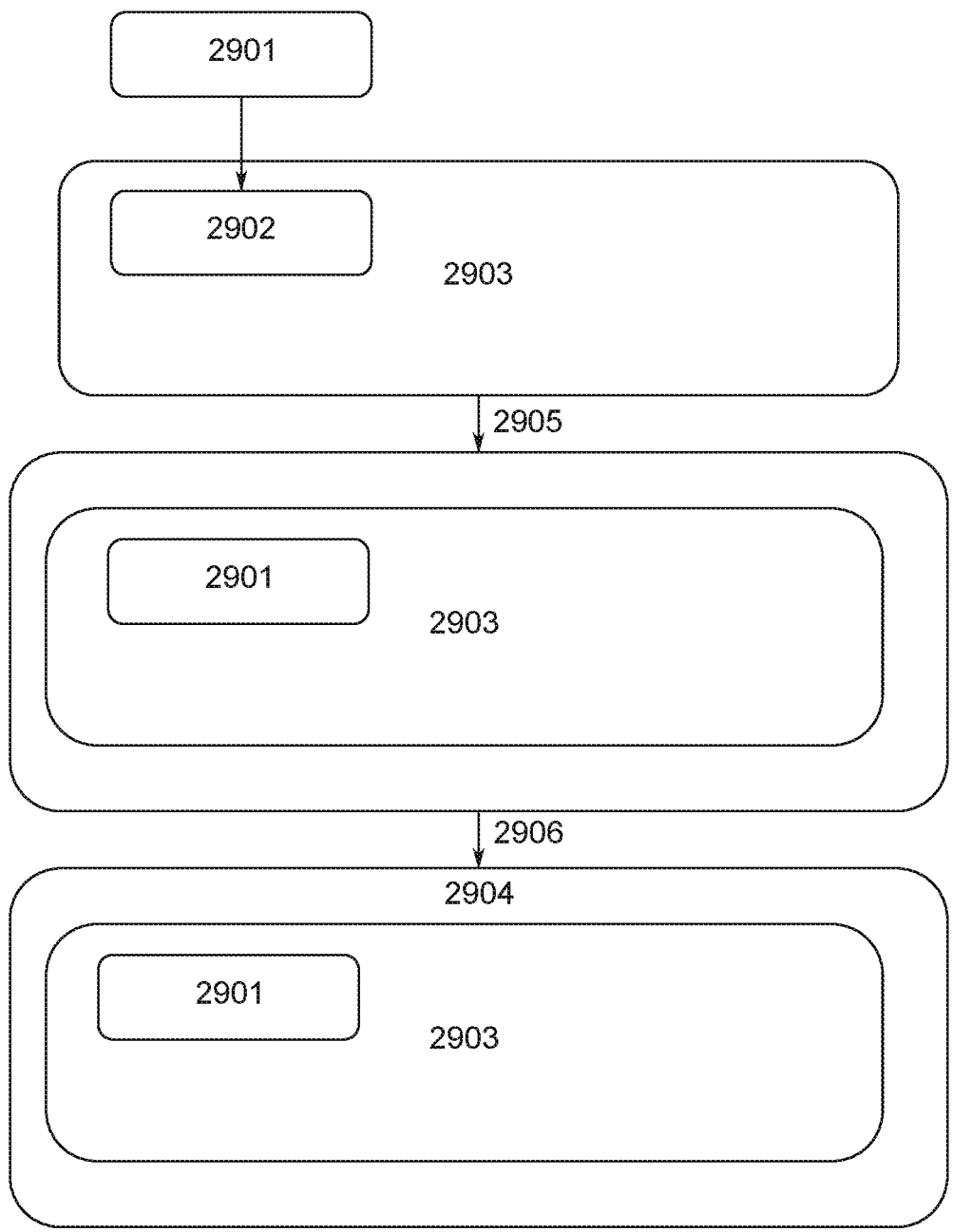
FIG. 24 schematically illustrates an example system engaging an electrophoresis cartridge.

Also provided herein, the electrophoresis cartridge may comprise one or more of sub-containers or sub-cartridges that are removably insertable in the electrophoresis cartridge, such as, sub-containers for holding electrophoresis separation medium, reagents for sample processing, or reagents for sample analysis. FIG. 24 shows an example of an electrophoresis cartridge comprising an electrophoresis separation medium sub-container. As shown in FIG. 24, an electrophoresis cartridge is manufactured to have a space 2902 configured to specifically receive and accommodate a secondary or sub-container. A sub-container 2901 used for holding the electrophoresis separation medium can be stored outside the electrophoresis cartridge 2903 before the engagement of the electrophoresis cartridge with the system. The sub-container which holds the electrophoresis separation medium may be installed 2905 into the electrophoresis cartridge a short time before the engagement of the electrophoresis cartridge with the system, for example, less than 1 hour, 50 minutes, 40 minutes, 30 minutes, 20 minutes, 15 minutes, 10 minutes, 5 minutes before engaging the electrophoresis cartridge with the system. Once the electrophoresis cartridge is installed 2906 into the system, the sub-container may be placed in thermal communication with a thermal control module of the system, which may adjust the temperature of the sub-container to a desired value and maintain it for a period of time.

Figure 25A:
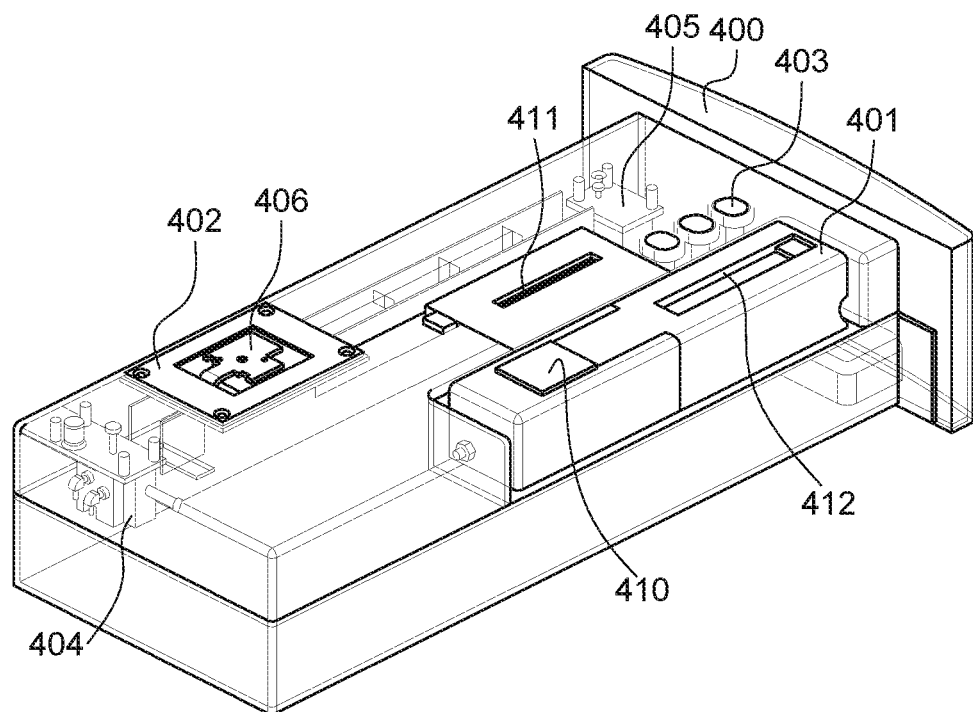
FIG. 25A and FIG. 25B are isometric view of an example electrophoresis cartridge.
Figure 25B:
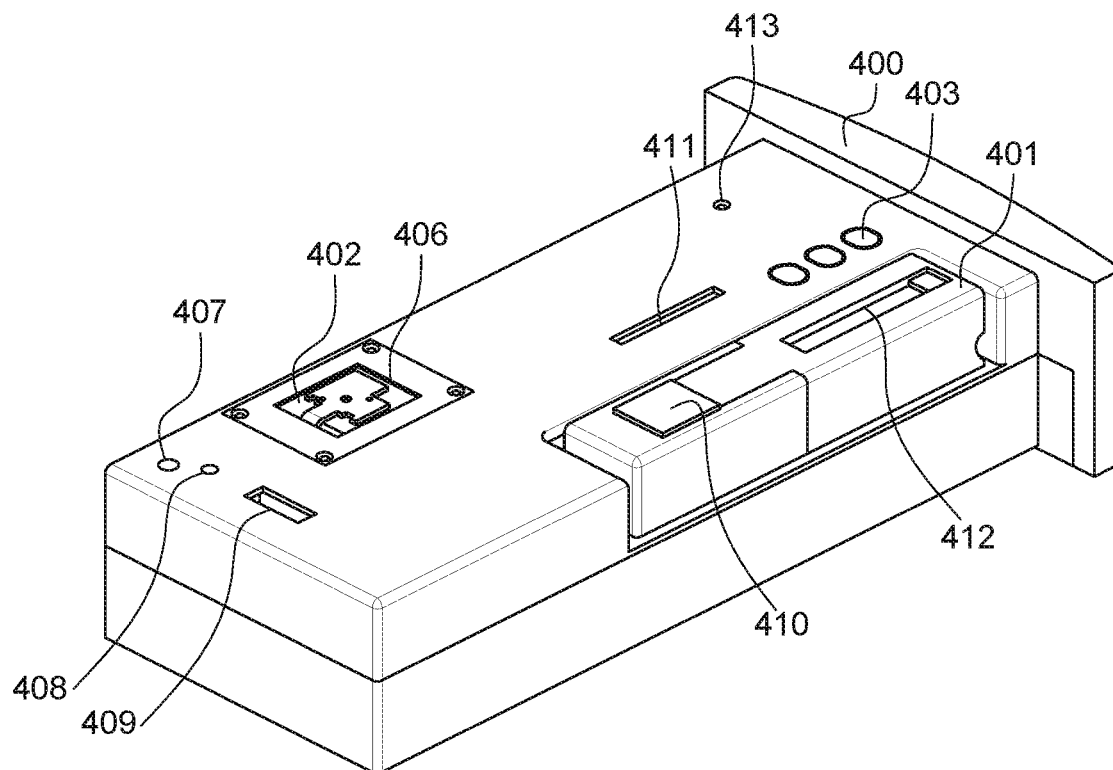

FIG. 25A and FIG. 25B show clear shell views of an example electrophoresis cartridge of the present disclosure. In general, the electrophoresis cartridge may comprise a cartridge casing 400, a sub-container (or sub-cartridge) casing 401, an optical interface 402 for providing a light source and detecting signals from analytes, one or more hydrodynamic devices (e.g., fluid coupling) 403, an anode sub-assembly 404, a cathode sub-assembly 405, an electrophoresis capillary 406, an electrical interface 407, one or more mechanical interfaces (e.g., 408, 409, 412 and 413) for applying pressure or forces on parts of the electrophoresis cartridge, a thermal interface 410 for control the temperature of the sub-container 401, and an electrical interface 411 for providing a voltage between at least one anode in the anode sub-assembly and at least one cathode in the cathode sub-assembly.

Figure 26:
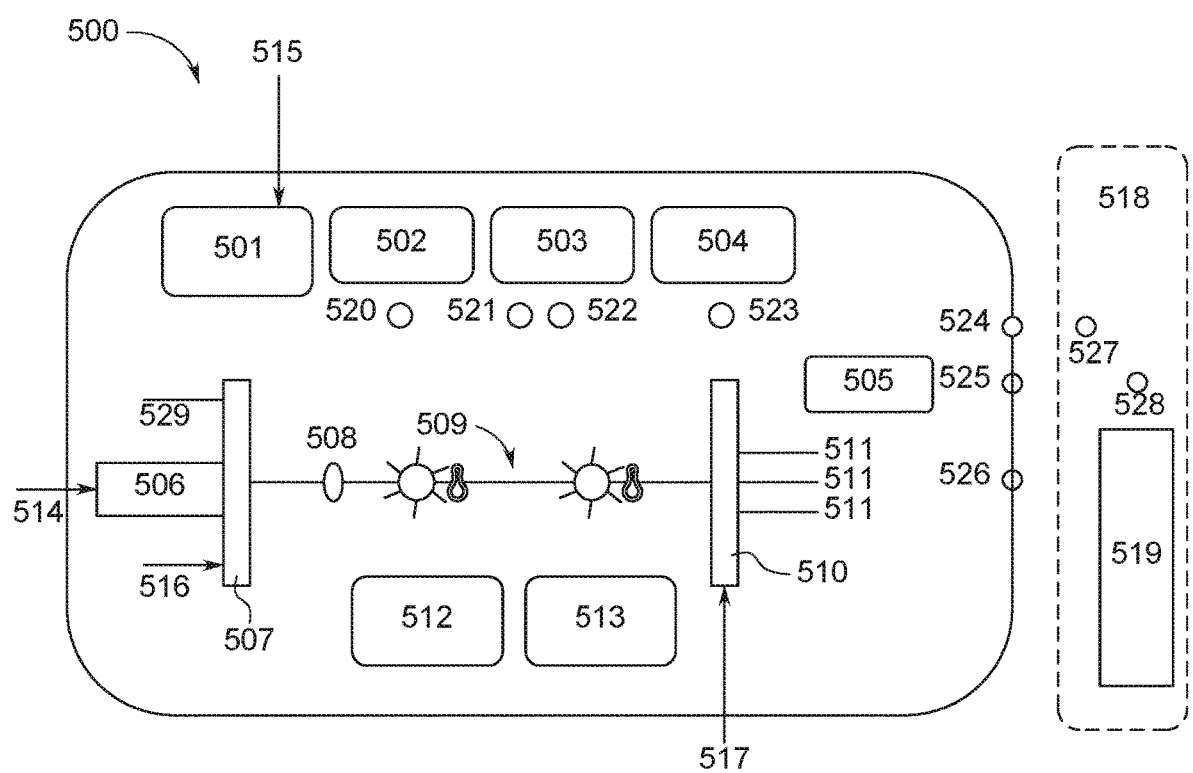
FIG. 26 shows a schematic of an example electrophoresis cartridge.

A schematic of an example electrophoresis cartridge 500 is shown in FIG. 26. The electrophoresis cartridge 500 may comprise an electrophoresis assembly which includes an anode sub-assembly 507, a cathode sub-assembly 510, and at least one electrophoresis capillary 509 to be used in sample separation and analysis for at least one sample.

As shown in FIG. 26, three cathode nodes 511 can be included in the cathode sub-assembly and in fluidic and electrical communication with a first end of the electrophoresis capillary. At least one anode node 529 is comprised in the anode sub-assembly and in fluidic and electrical communication with a second end of the electrophoresis capillary. Although presented in the present disclosure are an anode sub-assembly and a cathode sub-assembly comprising one anode node and three cathode nodes, it shall be appreciated that any positive number of anodes and cathodes may be used, dependent upon, different applications.

The electrophoresis cartridge may also comprise more than one container for holding electrophoresis separation medium and more than one reagent for sample processing and analysis. As shown in FIG. 26, an electrophoresis separation medium container 501, a first reagent container 502, a second reagent container 503, a third reagent container 504, and a fourth reagent container 505 are included in the electrophoresis cartridge 500. The containers may be configured to be removably insertable into the electrophoresis cartridge. After each run of sample analysis, one or more containers may be replaced or reused, depending upon, the applications. In some cases, it may be desirable to store or transport one or more containers at a pre-determined temperature, for example, if a thermal-sensitive electrophoresis separation medium or electrophoresis reagent is used and the trivial change of temperature may impair its performance and thereafter result in the degradation or failure of the whole analysis. Once the containers are installed in the electrophoresis cartridge, they may be kept at the same or a different temperature. Installation of the containers may be realized manually or automatically.

Once the electrophoresis separation medium container 501 is properly engaged with the electrophoresis cartridge, with the aid of a first mechanical interface 515 for controlling one or more fluid handling devices (e.g., a pump), the electrophoresis separation medium may be driven and moved into the anode sub-assembly 507. The electrophoresis separation medium may be further pushed into at least one of the electrophoresis capillary with the application of a second and a third mechanical interface 514 and 516 by exerting a force (or pressure) on a high pressure piston 506 and an anode main piston (not shown).

Any suitable reagent may be used in the present disclosure. Reagents may be solid, semi-solid or liquid. In cases where liquid reagents are used, they may comprise organic fluid, inorganic fluid, or a mixture thereof. For example, reagents may comprise water, electrophoresis buffer, sample processing buffer (e.g., a lysis buffer), loading buffer, regeneration fluid, or combinations thereof. For example, reagents can be provided (e.g., stored) in an aqueous solution, or can be provided (e.g., stored) in a solid or dry (e.g., lyophilized) form and then placed into solution by addition of a liquid (e.g., an aqueous solution) as appropriate. Alternatively, reagents can be provided (e.g., stored) in a substantially water-free non-ionic organic solvent (e.g., an alcohol solvent) or in a substantially water-free ionic organic solvent (e.g., a deep eutectic solvent) and can be re-hydrated by addition of an aqueous solution as appropriate, as described in PCT Patent Publication No. WO 2014/055936, which is entirely incorporated herein by reference. As used in the present disclosure, the term "regeneration fluid" generally refers to a fluid that is able to renew or restore the function or performance of one or more parts of the electrophoresis cartridge, for example, the electrophoresis capillary. In some cases, the regeneration fluid may comprise an aqueous solution. In some cases, the regeneration fluid may comprise an alkaline fluid. In some cases, the regeneration fluid may comprise one or more alkali hydroxides.

To collect any liquid or fluid from, for example, an electrophoresis capillary, the anode sub-assembly, or the cathode sub-assembly, two waste containers 512 and 513 may be included in the electrophoresis cartridge and communicate with the anode-subassembly and the cathode sub-assembly, respectively. Any number of waste containers (e.g., at least 1, 2, 3, 4, or 5) may be included in the electrophoresis cartridge, as provided in the present disclosure. For example, besides the waste containers that are in communication with the anode sub-assembly and cathode sub-assembly, each of the reagent containers and the electrophoresis separation medium container may be provided with its water container.

In some aspects of the present disclosure, the electrophoresis cartridge may further comprise a plurality of fluid handling devices which place various parts or components of the electrophoresis cartridge in fluidic communication. As described above and elsewhere herein, any type of devices that is capable of moving or transferring the fluid may be used, such as valves, pumps, electrostatic fluid accelerators, and various other forms of process equipment. As shown in FIG. 26, pumps 520 and 521 are used to drive the reagents stored in the first and the second reagent containers 502 and 503 to the anode sub-assembly 507, through their respective fluid conduits. Similarly, pumps 522 and 523 are utilized to transfer the reagents kept in the second and the third reagent containers 503 and 504 to the cathode sub-assembly 510, through two separate fluid conduits.

In some cases, it may be desirable that at least one of the reagent containers communicate with more than one part of the electrophoresis cartridge or the system. For example, as illustrated in FIG. 26, the second and the third reagent containers 503 and 504 are placed in communication with parts outside of the electrophoresis cartridge, besides their communication with the cathode sub-assembly 510 of the electrophoresis cartridge as described above. In detail, both of the reagent containers are in fluidic communication with the sample cartridge interface 519 and a fluid handling device 518 through a fluid line. A four-port valve 528 and a three-port valve 527 are utilized to direct, control and regulate different types of fluid flow in the fluid line. Alternatively or additionally, it may be advantageous to have one or more reagent containers installed inside the electrophoresis cartridge which communicate directly with parts or components which are outside of the electrophoresis cartridge. For example, in the present example as shown in FIG. 26, a fourth reagent container 505 is engaged with the electrophoresis cartridge and placed in fluidic communication with the sample cartridge interface 519 through a fluid line. In some cases, one or more hydrodynamic devices (e.g., fluid couplings 524, 525 and 526) may be included in the electrophoresis cartridge which may aid in delivering and transferring the reagents, analytes or samples through the fluid line.

The electrophoresis cartridge may also comprise a sample delivery assembly comprising at least one sample inlet port and at least one sample line, with each sample line placing a sample inlet port in communication with the first end of the electrophoresis capillary through a passage in the cathode sub-assembly. The sample inlet port may be further configured to communicate with a sample outlet port comprised in a sample cartridge interface 519, via a hydrodynamic device 526, for example, a fluid coupling or a hydraulic coupling.

With the sample delivery assembly, the processed sample from a sample cartridge that is engaged with the sample cartridge interface may be directed to a separation channel (e.g., an electrophoresis capillary) via the sample line. Any suitable method for moving the prepared sample into the separation channel may be used in the context of the present disclosure. For example, field-amplified stacking (FAS) may be performed by positioning in an electrophoresis sample line a diluted mixture comprising the sample of lower salt concentration or lower ionic strength than used in the separation gel. In another example, a bolus of a material (e.g., air) can be positioned downstream of the sample in the sample line, wherein the material has an electrical conductivity that differs from the electrical conductivity of the electrophoresis buffer or the sample. When the sample is positioned across the separation channel, the sample can be electrokinetically injected into the separation channel at an appropriate voltage (e.g., about 3 kV to about 5 kV, or about 4 kV) over an appropriate amount of time (e.g., about 10 sec to about 20 sec, or about 15 sec). In some other examples, a pump may be used to drive the sample into the separation channel.

Once the prepared sample is moved into the separation channel, the sample may then be subjected to sample separation and analysis within the separation channel, with the aid of an electric field, as can be generated upon the application of a voltage gradient across the anode 529 and the cathode 511. Upon the effect of the electric field, analytes in the electrophoresis capillary move through the matrix (i.e., electrophoresis separation medium) at different rates, determined by one or more factors, such as mass, charge, or a combination thereof.

A portion of the electrophoresis capillary can be used as an optical window 508 which is capable of receiving a light from a light source and emitting signals that can be captured and detected by one or more detectors included in a detection assembly. In some cases, an optics module may be provided, which may comprise both the light source and the detection assembly. The light source is positioned to deliver a beam to at least one electrophoresis capillary via the optical window. One or more optical detectors (e.g., charge-coupled device (CCD), complementary metal-oxide-semiconductor (CMOS), photodetector, photo diode, or photomultiplier detector) may be optically coupled to receive signals emitted from at least one electrophoresis capillary through the optical window. As discussed elsewhere in the present disclosure, the optical communication between the optical window in the electrophoresis cartridge and both the light source and the optics module may be automatically established at the same time as the occurrence of the engagement of the electrophoresis cartridge.

The capillary can be heated to maintain an appropriate running temperature. The capillary can be heated by, for example, flowing temperature-controlled air over the capillary, by placing the capillary in thermal contact with a thermoelectric heater (e.g., a Peltier), or by placing the capillary in thermal contact with a resistive heater. An example of an assembly using a resistive heater to heat a capillary is described in U.S. Pat. No. 8,512,538. In another embodiment, a capillary heater assembly can comprise a flexible heater circuit comprising a resistive heater (e.g., a wire trace) in a polymeric substrate. Such flexible heater circuits are commercially available from Mod-Tronic (Thermofoil®), Kapton (polyimide heater) and McMaster-Carr (ultrathin heat sheet).

VI. Method of Using

The cartridges of this disclosure can be used in an integrated system for preparing a sample, for example, DNA isolation and amplification. For example, in one embodiment, a sample contained on for example a swab or a card punch, can be introduced into sample chamber 120. The cartridge can be engaged with cartridge interface 901. Cell lysis buffer contained in an off-chip reservoir can be feed through port 112 into the fluidic channel in the cartridge and into the sample chamber 120 by closing valves 141, 142, 143, and 147. Port 112 can be connected to a syringe or to another source of positive or negative pressure. After lysis, lysate can be moved through a fluidic channel on the cartridge, for example, with a plunger that applied vacuum through port 112 to draw the fluid into reaction chamber 122 by opening valves 147, 148, 149, and 142; and closing valves 146, 145, 143, 144, and 141. In one embodiment, the DNA reaction chamber can include material that captures a pre-determined amount of analyte. Excess fluid can be moved into waste chamber 123 while the reaction chamber is filled. Reagents for performing PCR or other reactions can be introduced into the reaction chamber through ports 115 and 116. In one embodiment, as detailed in US Patent application US 2013/0115607 and International Patent Application WO 2013/130910, an actuator pushes on ball valves, e.g., 803, to push the master mix in port 115 and the primers in port 116 into reaction chamber 122. A thermal control mechanism in the system can apply heat to perform thermal cycling in reaction chamber 122 of the cartridge with valves 148 and 149 closed. Following thermal cycling, valves 148, 145, 143 and 141 are opened and valves 149, 146, 147, 144, 142 are closed, and internal lane standard is dispensed from port 114 into reaction chamber 122 and pushed into mix chamber 121. Following mixing, valves 141,142, 145, 146 are closed; valves 143 and 144 are opened and the amplified STR mixture with internal lane standard is pushed to through port 113 to a capillary electrophoresis analysis module for separation, detection, and analysis.

A. Amplification and Cycle Sequencing—One Channel

In another embodiment, cartridges of this disclosure can be used to perform DNA amplification and subsequent preparation for cycle sequencing. The target for sequencing can be, for example, a diagnostic target, such as a gene for genotyping, a polynucleotide bearing a somatic mutation, e.g., from a tumor, or a polynucleotide from an infectious microorganism such as a bacterium or a virus.

Figure 21:
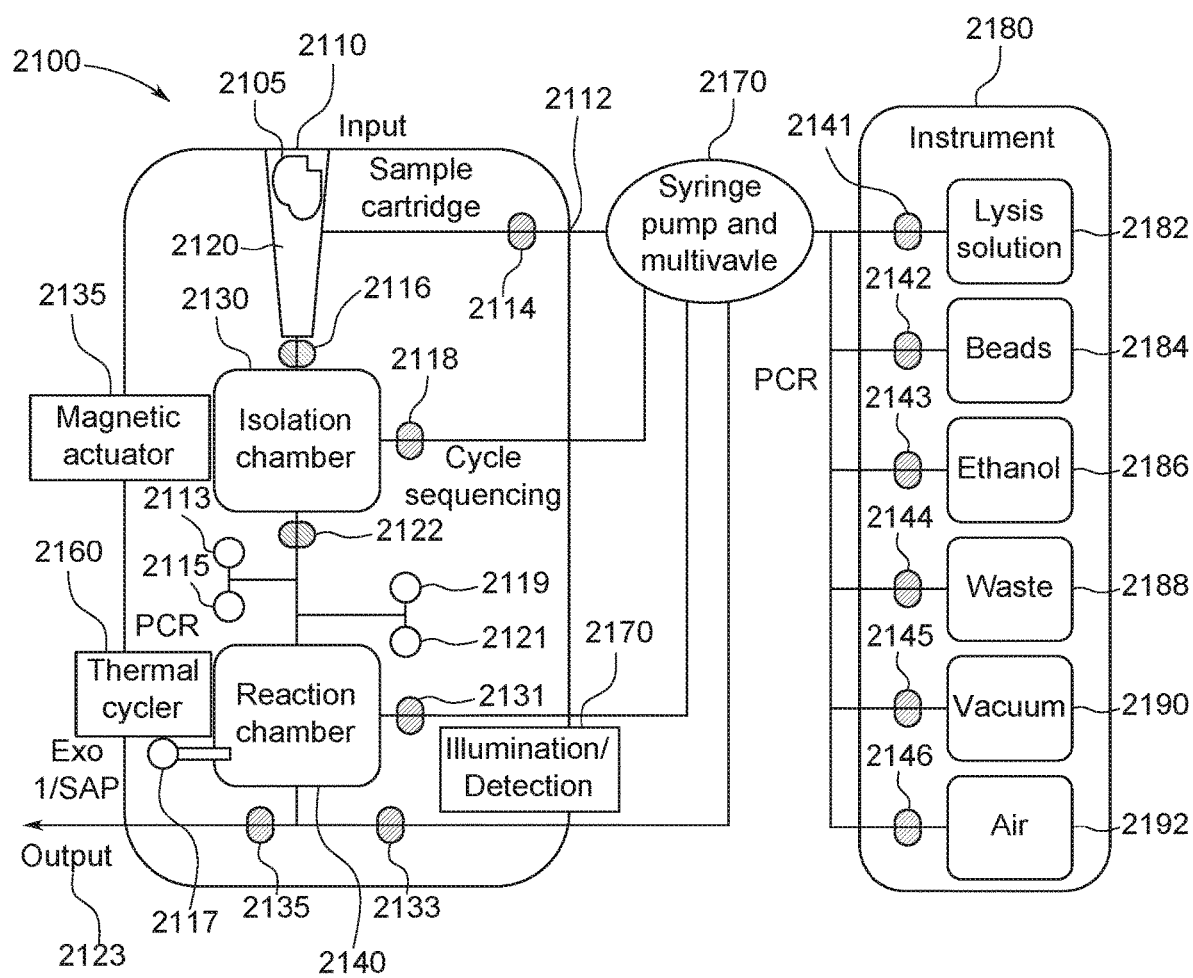
FIG. 21 shows an exemplary cartridge configuration of this disclosure.

An exemplary cartridge 2100 for such an embodiment is shown in FIG. 21. Cartridge 2100 has input 2110. A sample 2105 can be introduced into sample chamber 2120. The cartridge can be engaged with an interface of instrument 2180 configured to supply reagents and motive forces. Cell lysis buffer contained in an off-chip reservoir 2182 can be fed through port 2112 into a fluidic channel in the cartridge and into the sample chamber 2120 by opening valve 2114. Port 2112 can be connected to a syringe 2170 or to another source of positive or negative pressure.

After lysis, lysate can be moved through a fluidic channel on the cartridge into isolation chamber 2130 by opening valve 2116; if required vacuum can be applied by syringe 2170 by opening valve 2118. Magnetically responsive particles, e.g., beads 2184, can be introduced into the isolation chamber before or after introduction of the lysate by opening valve 2118. In another embodiment, the beads can be preloaded into isolation chamber 2130. Polynucleotides can be captured on the particles and immobilized by application of a magnetic force to the isolation chamber 2130 by magnetic actuator 2135. The particles can be washed with, e.g., ethanol 2186, and the wash moved to a waste chamber on cartridge (not shown) or off-cartridge 2188.

Then the polynucleotides can be moved into a reaction chamber 2140 for PCR by opening valve 2122. Reagents for amplifying a specific nucleotide sequence can be introduced into the reaction chamber from sealed compartments through ports 2113 and 2115 or these sealed compartments can contain the reagents in an integrated vial with seals by for example Teflon balls. These include primers, nucleotides, and hot start DNA polymerase. Primers are typically kept separate in a "primer mix" from the other ingredients, mixed as "master mix". A thermal control mechanism in the system, e.g., thermal cycler 2160, can apply heat to perform thermal cycling in reaction chamber 2140 of the cartridge. Following thermal cycling, remaining primers and nucleotide triphosphates can be degraded by adding, for example, exonuclease I and shrimp alkaline phosphatase from a sealed compartment through port 2117. Following reaction, the exonuclease I and shrimp alkaline phosphatase can be degraded by heating to 80 C by thermal cycler 2160.

Reagents for performing cycle sequencing can then be introduced into the reaction chamber, for example, from sealed compartments on the cartridge through ports 2119 and 2121. These include a sequencing primer, nucleotides, hot start DNA polymerase, and labeled dideoxynucleotides (e.g., Big Dye® terminators form Life Technologies®) for dye terminator sequencing. Primers are typically kept separate in a "primer mix" from the other ingredients, mixed as "master mix". Thermal cycling produces dideoxynucleotide-terminated polynucleotides with base specific fluorescent label.

This mixture can then be moved back into isolation chamber 2130. Magnetically responsive particles can be introduced into isolation chamber 2130 for polynucleotide capture and clean up.

Cleaned up polynucleotides can then be pushed, e.g., with air 2192 through output port 2123 to a capillary electrophoresis analysis module for separation, detection, and analysis.

In alternative embodiments, some or all reagents are stored in compartments on the cartridge for use.

B. Amplification and Cycle Sequencing—Multi-Channel

In an alternative embodiment, a cartridge of this disclosure has a fluidic circuit with a plurality of branches, each branch adapted to perform a separate biochemical reaction. For example, each of two branches can be used to perform one of forward and reverse strand cycle sequencing on a sample. The forward strand can be prepared for sequencing in a first branch and the reverse strand can be prepared for sequencing in a second branch. Alternatively, different branches can be used to amplify different target nucleotide sequences from the same sample.

Figure 22:
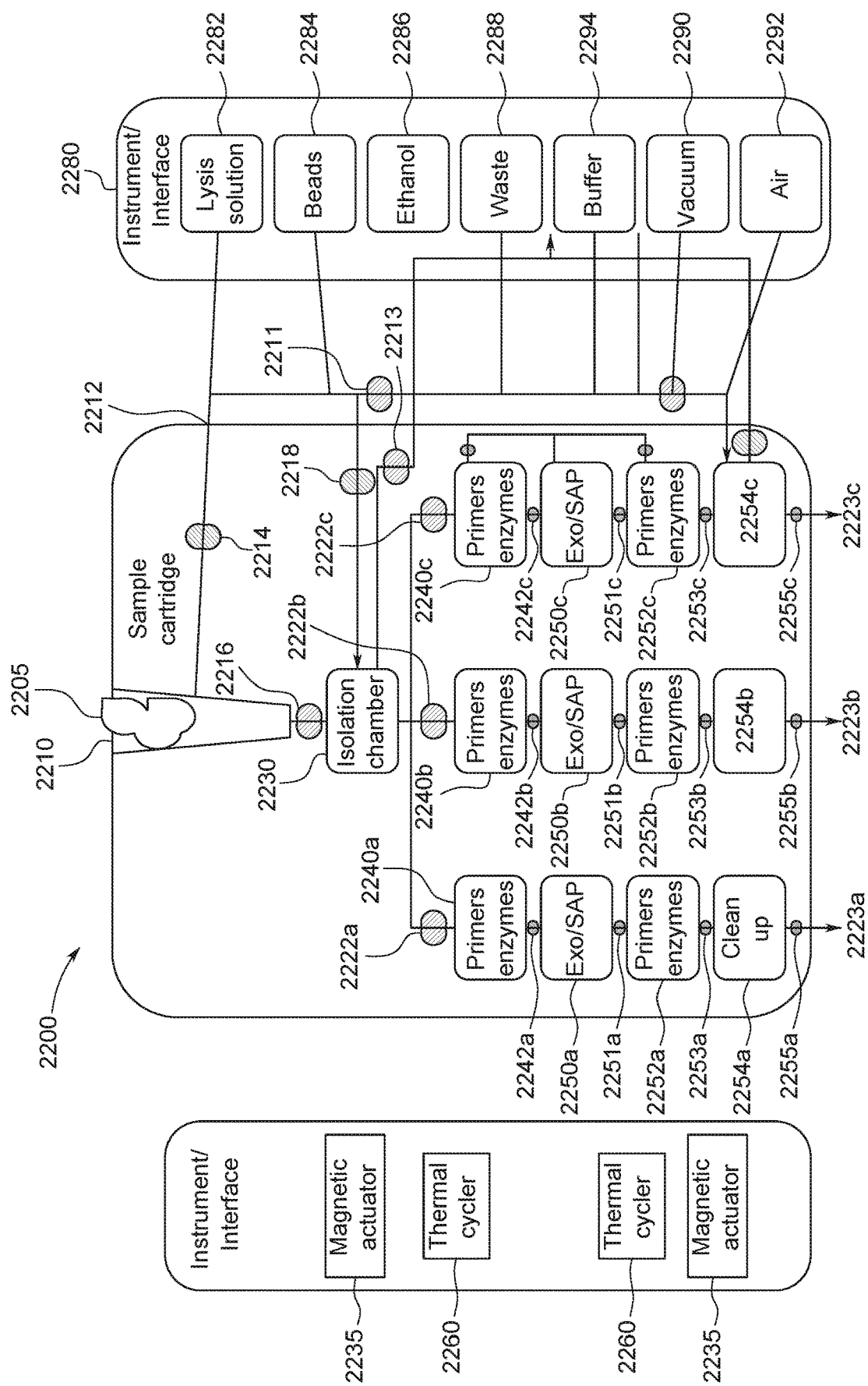
FIG. 22 shows an exemplary cartridge configuration having a circuit with three branches.

An exemplary cartridge 2200 for such an embodiment is shown in FIG. 22. Cartridge 2200 has input 2210. A sample 2205 can be introduced into sample chamber 2220. The cartridge can be engaged with an interface of instrument 2280 configured to supply reagents and motive forces. Cell lysis buffer contained in an off-chip reservoir 2282 can be fed through port 2212 into a fluidic channel in the cartridge and into the sample chamber 2220 by opening valve 2214. The lysis solution can be compatible with particles used to capture polynucleotides. Port 2212 can be connected to a syringe or to another source of positive or negative pressure.

After lysis, lysate can be moved through a fluidic channel on the cartridge into isolation chamber 2230 by opening valve 2216. Magnetically responsive particles, e.g., beads 2284, can be introduced into the isolation chamber before or after introduction of the lysate by opening valve 2218. Polynucleotides can be captured on the particles and immobilized by application of a magnetic force to the isolation chamber 2230 by magnetic actuator 2235. The particles can be washed with, e.g., ethanol 2286, and the wash moved to a waste chamber or off-cartridge 2288.

Then, aliquots of the polynucleotides can be moved into reaction chambers 2240*a-c* for PCR by opening valves 2222*a-c*. This can be done, for example, by opening and closing these valves sequentially, and moving material into each open chamber. Reagents for amplifying a specific nucleotide sequence can be introduced into the reaction chamber from sealed compartments or may be present in lyophilized form. A thermal control mechanism in the system, e.g., thermal cycler 2260, can apply heat to perform thermal cycling in reaction chamber 2240 of the cartridge.

Following thermal cycling, the products can be moved into chambers 2250*a-c* by opening valves 2242*a-c*. Here, primers and nucleotide triphosphates are degraded by, for example, exonuclease I and shrimp alkaline phosphatase present in lyophilized form or added from a sealed compartment. Following reaction, the exonuclease I and shrimp alkaline phosphatase can be degraded by heating to 80 C by thermal cycler 2260.

The samples are then moved into reaction chambers 2250*a-c* by opening valves 2251*a-c* for preparation for cycle sequencing. Again, reagents for performing cycle sequencing can be introduced into the reaction chamber, for example, from sealed compartments on the cartridge or may be present in lyophilized form. Thermal cycling produces dideoxynucleotide-terminated polynucleotides with base specific labels.

The product of the thermal cycling reactions is then moved into clean-up chambers 2254*a-c* by opening valves 2253*a-c*. Magnetically responsive particles can be introduced into clean-up chambers 2254*a-c* for polynucleotide capture and clean up.

Cleaned up polynucleotides can then be pushed, e.g., with air 2292 through output ports 2223*a-c* by opening valves 2255*a-c* to a capillary electrophoresis analysis module for separation, detection, and analysis.

C. DNA Quantification

In another embodiment, cartridges of this disclosure include a DNA quantification function. Such a function can be useful to meter an amount of DNA for amplification determined appropriate for down-stream applications such as SIR amplification.

Figure 23:
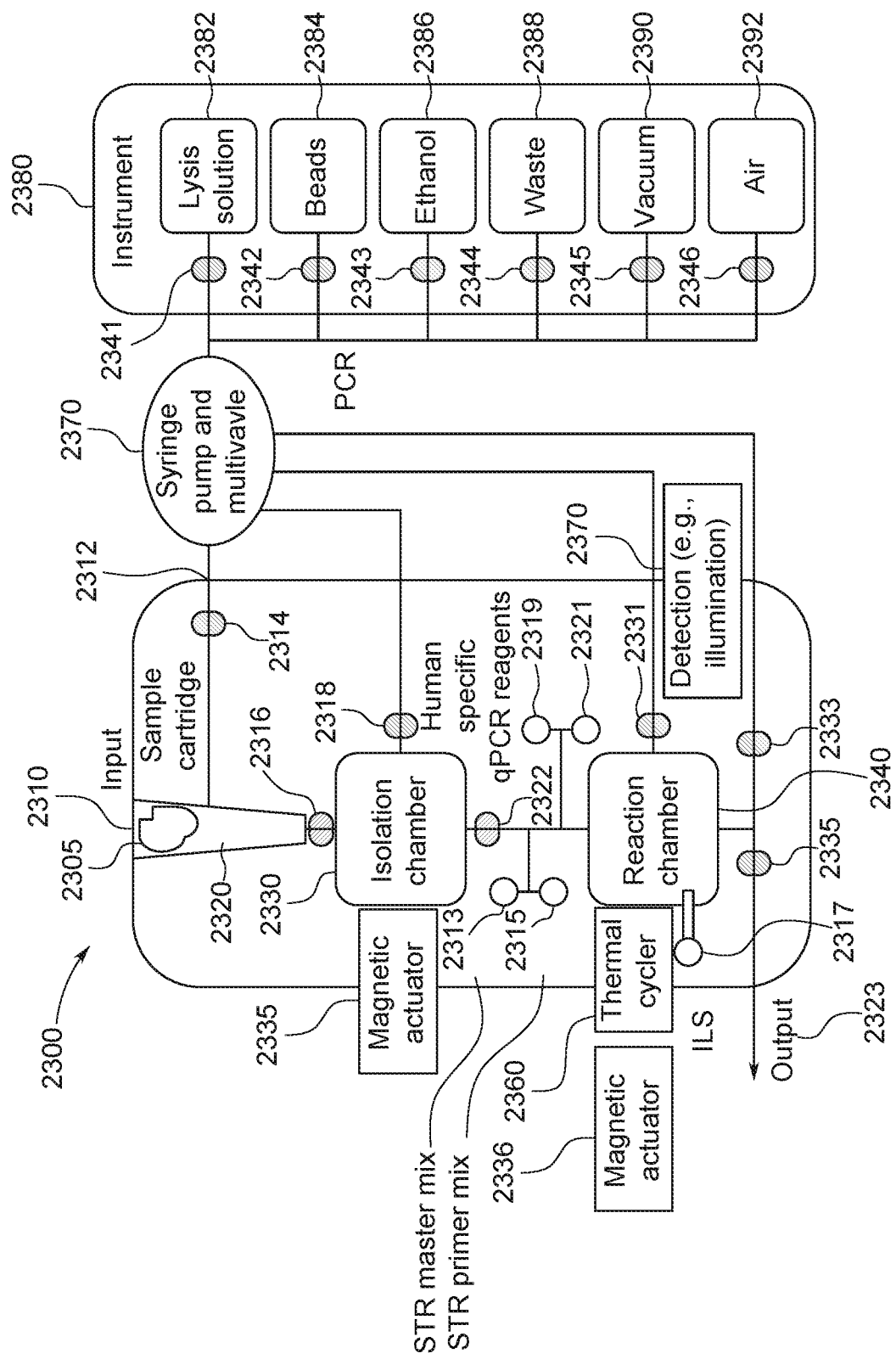
FIG. 23 shows an exemplary cartridge configured to perform real time PCR for quantifying the amount of DNA in a sample.

An exemplary cartridge 2300 for such an embodiment is shown in FIG. 23. Cartridge 2300 has input 2310. A sample 2305 can be introduced into sample chamber 2320. The cartridge can be engaged with an interface of instrument 2380 configured to supply reagents and motive forces. Cell lysis buffer contained in an off-chip reservoir 2382 can be fed through port 2312 into a fluidic channel in the cartridge and into the sample chamber 2320 by opening valve 2314. Port 2312 can be connected to a syringe 2370 or to another source of positive or negative pressure.

After lysis, lysate can be moved through a fluidic channel on the cartridge into isolation chamber 2330 by opening valve 2316. Magnetically responsive particles, e.g., beads 2384, can be introduced into the isolation chamber before or after introduction of the lysate by opening valve 2318. Polynucleotides can be captured on the particles and immobilized by application of a magnetic force to the isolation chamber 2330 by magnetic actuator 2335. The particles can be washed with, e.g., ethanol 2386, and the wash moved to a waste chamber or off-cartridge 2388.

Then, a predetermined amount of the particles with captured DNA can be moved into a reaction chamber 2340 by opening valve 2322. Magnetic actuator 2335 immobilizes the beads in reaction chamber 2340. Human-specific qPCR reagents, such as Quantifiler from Thermo Fisher Scientific™ or Plexor HY System from Promega™, are introduced into the reaction chamber from sealed compartments through ports 2319 and 2321. A thermal control mechanism in the system, e.g., thermal cycler 2360, can apply heat to perform thermal cycling in reaction chamber 2340 of the cartridge for qPCR. A detection device 2370, e.g., using illumination, determines the course of the reaction. This information is used to determine how much DNA is captured per unit bead volume. The amount of beads necessary to carry the predetermined quantity of DNA needed is calculated.

Material in reaction chamber 2340 can then be pushed, e.g., with air, 2392 through output port 2323.

Next, a volume of beads from isolation chamber 2330 determined to carry the desired amount of DNA is moved into reaction chamber 2340. Reagents for performing PCR can then be introduced into the reaction chamber, for example, from sealed compartments on the cartridge through ports 2313 and 2315, and the reaction thermal cycled.

Internal ladder standard 2317 can then be pushed, e.g., with air 2392 through output port 2323 to a capillary electrophoresis analysis module for separation, detection, and analysis.

The cartridges of this disclosure can be used in an integrated system for analyzing a sample, for example, DNA isolation and amplification with real time or end point detection. For real time measurement, the samples can be interrogated by an optical detection system while amplifying in reaction chamber 122. The readout can be the change in fluorescence or by melting point. The probes can be human specific for human identification, forensics, or molecular diagnostic applications, or specific for pathogens for molecular diagnostic applications, or for bioagents for biodefense applications or nonspecific intercalators for determining the amount of DNA present. Amplification methods include, for example, thermal or isothermal amplification reactions, for example, PCR, rolling circle amplification, whole genome amplification, nucleic acid sequence-based amplification, and single strand displacement amplification, single primer isothermal linear amplification (SPIA), loop-mediated isothermal amplification, ligation-mediated rolling circle amplification and the like.

The cartridges of this disclosure can be used in an integrated system for analyzing a sample. The assay can detect a polypeptide (e.g., immunoassay) or a nucleic acid (e.g., PCR or reverse transcriptase followed by amplification). To detect an immunoassay, after lysis of the sample and movement of the lysed sample to reaction chamber 121, ports 115 and 116 can be used to add primary and secondary antibodies to the sample. The detection can be in sample chamber 121 or the sample can be moved through port 113 to a detector.

The assay can be multiplex or single analyte. They can involve any assay to measure the presence, amount, activity, or other characteristics of the sample. These include assays that involve detection by fluorescence, luminescence, chemiluminescence, absorbance, reflectance, transmittance, birefringence, refractive index, colorimetric, and combinations thereof. In this instant disclosure, the enzyme master mix and the substrate might be individually added to the reaction and the progress or endpoint of the assay monitored optically.

In other embodiments, cartridges of this disclosure can be used to prepare samples for additional analytical devices. Analytical methods can include sequencing, chromatography, (e.g., gas or size exclusion) electrometry, ellipsometry, refractrometry, interferometry (e.g., back scattering interferometry), spectrometry (e.g., mass spectrometry, NMR spectrometry, Raman spectroscopy, Surface-enhanced Raman Spectroscopy), surface plasmon resonance. Sequencing methods can include high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS)(Helicos), massively-parallel sequencing, Clonal Single Molecule Array (Solexa), shotgun sequencing, Maxim-Gilbert sequencing, Sanger sequencing, primer walking, sequencing using PacBio, SOLiD, Ion Torrent, or Nanopore platforms.

For SIR applications, after thermal cycling, other reagents such as molecular weight markers (size standards) can be combined with the PCR product. Products of the PCR can be moved off chip for analysis through an output line connected to port 113 (sample out).

In such an embodiment, when the reaction is a short tandem repeat (SIR) reaction, in many jurisdictions for casework samples, the amount of human DNA must be quantified. The typical forensic process is to quantify an extracted sample using real time polymerase chain reaction (PCR) in a separate instrument before the sample is STR amplified. In this instant disclosure, a human specific probe is added to the STR mixture which has fluorescence outside the range used by the STR kit. The reaction chamber 122 is interrogated by a suitable wavelength of light for the human specific probe while the STR is being PCR amplified. The human specific probe can be a quencher such as a Black Hole Quencher® or a TaqMan® probe or other chemistries well know to one skilled in the art. As the PCR cycles increase, the fluorescence from the human specific probe is monitored to quantify the amount of human DNA in the reaction. In a preferred embodiment, the number of amplification cycles can be adjusted based upon the amount of human DNA measured; this can be on a cartridge-by-cartridge monitoring if independent thermal cyclers are in use. One advantage is that the human specific probe will allow the concurrent STR amplification to achieve an optimal amplification and produce an amount of STR product that is optimal for the kit. A second advantage is the real time monitoring concurrent with the STR amplification allows integration of a sample-to-answer system without having an additional separate quantification process. A third advantage is for low copy number samples where there is barely enough sample to produce a good STR profile the integration of the quantification with the SIR amplification prevents the aliquot typically used for quantification from causing the remaining sample to not have enough DNA for a good SIR amplification.

The following examples are offered by way of illustration and not by way of limitation.

EXAMPLES

Example 1

The cartridge is a polypropylene molding with an integrated syringe barrel and sample chamber with a polyethylene heat seal over the area of the fluidics. There is an absorbent material in the waste chamber and a small dot of capture material in the reaction chamber. The barrel is loaded with a quantity of lysis solution (500-1000 uL) isolated between two rubber plungers. There are three reagent vessels on the chip that seal with top and bottom Teflon balls; two for the two parts of the Global Filer mastermix/primer which are loaded with 7-10 uL of solution and one containing a water/ILS solution that is used as a diluent before transfer to the cathode.

Process Steps

1. Load cartridge
  a. User removes cartridge from packaging and load into the instrument. Instrument senses cartridge and engages. The rams are in the retracted state.
  b. Initial valve coining. The rams move to the closed state.
2. Load sample.
  a. The sample is recorded and loaded.
3. Lysis
  a. The lysis heater is turned on.
  b. The valves are set to the appropriate position for delivery from the syringe to the lysis chamber.
  c. The back rubber plunger is engaged by the pump shaft on the instrument.
  d. The entire contents of the syringe is delivered to the lysis chamber.
  e. The valves are moved to the vent position.
  f. The syringe plunger is withdrawn and the syringe fills with air.
  g. The valves move to the delivery position.
  h. The air is injected into the lysis chamber to effect mixing.
4. Transfer and capture (Pulled by syringe inlet from sample chamber into reaction chamber.)
  a. The valves are set to a state where a path is open between the lysis chamber and the waste container that passes through the reaction chamber.
  b. A vacuum is pulled on the waste container.
  c. The lysate is pulled out of the chamber, through the reaction chamber and thus over the capture media, and into the waste where it is absorbed by the material in the chamber.
  d. The valves are switched to the delivery position and the plunger is brought forward.
  e. The pull is executed again to insure all the free lysate material is out of the chamber, through the reaction chamber and in the waste.
5. Mastermix/primer loading and thermocycling. (Reagents pumped into reaction chamber.)
  a. The valves are set to a state where a path is open through the waste to the vent
  b. The two PCR mix vials are emptied into the reaction chamber
  c. All valves are closed.
  d. Thermocycling begins.
6. Polymer fill, concurrent with cycling
  a. Open anode input and anode output valve
  b. Flush anode
  c. Close anode output valve
  d. Fill capillary
  e. Rinse Cathode
7. Mix Sample and diluents (Sample and diluents to mix compartment.)
  a. The valves are set to a state where a path is open between the reaction chamber and the mix chamber to vent.
  b. The diluent vial is emptied up into the mix chamber.
8. Sample delivery to cathode (Product pushed to out port.)
  a. The valves are set to a state with a path from the syringe to the mix chamber to the sample outlet.
  b. The syringe is driven in to place the sample.
9. Sample injection and run
  a. The sample is injected into the capillary
  b. The buffer pump sweeps the sample out of the capillary and flushes the lines
  c. Electrophoresis and detection is run.

Example 2

Another protocol, performed on cartridge 1801, includes the following steps. Valve configurations are shown in FIG. 28.

1 Load Sample Cartridge
2 Prime Lysis to waste*
3 Dispense Lysis to Lysis Chamber
4 Mix Lysis with Air
5 Mix and Heat Lysis
6 Pull Lysate to Waste via Reaction Chamber
7 Push Primer Mix and Master Mix to Reaction Chamber
8 Thermal Cycling
9 Push Internal Lane Standard and Product thru Reaction Chamber to Mix Chamber
10 Push Residual Internal Lane Standard and Product to Mix Chamber with Air Pump
11 Push Product to Cathode
12 Water Rinse of Mix Chamber and Product Output to Cathode
13 Water Rinse of Mix Chamber and Reaction Chamber
14 Flush Water out of Sample Cartridge to Waste Chamber
15 Flush water from Sample Cartridge and Line to Cathode
16 Release 1. All 500 ul will be dispensed into the lysis chamber and then pushed into the waste chamber after step #5.
2. Residual Primer Mix and Master Mix in line to Reaction Chamber just below B0, will remain in Sample Cartridge after the run.
3. Flush Sample Cartridge free of water.

EXAMPLES

Another protocol, performed on a cartridge, includes the following steps. All valves begin in open configuration.

1. Close valves 143 and 148. Load Sample Cartridge.
2. Push lysis buffer from port 112 through valve 142 to Lysis Chamber 120
3. Mix Lysis with Air: Push air through the following open valves and forcing air through the circuit: 112 (open) 143-M 23-M 41-M 22-M 45-M 20
4. Mix and Heat Lysis
5. Pull Lysate to Waste via Reaction Chamber 120^145→122 123→143 ^112
6. Close valve 145; Push Primer Mix 154 and Master Mix 153 to Reaction Chamber 122
7. Close valve 141; Thermal Cycling
8. Open valve 141; Push Internal Lane Standard 152 and Product thru Reaction Chamber 122 to Mix Chamber 121
9. Push Product to Cathode 112^148^121^147^113

Example 4

This example shows a method to perform cycle sequencing on a nucleic acid. (Refer to FIG. 21.)
Raw sample
Lyse with chaotroph
Bead purify DMA
Move to magnetic bead processing chamber
Add paramagnetic beads
Wash 2× with diluted ethanol
Elute DMA or move beads to reaction chamber(s)
Perform PCR amplification (make enough of target region to sequence; if multiple regions are being sequenced, the sample had to be split or parallel samples for each loci)
  Add PCR primers and premix with enzyme from vials 2113 and 2115
  Thermal cycle
Exo1/SAP (destroys PCR primers and nucleotide triphosphates)
  Add Exo/SAP reagents (Exonuclease I/Shrimp Alkaline Phosphatase)
  Incubate 37° C./for 15 min
  Heat to 80° C. for 15 min
Cycle sequence
  Add cycle sequencing primer and premix with enzyme and Big Dye terminators
  Thermal cycle
Cleanup cycle sequencing products using paramagnetic beads
  Move to magnetic bead processing chamber
  Add beads and chaotroph
  Wash 2× with diluted ethanol
  Elute into water or buffer
  Send products to capillary electrophoresis

Example 5

This example shows a method to perform amplification of markers, e.g., diagnostic markers, followed by cycle sequencing of the amplification product. (Refer to FIG. 22.)
Raw sample
Lyse with chaotroph (on cartridge or instrument)
Bead purify DNA
  Add beads to isolation chamber ○ Wash 2× with dilute ethanol ○ Elute DNA or move beads
Purified DNA produced
Split purified DNA to reaction chambers in aliquots
Perform PCR amplification on each locus of interest in separate chambers
  Add PCR primers and premix with enzyme
  Thermal cycle
  Destroy PCR primers and nucleotide triphosphases
  Add Exo/SAP reagents (Exonuclease I/Shrimp Alkaline Phosphatase)
  Incubate 37° C. for ~15 min, heat to 80° C. for 15 min
Cycle sequence
  Add cycle sequencing primer and premix with DNA polymerase and labeled dideoxy terminators
  Thermal cycle
Cleanup cycle sequencing products
  Move cycle sequencing products to cleanup chamber and perform bead-based cleanup
    Add beads and chaotroph ○ Wash 2×
    Elute
  Send products to capillary electrophoresis

Example 6

This example shows a method to quantify amount of human DNA before SIR amplification for human identification or diagnostic fragment sizing (Refer to FIG. 23.)
Raw sample
Lyse with lysis buffer (chaotroph or something else)—bubble+heat
Bead purify DNA
Move lysate to magnetic bead processing chamber
Add beads
Wash 2×
Move 10% beads to reaction chamber where the beads are captured by another magnet
Perform PCR quantification
  Add Quantifiler primers and master-mix
  Thermal cycle
  Excite and detect signal and determine Ct
  Stop after reaching Ct and calculate bead dilution (optimized for downstream STR chemistry)
  Wash reaction chamber
STR amplification in reaction chamber
  Pump beads from magnetic bead processing chamber through reaction chamber into waste adjusting the amount of beads captured by using the qPCR optics (with beam splitters)—i.e. "counting" beads. Actuate magnet to capture correct dilution of beads in reaction chamber.
  Add STR premix and master mix
  Thermocycle
Cleanup STR amp products using a bead-based cleanup (optional based on quantification)
  Add beads and chaotrophs to reaction chamber
  Wash 2× with dilute ethanol
  Elute and keep beads on magnet
  Add ILS
  Move amp product to capillary electrophoresis system

Example?

Analyzing a Sample with an Electrophoresis Cartridge Comprising System

The electrophoresis system is highly integrated and configured to removably engage with a system for sample preparation, processing and analysis. In general, the system comprises there fully-integrated and automated components, i.e., a user interface, a sample cartridge interface and an electrophoresis cartridge interface. The sample cartridge interface and the electrophoresis cartridge interface are configured to releasably engage a sample cartridge for sample processing and an electrophoresis cartridge for sample analysis. The user interface further comprises a control module, a user interface screen and an embedded computer system. The user interface is configured to read and identify the fingerprint of a user and barcodes of sample packaging. A user inputs one or more instructions or requests via the user interface screen and the embedded computer processes the requests and transforms the requests into signals which then initiate the operation of the system.

A user removes an electrophoresis cartridge from packaging and load into the instrument. Instrument senses the cartridge and engages. Multiple communications between the electrophoresis cartridge and the system including: (i) a fluidic communication between an inlet port of the electrophoresis cartridge and an outlet port of a sample cartridge comprised in the system, (ii) an electrical communication between electrodes (i.e., anode and cathode) of the electrophoresis cartridge and a power source of the system, (iii) an optical communication between an optical window of the electrophoresis cartridge and an optics module of the system, (iv) a first thermal communication between the electrophoresis capillary and a first thermo control assembly of the system, (v) a second thermal communication between a gel sub-cartridge of the electrophoresis cartridge and a second thermal control assembly of the system, (vi) a first mechanical communication between an anode sub-assembly of the electrophoresis cartridge and a first mechanical interface of the system, (vii) a second mechanical communication between a cathode sub-assembly of the electrophoresis cartridge and a second mechanical interface of the system, and (viii) a magnetic communication between the electrophoresis cartridge and the system, are established concurrently with the engagement of the electrophoresis cartridge.

Electrophoresis gel stored in the gel sub-cartridge is pumped and injected into the electrophoresis capillary by a high pressure piston comprised in the anode sub-assembly. As the gel is injected, a washing buffer is pumped into a passage of the cathode sub-assembly for removing excessive gel in the cathode sub-assembly. Subsequently, a prepared analyte is directed into the electrophoresis capillary from the sample line in the cathode sub-assembly. A voltage gradient is then applied across two ends of the electrophoresis capillary to perform electrophoretic analysis and separate different components of the analyte which emit distinguishable optical signals upon the illumination of a laser. The signals are detected by a CCD camera comprised in the optics module and subjected to further analysis. Conclusion is drawn based on the results.

All publications and patent applications mentioned in this specification are herein incorporated by reference to the same extent as if each individual publication or patent application was specifically and individually indicated to be incorporated by reference.

While certain embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An instrument comprising a cartridge interface and a cartridge engaged with the cartridge interface, wherein:
  (I) the cartridge comprises:
    (a) a cartridge body comprising a malleable material and having, disposed on a surface of the body, at least one valve body comprising a valve inlet and a valve outlet, each fluidically connected to a fluidic channel, the at least one valve body comprising a groove, the groove comprising a wall including an upper part and a floor, wherein the wall is curved or sloped in a direction that is non-normal to a plane defined by the surface of the body; and
    (b) a layer comprising a deformable material attached to a surface of the cartridge body and sealing the at least one valve body at points of attachment, thereby forming at least one valve,
      wherein the at least one valve body is depressed in the cartridge body relative to the points of attachment,
      wherein the deformable material retains sufficient elasticity after deformation such that in a ground state the valve is open, and
      wherein, while the valve is open, the layer is in contact with the upper part, but is not in contact with the floor; and
  (II) the cartridge interface comprises:
    (A) at least one mechanical actuator, each mechanical actuator positioned to actuate a valve; and
    (B) at least one motor operatively coupled to actuate a mechanical actuator toward or away from a valve.

2. The instrument of claim 1, wherein the cartridge comprises at least one fluidic circuit, wherein the at least one fluidic circuit comprises, as elements, at least one valve, at least one fluid inlet, at least one fluid outlet and at least one compartment, which elements are fluidically connected through fluidic channels.

3. The instrument of claim 1, wherein the cartridge interface comprises a first port engaged with a fluid inlet and a second port engaged with a fluid outlet, and further comprises a pressure source configured to apply pressure through either port to the fluidic circuit.

4. A method of controlling fluid flow in a fluid channel of fluidic cartridge comprising:
  (A) providing an instrument of claim 1, wherein at least one of the fluidic channels comprises a liquid;
  (B) closing a valve by actuating a mechanical actuator against the valve to force the deformable layer against walls of the valve body; and
  (C) releasing the valve by retracting the mechanical actuator away from the valve body.

5. The method of claim 4, further comprising moving the liquid through the valve by applying pressure to liquid in a fluidic channel.

6. The instrument of claim 1, further comprising a ram adapted to apply mechanical pressure on the deformable material in the direction of the cartridge body and at the at least one valve body to close the at least one valve.

7. The instrument of claim 6, wherein one or more of:
  (i) the ram has a tip having a shape that conforms substantially to the shape of the at least one valve body offset for the thickness of the deformable material;
  (ii) the at least one valve body has a cross-sectional shape that exerts a centering action on the ram toward a center of the at least one valve body as the ram applies pressure on the deformable material in the direction of the cartridge body and at the at least one valve body;
  (iii) the ram comprises a flexible material;
  (iv) the ram is mounted on a pivot or a rocker arm; or
  (v) the ram comprises a rotatable wheel mounted at an end of the ram, and wherein the valve body has a cross-sectional shape that conforms substantially to the wheel offset by the thickness of the deformable material.

8. The instrument of claim 6, wherein the ram is configured to translate laterally with respect to the surface of the cartridge body.

9. The instrument of claim 1 further comprising a ram assembly comprising:
  a ram adapted to apply mechanical pressure on the deformable material in the direction of the cartridge body and at the at least one valve body to close the at least one valve; and
  a centering arm configured for coarse centering of the ram.

10. The instrument of claim 1, wherein
while the valve is open, the layer is bonded to the upper part, but is not bonded to the floor.

11. The instrument of claim 1, wherein the layer is bonded to the surface of the cartridge body.

12. The instrument of claim 1, further comprising a relief adapted to accept a centering arm for guiding a ram head.

13. The instrument of claim 1, wherein the valve body has a depth, from its bottom to the height of the top of a ridge (if present) or a plane generally defined by the cartridge body surface of between 50 microns and 200 microns, e.g., about 100 microns.

14. The instrument of claim 1, wherein the valve body has an aspect ratio of depth-to-width greater than 1.

15. The instrument of claim 1, wherein the aspect ratio (width:depth) of the valve body is between about 1:1.5 and 1:0.1, e.g., 1:1.2 to 1:0.7.

16. The instrument of claim 1, wherein the body further comprises a reagent compartment comprising a reagent.

17. The instrument of claim 16, wherein the reagent is selected from the group consisting of nucleic acid primers, nucleotides, and a DNA polymerase sufficient to perform PCR.

18. The instrument of claim 16, wherein the compartment comprises an openable seal that, when opened, puts the compartment in fluidic communication through a via with a fluidic channel on the surface.

19. The instrument of claim 18, wherein the valve body is wider than the fluidic channel.

20. The instrument of claim 1, wherein the deformable layer retains sufficient elasticity to resist valve closure when negative pressure (e.g., suction) up to about 10 psi is exerted on a fluidic channel communicating with the valve.

* * * * *